(12) United States Patent
Brown et al.

(10) Patent No.: US 10,351,545 B2
(45) Date of Patent: Jul. 16, 2019

(54) MUSCARINIC AGONISTS

(71) Applicant: Heptares Therapeutics Limited, Cambridge (GB)

(72) Inventors: Giles Albert Brown, Cambridge (GB); Miles Stuart Congreve, Cambridge (GB); Mark Pickworth, Cambridge (GB); Benjamin Gerald Tehan, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 0 days.

(21) Appl. No.: 15/699,674

(22) Filed: Sep. 8, 2017

(65) Prior Publication Data
US 2018/0022726 A1    Jan. 25, 2018

Related U.S. Application Data

(62) Division of application No. 15/227,325, filed on Aug. 3, 2016, now Pat. No. 9,758,506.

(30) Foreign Application Priority Data

Aug. 3, 2015 (GB) .................................. 1513742.5

(51) Int. Cl.
| | | |
|---|---|---|
| *C07D 401/04* | (2006.01) | |
| *C07D 401/08* | (2006.01) | |
| *A61K 31/451* | (2006.01) | |
| *A61K 31/4523* | (2006.01) | |

(52) U.S. Cl.
CPC .......... *C07D 401/04* (2013.01); *C07D 401/08* (2013.01); *A61K 31/451* (2013.01); *A61K 31/4523* (2013.01)

(58) Field of Classification Search
CPC ................ C07D 401/04; C07D 401/08; A61K 31/4523; A61K 31/451
See application file for complete search history.

(56) References Cited

U.S. PATENT DOCUMENTS 9,758,506 B2    9/2017   Brown et al.

FOREIGN PATENT DOCUMENTS

| WO | 2007/100670 A1 | 9/2007 |
|---|---|---|
| WO | 2013/072705 A1 | 5/2013 |
| WO | 2014/045031 A1 | 3/2014 |
| WO | 2015118342 A1 | 8/2015 |

OTHER PUBLICATIONS

Foster et al, 10, 183-191 (Year: 2014).*
GB Search Report, GB1513742.5, dated May 10, 2016.
International Search Report and Written Opinion PCT/GB2016/052386, dated Oct. 31, 2016.

* cited by examiner

*Primary Examiner* — Sudhakar Katakam
(74) *Attorney, Agent, or Firm* — McCarter & English, LLP; Steven G. Daivs; Mei Bai

(57) ABSTRACT

This invention relates to compounds that are agonists of the muscarinic $M_1$ receptor and/or $M_4$ receptor and which are useful in the treatment of muscarinic $M_1/M_4$ receptor mediated diseases. Also provided are pharmaceutical compositions containing the compounds and the therapeutic uses of the compounds. Compounds include those according to formula (1a)

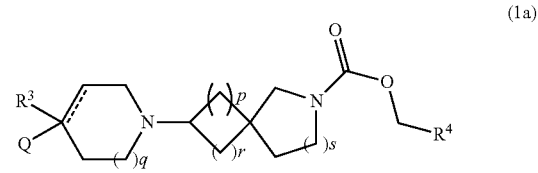

or a salt thereof, wherein p, q, r, s, Q, $R^3$ and $R^4$ are as defined herein.

30 Claims, 1 Drawing Sheet

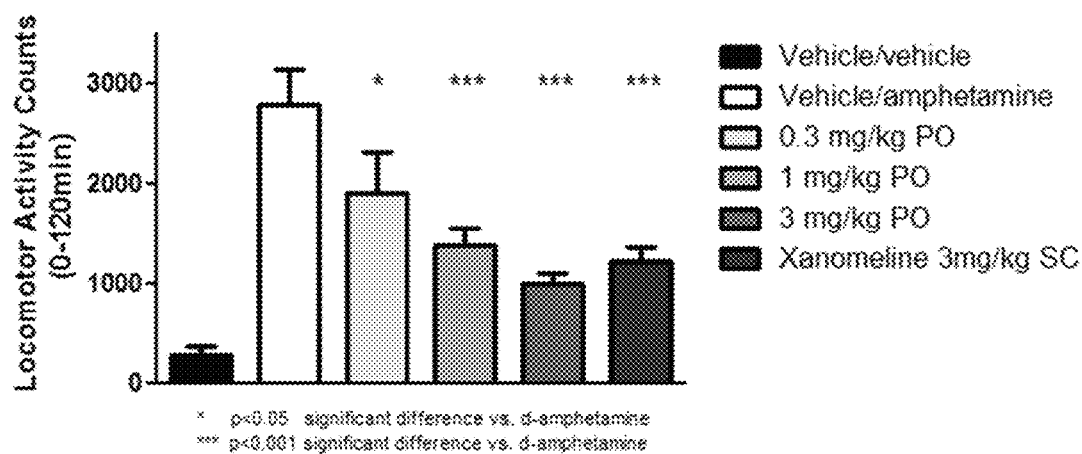
Example 2-1 isomer 2

MUSCARINIC AGONISTS

RELATED APPLICATION INFORMATION

This application is a divisional of U.S. patent application Ser. No. 15/227,325, filed on Aug. 3, 2016, which claims priority to GB Application No. 1513742.5, filed on Aug. 3, 2015, the contents of which are herein incorporated by reference.

This invention relates to compounds that are agonists of the muscarinic $M_1$ receptor and/or $M_4$ receptor and which are useful in the treatment of muscarinic $M_1/M_4$ receptor mediated diseases. Also provided are pharmaceutical compositions containing the compounds and the therapeutic uses of the compounds.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which also has cognitive impairment as an important component of the clinical picture, mAChR density is reduced in the pre-frontal cortex, hippocampus and caudate putamen of schizophrenic subjects (Dean et al., 2002 *Mol Psychiatry*). Furthermore, in animal models, blockade or damage to central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting adverse events resulting from stimulation of peripheral $M_2$ and $M_3$ mAChRs including disturbed gastrointestinal motility, bradycardia, nausea and vomiting (www.drugs.com/pro/donepezil.html; and www.drugs.com/pro/rivastigmine.html).

Further discovery efforts have targeted the identification of direct $M_1$ mAChR agonists with the aim of inducing selective improvements in cognitive function with a favourable adverse effect profile. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain pathologies: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, nonamyloidgenic and amyloidgenic. Cleavage of APP by γ-secretase is common to both pathways, but in the former APP is cleaved by an α-secretase to yield soluble APPα. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3×TgAD transgenic mouse, a model of the different components of Alzheimer's disease (Caccamo et al., 2006 *Neuron*). The mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Preclinical studies have suggested that mAChR agonists display an atypical antipsychotic-like profile in a range of pre-clinical paradigms. The mAChR agonist, xanomeline, reverses a number of dopamine mediated behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*). Muscarinic receptors have also been implicated in the neurobiology of addiction. The reinforcing effects of cocaine and other addictive substances are mediated by the mesolimbic dopamine system where behavioral and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore xanomeline has been demonstrated to block the effects of cocaine in these models.

Muscarinic receptors are also involved in the control of movement and potentially represent novel treatments for movement disorders such as Parkinson's disease, ADHD, Huntingdon's disease, tourette's syndrome and other syndromes associated with dopaminergic dysfunction as an underlying pathogenetic factor driving disease.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic adverse events, including nausea, gastrointestinal pain, diahorrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage; however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/ traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the $M_1$ receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 Bioorg Med Chem Lett; Johnson et al., 2010 Bioorg Med Chem Lett; Budzik et al., 2010 ACS Med Chem Lett). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

The Invention

The present invention provides compounds having activity as muscarinic $M_1$ and/or $M_4$ receptor agonists. More particularly, the invention provides compounds that exhibit selectivity for the $M_1$ receptor and/or the $M_4$ receptor relative to the $M_2$ and $M_3$ receptor subtypes.

Accordingly, in one embodiment (Embodiment 1.1), the invention provides a compound of the formula (1) or formula (1a):

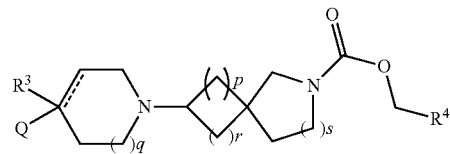

or a salt thereof, wherein
p is 1 or 2;
q is 0, 1 or 2;
r is 1 or 2;
s is 0 or 1, where the total of r and s is 1 or 2;
Q is $CR^1R^2NR^5R^6$, $NR^5R^6$, $OR^7$, $SR^7$;
$R^1$ is selected from hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;
$R^2$ is selected from hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;
$R^3$ is selected from hydrogen; fluorine; cyano; hydroxy; amino; and a $C_{1-6}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;
$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
$R^5$ is selected from hydroxy; $OR^7$; $COR^7$; $COOR^7$; $CH_2COR^7$; $CH_2COOR^7$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;
$R^6$ is selected from hydroxy; $OR^7$; $COR^7$; $COOR^7$; $CH_2COR^7$; $CH_2COOR^7$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof; and
$R^7$ is selected from hydrogen a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $C_{1-4}$ hydrocarbon group. W where W is an optionally substituted 5- or 6-membered ring containing 0, 1, 2 or 3 heteroatoms selected from O, N and S and oxidized forms thereof; and the dotted line indicates an optional second carbon-carbon bond, provided that when a second carbon-carbon bond is present, then $R^3$ is absent.

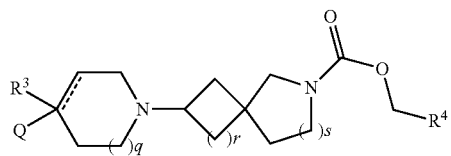

(1)

or a salt thereof, wherein q is 0, 1 or 2;

r is 1 or 2;

s is 0 or 1, where the total of r and s is 1 or 2;

Q is $CR^1R^2NR^5R^6$, $NR^5R^6$, $OR^7$, $SR^7$;

$R^1$ is selected from hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^2$ is selected from hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^3$ is selected from hydrogen; fluorine; cyano; hydroxy; amino; and a $C_{1-6}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$ is selected from hydroxy; $OR^7$; $COR^7$; $COOR^7$; $CH_2COR^7$; $CH_2COOR^7$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;

$R^6$ is selected from hydroxy; $OR^7$; $COR^7$; $COOR^7$; $CH_2COR^7$; $CH_2COOR^7$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof; and $R^7$ is selected from hydrogen a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;

and the dotted line indicates an optional second carbon-carbon bond, provided that when a second carbon-carbon bond is present, then $R^3$ is absent.

Particular compounds of the formula (1) or formula (1a) are as defined in the Embodiments 1.2 to 1.50 set out below.

1.2 A compound according to Embodiment 1.1 wherein Q is $NR^5R^6$ 1.3 A compound according to Embodiment 1.1 wherein Q is $CR^1R^2NR^5R^6$.

1.4 A compound according to Embodiments 1.1 to 1.3 wherein $R^1$ is selected from hydrogen or a $C_{1-3}$ alkyl group.

1.5 A compound according to Embodiment 1.4 wherein $R^1$ is selected from hydrogen, methyl or ethyl.

1.6 A compound according to Embodiments 1.1 to 1.5 wherein $R^2$ is selected from hydrogen or a $C_{1-3}$ alkyl group.

1.7 A compound according to Embodiment 1.6 wherein $R^2$ is selected from hydrogen, methyl or ethyl.

1.8 A compound according to Embodiment 1.6 wherein $R^1$ is H and $R^2$ is selected from hydrogen or methyl.

1.9 A compound according to any one of Embodiments 1.1 to 1.8 wherein $R^5$ is selected from a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof.

1.10 A compound according to any one of Embodiments 1.1 to 1.8 wherein $R^5$ is selected from a $C_{1-4}$ alkyl group which is optionally substituted with one to four fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered aromatic ring containing 0, 1, 2 or 3 heteroatoms selected from O, N and S.

1.11 A compound according to any one of Embodiments 1.1 to 1.8 wherein $R^5$ is selected from a $C_{1-4}$ alkyl group which is optionally substituted with one to four fluorine atoms; and a group W or $CH_2W$ where W is an optionally substituted 5- or 6-membered aromatic ring containing 0, 1, 2 or 3 heteroatoms selected from O, N and S.

1.12 A compound according to any one of Embodiments 1.1 to 1.8 wherein $R^5$ is selected from methyl, ethyl, propyl, isopropyl, cyclopropyl, fluoroethyl, difluoroethyl, trifluoroethyl, butyl or cyclobutyl.

1.13 A compound according to any one of Embodiments 1.1 to 1.8 wherein $R^5$ is a group W or $CH_2W$ where W is an optionally substituted phenyl, pyridyl or isoxazole ring.

1.14 A compound according to any one of Embodiments 1.1 to 1.13 wherein $R^6$ is selected from; $COR^7$; $COOR^7$; $CH_2COR^7$; $CH_2COOR^7$ or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.15 A compound according to any one of Embodiments 1.1 to 1.13 wherein $R^6$ is selected from methyl, ethyl, trifluoroethyl, hydroxyethyl or methoxyethyl.

1.16 A compound according to any one of Embodiments 1.1 to 1.13 wherein $R^6$ is selected from; $COR^7$; $COOR^7$; $CH_2COR^7$; $CH_2COOR^7$, wherein $R^7$ is selected from H, methyl, fluoromethyl, difluoromethyl, trifluoromethyl, ethyl, fluoroethyl, difluoroethyl or trifluoroethyl.

1.17 A compound according to any one of Embodiments 1.1 to 1.16 wherein the dotted line represents a second carbon-carbon bond and $R^3$ is absent.

1.18 A compound according to any one of Embodiments 1.1 to 1.16 wherein $R^3$ is present and the optional second carbon-carbon bond is absent.

1.19 A compound according to Embodiment 1.18 wherein $R^3$ is selected from hydrogen; fluorine; cyano; hydroxy; amino; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.20 A compound according to Embodiment 1.19 wherein $R^3$ is selected from hydrogen; fluorine; cyano; hydroxy; amino; and a $C_{1-4}$ alkyl group which is optionally substituted with one to four fluorine atoms.

1.21 A compound according to Embodiment 1.20 wherein $R^3$ is selected from hydrogen; fluorine; cyano; hydroxy; amino; $C_{14}$ alkyl and $C_{1-4}$ alkoxy, wherein the $C_{1-4}$ alkyl and $C_{1-4}$ alkoxy are each optionally substituted with one to four fluorine atoms.

1.22 A compound according to Embodiment 1.21 wherein $R^3$ is selected from hydrogen; fluorine; hydroxy and methoxy.

1.23 A compound according to Embodiment 1.22 wherein $R^3$ is hydrogen.

1.24 A compound according to any one of Embodiments 1.1 to 1.23 wherein $R^4$ is hydrogen or an acyclic $C_{1-6}$ hydrocarbon group.

1.25 A compound according to Embodiment 1.24 wherein $R^4$ is hydrogen or an acyclic $C_{1-3}$ hydrocarbon group.

1.26 A compound according to Embodiment 1.25 wherein $R^4$ is hydrogen or a $C_{1-3}$ alkyl group or a $C_{2-3}$ alkynyl group.

1.27 A compound according to Embodiment 1.26 wherein $R^4$ is selected from hydrogen, methyl, ethyl, ethynyl and 1-propynyl.

1.28 A compound according to Embodiment 1.27 wherein $R^4$ is selected from hydrogen and methyl.

1.29 A compound according to Embodiment 1.28 wherein $R^4$ is methyl.

1.30 A compound according to any one of the preceding Embodiments wherein $R^7$, when present, is selected from hydrogen a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ or $C_{1-4}$ hydrocarbon group—W where W is an optionally substituted 5- or 6-membered ring containing 0, 1, 2 or 3 heteroatoms selected from O, N and S and oxidized forms thereof;

1.31 A compound according to Embodiment 1.30 wherein $R^7$ is a non-aromatic $C_{1-4}$ hydrocarbon group optionally substituted with one or more fluorine atoms.

1.32 A compound according to Embodiment 1.30 wherein $R^7$ is a $C_{1-4}$ alkyl group.

1.33 A compound according to any one of Embodiments 1.1 to 1.32 wherein q is 0.

1.34 A compound according to any one of Embodiments 1.1 to 1.32 wherein q is 1.

1.35 A compound according to any one of Embodiments 1.1 to 1.32 wherein q is 2.

1.36 A compound according to any one of Embodiments 1.1 to 1.35 wherein r is 1.

1.37 A compound according to any one of Embodiments 1.1 to 1.35 wherein s is 0.

1.38 A compound according to any one of Embodiments 1.1 to 1.36 wherein r is 1 and s is 1.

1.39 A compound according to any one of Embodiments 1.1 to 1.37 wherein r is 1 and s is 0.

1.40 A compound according to any one of Embodiments 1.1 to 1.39 wherein p is 1.

1.41 A compound according to any one of Embodiments 1.1 to 1.39 wherein p is 2.

1.42 A compound according to any one of Embodiments 1.1 to 1.41 wherein the moiety:

is selected from groups A to KKK below:

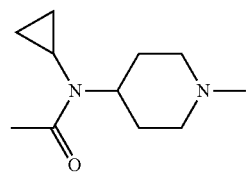

A

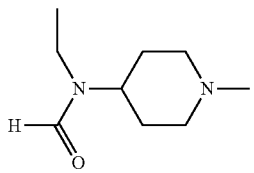

B

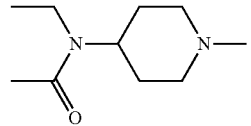

C

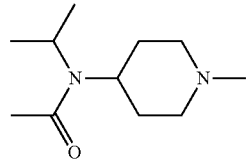

D

-continued

-continued
W
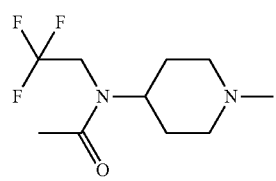
X
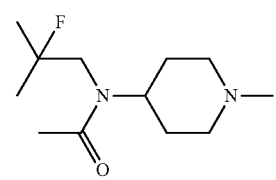
Y
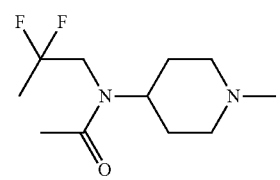
Z
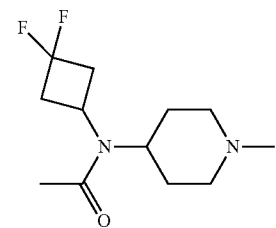
AA
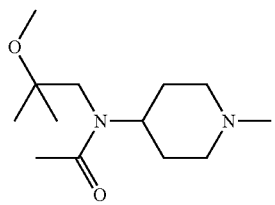
BB
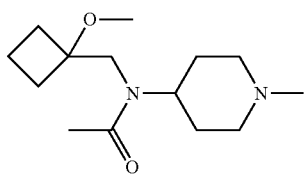
CC
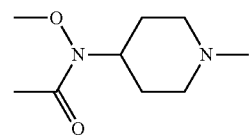
DD
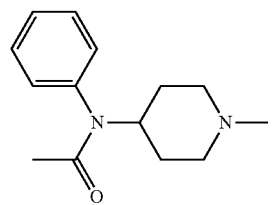
-continued
EE
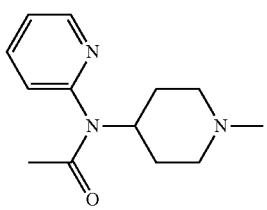
FF
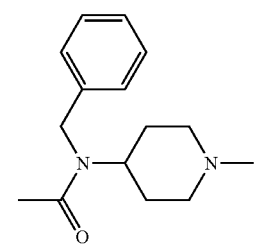
GG
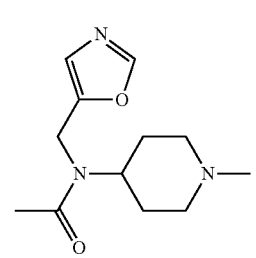
HH
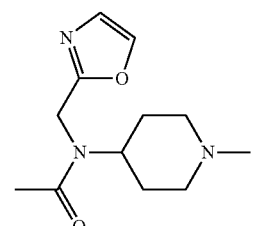
II
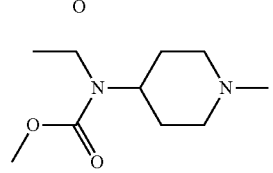
JJ
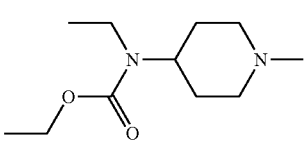
KK
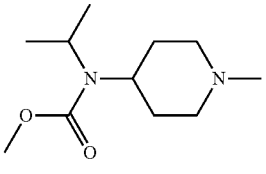
LL
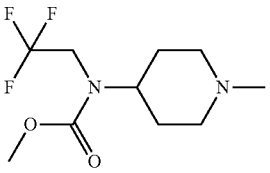

-continued
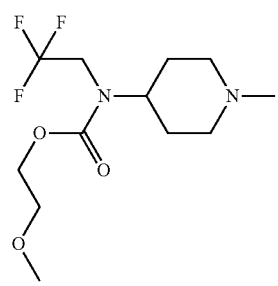 MM
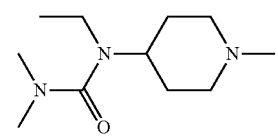 NN
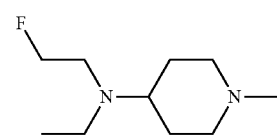 OO
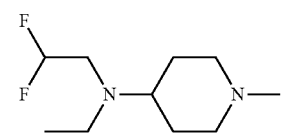 PP
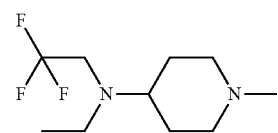 QQ
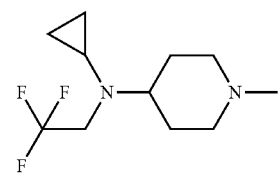 RR
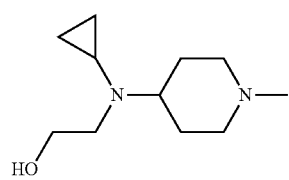 SS
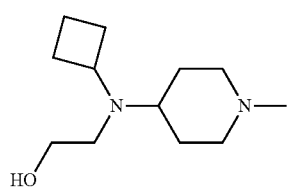 TT
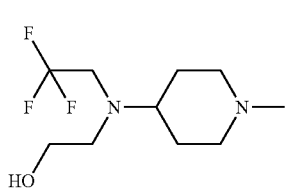 UU
-continued
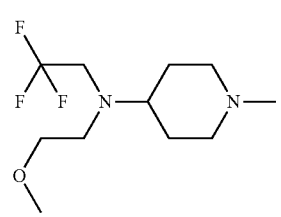 VV
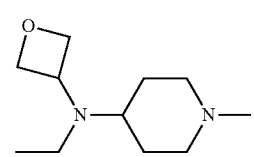 WW
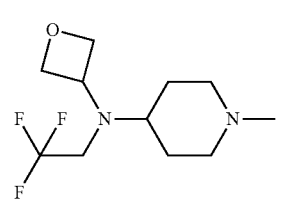 XX
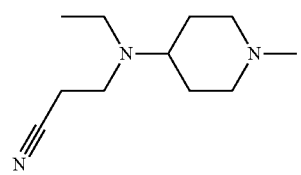 YY
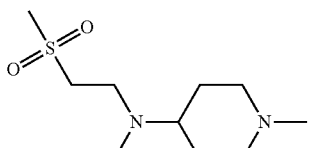 ZZ
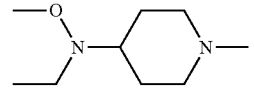 AAA
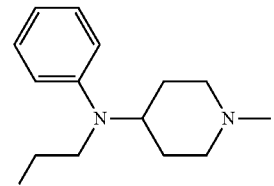 BBB
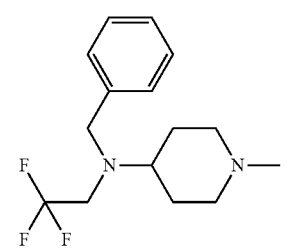 CCC -continued

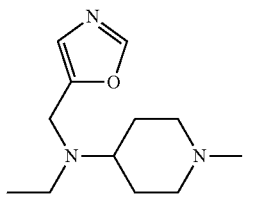
DDD

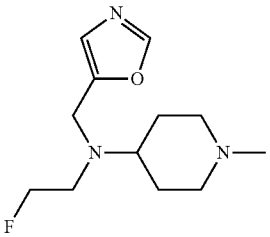
EEE

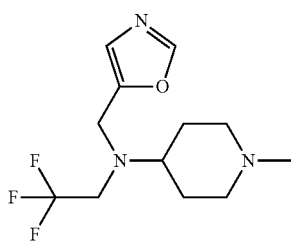
FFF

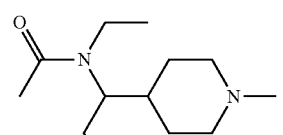
GGG

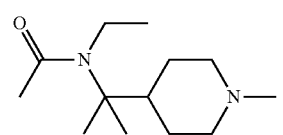
HHH

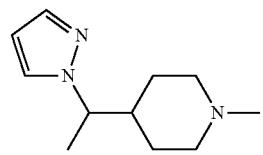
III

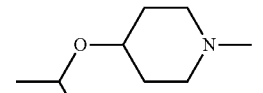
JJJ

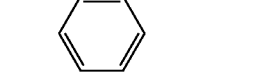
KKK

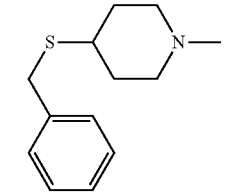

1.43 A compound according to having the formula (2) or formula (2a):

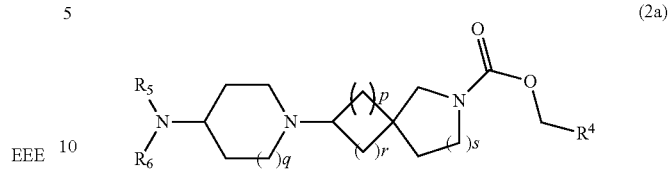
(2a)

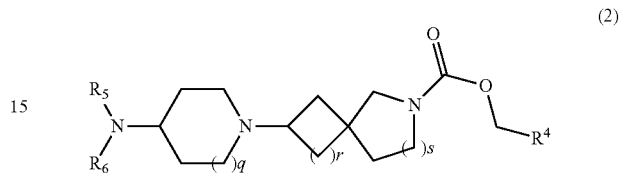
(2)

wherein p, q, r, s, $R^4$ $R^5$ and $R^6$ are is as defined in any one of Embodiments 1.1 to 1.39.

1.44 A compound according to having the formula (3) or formula (3a):

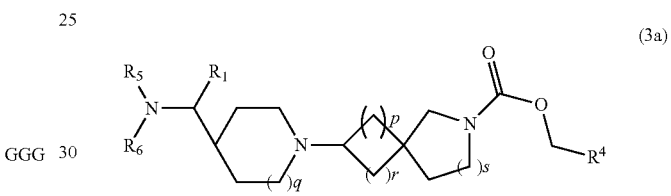
(3a)

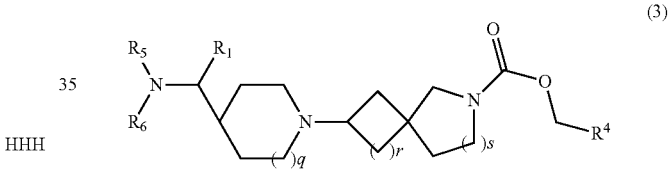
(3)

wherein $R^1$ is H or methyl and p, q, r, s, $R^4$ $R^5$ and $R^6$ are is as defined in any one of Embodiments 1.1 to 1.41.

1.45 A compound according to having the formula (4):

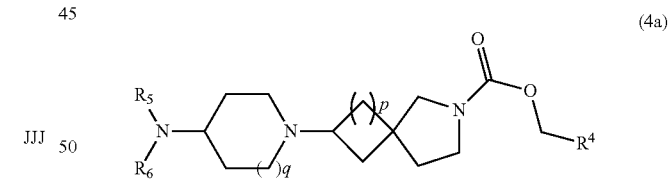
(4a)

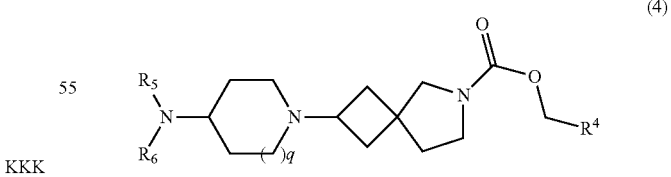
(4)

wherein q is 1 or 2 and p, $R^4$ $R^5$ and $R^6$ are is as defined in any one of Embodiments 1.1 to 1.32.

1.46 A compound according to Embodiment 1.1 which is as defined in any one of Examples 1-1 to 4-1.

1.47 A compound according to any one of Embodiments 1.1 to 1.46 having a molecular weight of less than 550.

1.48 A compound according to Embodiment 1.47 having a molecular weight of less than 500.

1.49 A compound according to Embodiment 1.48 having a molecular weight of, or less than 450.
1.50 A compound according to any one of Embodiments 1.1 to 1.49 which is in the form of a salt.
1.51 A compound according to Embodiment 1.50 wherein the salt is an acid addition salt.
1.52 A compound according to Embodiment 1.50 or Embodiment 1.51 wherein the salt is a pharmaceutically acceptable salt.

Definitions

In this application, the following definitions apply, unless indicated otherwise.

The term "treatment", in relation to the uses of the compounds of the formula (1) or formula (1a), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" as in "$C_{1-10}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" aryl, heteroaryl and "cycloalkenyl" are used in their conventional sense (e.g. as defined in the IUPAC Gold Book) unless indicated otherwise.

The term "saturated hydrocarbon group" as in "$C_{1-4}$ saturated hydrocarbon group" refers to a hydrocarbon group containing no carbon-carbon double bonds or triple bonds. The saturated hydrocarbon group can therefore be an alkyl group, a cycloalkyl group, a cycloalkylalkyl group, an alkylcycloalkyl group or a alkylcycloalkylalkyl group. Examples of $C_{1-4}$ saturated hydrocarbon groups include $C_{1-4}$ alkyl groups, cyclopropyl, cyclobutyl and cyclopropylmethyl.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^2$, $R^3$ and $R^4$ above, where stated, one or two but not all, carbon atoms of the non-aromatic hydrocarbon group may optionally be replaced by a heteroatom selected from O, N and S and (in the case of $R^1$ and $R^4$) oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—S(O)$_2$—$CH_2$—, replacement of a carbon atom in a —$CH_2$—$CH_2$—$CH_2$— chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1) or formula (1a) can exist in the form of salts, for example acid addition salts or, in certain cases salts of organic and inorganic bases such as carboxylate, sulfonate and phosphate salts. All such salts are within the scope of this invention, and references to compounds of the formula (1) or formula (1a) include the salt forms of the compounds as defined in Embodiments 1.50 to 1.52.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.120) may be formed with a wide variety of acids, both inorganic and organic. Examples of acid addition salts falling within Embodiment 1.120 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1 S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1) or formula (1a) contain an amine function, these may form quaternary ammonium salts, for example by reaction with an alkylating agent according to methods well known to the skilled person. Such quaternary ammonium compounds are within the scope of formula (1) or formula (1a) respectively.

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.121), the invention provides a geometric isomer of a compound according to any one of Embodiments 1.1 to 1.52.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.132) the invention provides a compound according to any one of Embodiments 1.1 to 1.121 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.133), the invention provides compositions containing a compound according to Embodiment 1.132 having one or more chiral centres, wherein at least 55% (e.g. at least 60%, 65%, 70%, 75%, 80%, 85%, 90% or 95%) of the compound of Embodiment 1.108 is present as a single optical isomer (e.g. enantiomer or diastereoisomer).

In one general embodiment (Embodiment 1.134), 99% or more (e.g. substantially all) of the total amount of the compound (or compound for use) of Embodiment 1.132 is present as a single optical isomer.

For example, in one embodiment (Embodiment 1.135) the compound is present as a single enantiomer.

In another embodiment (Embodiment 1.136), the compound is present as a single diastereoisomer.

The invention also provides mixtures of optical isomers, which may be racemic or non-racemic. Thus, the invention provides:

1.137 A compound according to Embodiment 1.132 which is in the form of a racemic mixture of optical isomers.
1.138 A compound according to Embodiment 1.132 which is in the form of a non-racemic mixture of optical isomers.

Isotopes

The compounds of the invention as defined in any one of Embodiments 1.1 to 1.138 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.142), the compound of any one of Embodiments 1.1 to 1.140 contains no radioactive isotopes. Such compounds are preferred for therapeutic use.

In another embodiment (Embodiment 1.143), however, the compound of any one of Embodiments 1.1 to 1.140 may contain one or more radioisotopes. Compounds containing such radioisotopes may be useful in a diagnostic context.

Solvates

Compounds of the formula (1) or formula (1a) as defined in any one of Embodiments 1.1 to 1.143 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.153 and 1.154, the invention provides:

1.153 A compound according to any one of Embodiments 1.1 to 1.143 in the form of a solvate.

1.154 A compound according to Embodiment 1.153 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.155), the invention provides a compound as defined in any one of Embodiments 1.1 to 1.143 in an anhydrous form (e.g. anhydrous crystalline form).

Crystalline and Amorphous Forms

The compounds of any one of Embodiments 1.1 to 1.155 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.160 A compound according to any one of Embodiments 1.1 to 1.155 in a crystalline form.

1.161 A compound according to any one of Embodiments 1.1 to 1.155 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.162 A compound according to any one of Embodiments 1.1 to 1.155 which is in an amorphous form.

Prodrugs

The compounds of the formula (1) or formula (1a) as defined in any one of Embodiments 1.1 to 1.162 may be presented in the form of a pro-drug. By "prodrugs" is meant for example any compound that is converted in vivo into a biologically active compound of the formula (1) or formula (1a) respectively, as defined in any one of Embodiments 1.1 to 1.162.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.170), the invention provides a pro-drug of a compound as defined in any one of Embodiments 1.1 to 1.170 wherein the compound contains a functional group which is convertable under physiological conditions to form a hydroxyl group or amino group.

Complexes and Clathrates

Also encompassed by formula (1) or formula (1a) in Embodiments 1.1 to 1.170 are complexes (e.g. inclusion complexes or clathrates with compounds such as cyclodextrins, or complexes with metals) of the compounds of Embodiments 1.1 to 1.170.

Accordingly, in another embodiment (Embodiment 1.180), the invention provides a compound according to any one of Embodiments 1.1 to 1.170 in the form of a complex or clathrate.

Biological Activity and Therapeutic Uses

The compounds of the present invention have activity as muscarinic $M_1$ and/or $M_4$ receptor agonists. The muscarinic activity of the compounds can be determined using the Phospho-ERK1/2 assay described in Example A below.

A significant advantage of compounds of the invention is that they are highly selective for the $M_1$ and/or $M_4$ receptor relative to the $M_2$ and $M_3$ receptor subtypes. Compounds of the invention are not agonists of the $M_2$ and $M_3$ receptor subtypes. For example, whereas compounds of the invention typically have pEC$_{50}$ values of at least 6 (preferably at least 6.5) and E$_{max}$ values of greater than 80 (preferably greater than 95) against the M$_1$ receptor in the functional assay described in Example A, they may have pEC$_{50}$ values of less than 5 and E$_{max}$ values of less than 20% when tested against the M$_2$ and M$_3$ subtypes in the functional assay of Example A.

Accordingly, in Embodiments 2.1 to 2.9, the invention provides:

2.1 A compound according to any one of Embodiments 1.1 to 1.180 for use in medicine.

2.2 A compound according to any one of Embodiments 1.1 to 1.180 for use as a muscarinic M$_1$ and/or M$_4$ receptor agonist.

2.3 A compound according to any one of Embodiments 1.1 to 1.180 which is a muscarinic M$_1$ receptor agonist having a pEC$_{50}$ in the range from 6.0 to 8.0 and an E$_{max}$ of at least 90 against the M$_1$ receptor in the assay of Example A herein or an assay substantially similar thereto.

2.4 A compound according to Embodiment 2.3 which is a muscarinic M$_1$ receptor agonist having a pEC$_{50}$ in the range from 6.5 to 7.5.

2.5 A compound according to Embodiment 2.3 or Embodiment 2.4 having an E$_{max}$ of at least 95 against the M$_1$ receptor.

2.6 A compound according to any one of Embodiments 1.1 to 1.180 which is a muscarinic M$_4$ receptor agonist having a pEC$_{50}$ in the range from 6.0 to 8.5 and an E$_{max}$ of at least 90 against the M$_4$ receptor in the assay of Example A herein or an assay substantially similar thereto.

2.7 A compound according to Embodiment 2.6 which is a muscarinic M$_4$ receptor agonist having a pEC$_{50}$ in the range from 6.5 to 8.5.

2.8 A compound according to Embodiment 2.6 or Embodiment 2.7 having an E$_{max}$ of at least 95 against the M$_4$ receptor.

2.9 A compound according to any one of Embodiments 2.3 to 2.8 which is selective for the M$_1$ and/or M$_4$ receptor compared to the muscarinic M$_2$ and M$_3$ receptors.

2.10 A compound according to Embodiment 2.9 which is selective for the M$_1$ receptor compared to the muscarinic M$_2$ and M$_3$ receptors.

2.11 A compound according to Embodiment 2.9 which is selective for the M$_4$ receptor compared to the muscarinic M$_2$ and M$_3$ receptors.

2.12 A compound according to any one of Embodiments 2.3 to 2.5 which is selective for the M$_1$ receptor compared to the muscarinic M$_2$, M$_3$ and M$_4$ receptors.

2.13 A compound according to any one of Embodiments 2.6 to 2.8 which is selective for the M$_4$ receptor compared to the muscarinic M$_1$, M$_2$ and M$_3$ receptors.

2.14 A compound according to any one of Embodiments 2.3 to 2.8 which is selective for the M$_1$ and M$_4$ receptor compared to the muscarinic M$_2$ and M$_3$ receptors.

2.15 A compound according to any one of Embodiments 2.3 to 2.14 which has a pEC$_{50}$ of less than 5 and an E$_{max}$ of less than 50 against the muscarinic M$_2$ and M$_3$ receptor subtypes.

2.16 A compound according to Embodiment 2.15 which has a pEC$_{50}$ of less than 4.5 and/or an E$_{max}$ of less than 30 against the muscarinic M$_2$ and M$_3$ receptor subtypes.

2.17 A compound according to any one of Embodiments 1.1 to 1.180 and Embodiments 2.3 to 2.16 for use in the treatment of a disease or condition mediated by the muscarinic M$_1$ receptor.

By virtue of their muscarinic M$_1$ and/or M$_4$ receptor agonist activity, compounds of the invention can be used in the treatment of Alzheimer's disease, schizophrenia and other psychotic disorders, cognitive disorders and other diseases mediated by the muscarinic M$_1$ and/or M$_4$ receptor, and can also be used in the treatment of various types of pain.

Accordingly, in Embodiments 2.18 to 2.34, the invention provides:

2.18 A compound according to any one of Embodiments 1.1 to 1.180 for use in the treatment of a cognitive disorder or psychotic disorder.

2.19 A compound for use in according to Embodiment 2.18 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as Multi-infarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders, epilepsy and schizo-affective disorder.

2.20 A compound according to any one of Embodiments 1.1 to 1.180 for use in the treatment of Alzheimer's disease.

2.21 A compound according to any one of Embodiments 1.1 to 1.180 for use in the treatment of Schizophrenia.

2.22 A compound according to any one of Embodiments 1.1 to 1.180 for use in the treatment of Alzheimer's disease and/or dementia with Lewy bodies.

2.23 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.180.

2.24 A method according to Embodiment 2.20 wherein the cognitive disorder comprises, arises from or is associated with a condition as defined in Embodiment 2.19.

2.25 A method according to Embodiment 2.24 wherein the cognitive disorder arises from or is associated with Alzheimer's disease.
2.26 A method according to Embodiment 2.24 wherein the cognitive disorder is Schizophrenia.
2.27 The use of a compound according to any one of Embodiments 1.1 to 1.180 for the manufacture of a medicament for the treatment of a cognitive disorder.
2.28 The use according to Embodiment 2.27 wherein the cognitive disorder comprises, arises from or is associated with a condition as defined in Embodiment 2.11.
2.29 The use according to Embodiment 2.28 wherein the cognitive disorder arises from or is associated with Alzheimer's disease.
2.30 The use according to Embodiment 2.28 wherein the cognitive disorder is Schizophrenia.
2.31 A compound according to any one of Embodiments 1.1 to 1.180 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.
2.32 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain, which method comprises the administration of a therapeutically effective dose of a compound according to any one of Embodiments 1.1 to 1.180.
2.33 A compound according to any one of Embodiments 1.1 to 1.180 for the treatment of peripheral disorders such as reduction of intra ocular pressure in Glaucoma and treatment of dry eyes and dry mouth including Sjogren's Syndrome.
2.34 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.180.
2.35 The use of a compound according to any one of Embodiments 1.1 to 1.180 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain or for the treatment of peripheral disorders such as reduction of intra ocular pressure in Glaucoma and treatment of dry eyes and dry mouth including Sjogren's Syndrome.
2.36 The use of a compound according to any one of Embodiments 1.1 to 1.180 for the treatment of addicition.
2.37 The use of a compound according to any one of Embodiments 1.1 to 1.180 for the treatment of movement disorders such as Parkinson's disease, ADHD, Huntingdon's disease, tourette's syndrome and other syndromes associated with dopaminergic dysfunction as an underlying pathogenetic factor driving disease.

Methods for the Preparation of Compounds of the Formula (1) and Formula (1a)

Compounds of the formula (1) and formula (1a) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.180, which process comprises:

(A) the Reaction of a Compound of the Formula (10)

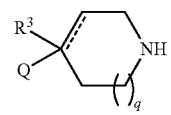

(10)

with a compound of the formula (11) or (11a):

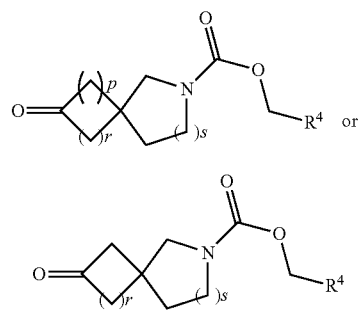

(11a)

(11)

under reductive amination conditions; wherein p, q, r, s, $R^3$, $R^4$ and Q are as defined in any one of Embodiments 1.1 to 1.180; or (B) the reaction of a compound of the formula (12) or (12a):

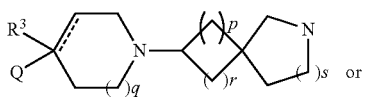

(12a)

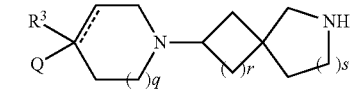

(12)

compound of the formula Cl—C(=O)—CH$_2$—R$^4$, in the presence of a base; or (C) the reaction of a compound of the formula (10)

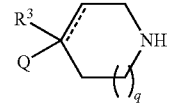

(10)

with a compound of the formula (13) or (13a):

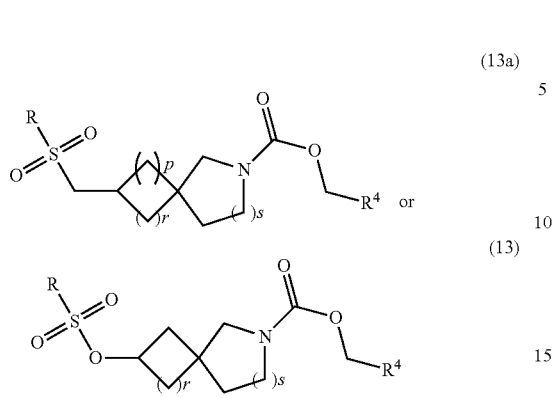

under nucleophilic substitution conditions; wherein p, q, r, s, R³, R⁴ and Q are as defined in any one of Embodiments 1.1 to 1.180; and optionally:

(D) converting one compound of the formula (1) or formula (1a) to another compound of the formula (1) or formula (1a) respectively.

In process variant (A), the piperidine heterocycle (10) is reacted with the substituted ketone (11) or (11a) under reductive amination conditions. The reductive amination reaction is typically carried out at ambient temperature using a borohydride reducing agent such as sodium triacetoxyborohydride in a solvent such as dichloromethane or dichloroethane containing acetic acid.

In process variant (C), the piperidine heterocycle (10) is reacted with the sulfonic ester (13 or 13a, R=methyl, trifluoromethyl or 4-methylphenyl) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide.

Intermediate compounds of the formula (12) and (12a) can be prepared by the series of reactions shown in Scheme 1 and Scheme 1a respectively below.

Scheme 1a

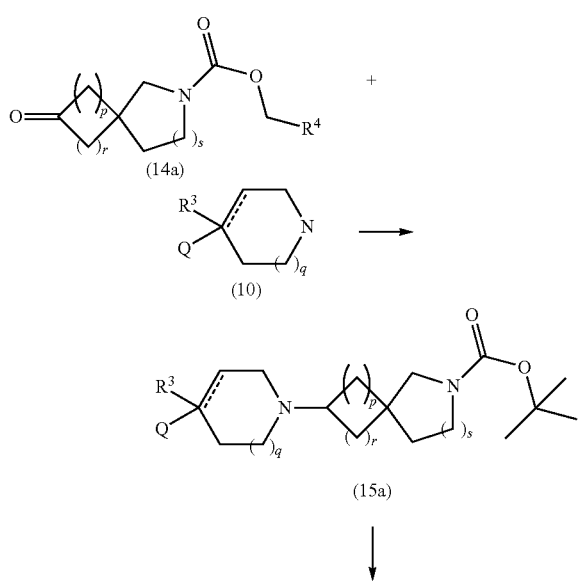

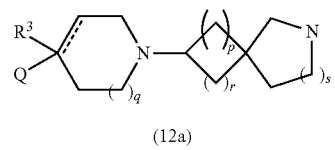

(12a)

Scheme 1

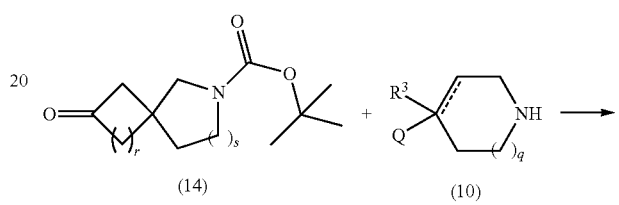

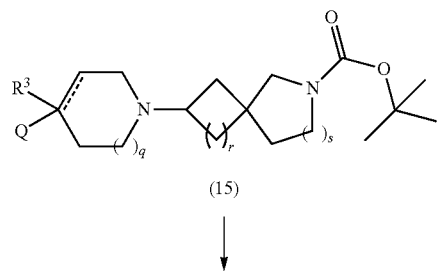

(15)

↓

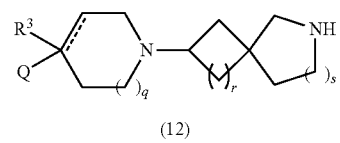

(12)

In reaction Scheme 1 or Scheme 1a, the piperidine heterocycle (10) is reacted with the Boc-protected spiroketone (14) or (14a) respectively under reductive amination conditions. The reductive amination reaction is typically carried out with mild heating (e.g. to a temperature of from about 40° C. to about 70° C.) in the presence of either sodium cyanoborohydride in combination with zinc chloride or sodium triacetoxyborohydride in combination with titanium isopropoxide in a solvent such as dichloromethane or dichloroethane containing acetic acid to give an intermediate piperidine compound (15) or (15a) which is then deprotected by removal of the Boc group by treatment with acid (e.g. trifluoroacetic acid in dichloromethane) to give the compound (12) or (12a) respectively.

Compounds of the formula (12) and (12a) can also be prepared by the sequence of reactions shown in Scheme 2 and Scheme 2a respectively below.

Scheme 2a

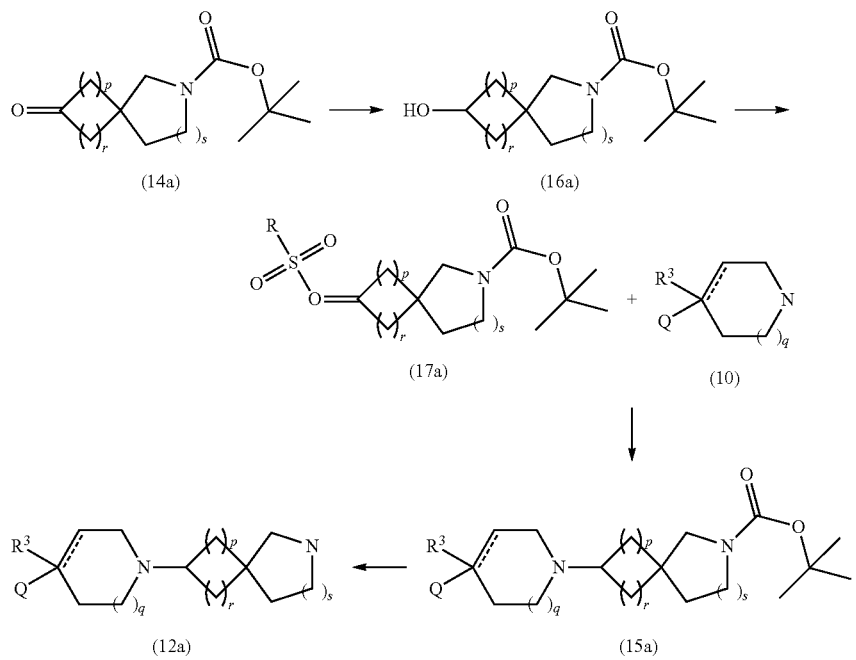

Scheme 2

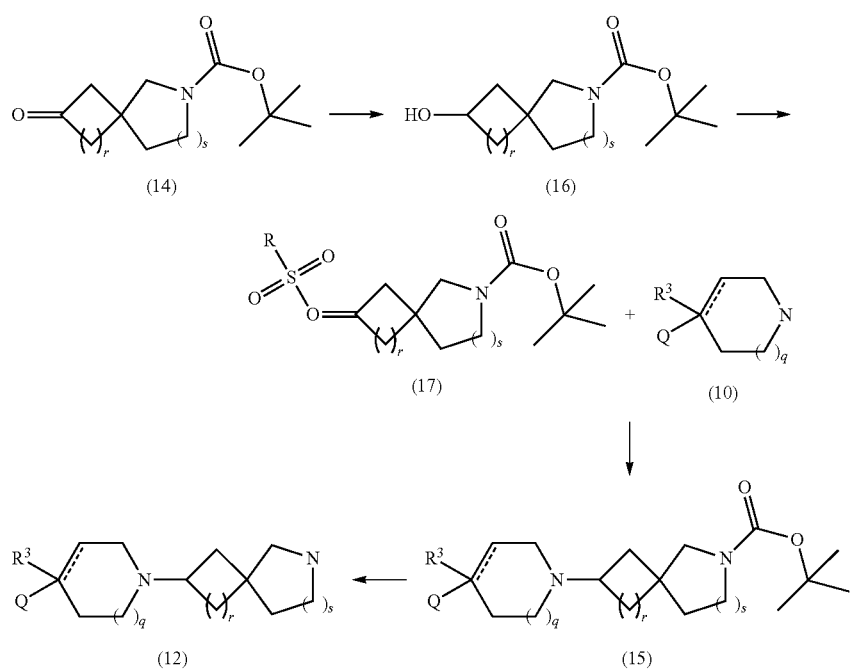

In Scheme 2 or Scheme 2a, the Boc-protected spiroketone (14) or (14a) respectively is reduced to the alcohol (16) or (16a) respectively using sodium borohydride in methanol. The alcohol (16) or (16a) is then activated as the sulfonic ester (17 or 17a respectively, R=methyl, trifluoromethyl or 4-methylphenyl) using the corresponding sulfonyl chloride in dichloromethane in the presence of a tertiary amine such as triethylamine or N,N-diisopropylethylamine. The sulfonic ester (17) or (17a) is reacted with the piperidine heterocycle (10) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide to give compound (15) or (15a) respectively which is then deprotected by removal of the Boc group by treatment with acid (e.g. trifluoroacetic acid in dichloromethane) to give the compound (12) or (12a) respectively.

Once formed, one compound of the formula (1) or formula (1a), or a protected derivative thereof, can be converted into another compound of the formula (1) or formula (1a) respectively by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2). Examples of these transformations include amide bond formation, urea formation, carbamate formation, alkylation reactions, N-arylation reaction and C—C bond coupling reactions.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) or formula (1a) as defined in any one of Embodiments 1.1 to 1.180 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) or formula (1a) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) or formula (1a) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

BRIEF DESCRIPTION OF DRAWINGS

FIG. 1 shows the locomotor activity observed in the hyperactivity test of Example B.

EXAMPLES

The invention will now be illustrated, but not limited, by reference to the specific embodiments described in the following examples.

Examples 1-1 to 3-3

The compounds of Examples 1-1 to 3-3 shown in Table 1 below have been prepared. Their NMR and LCMS properties and the methods used to prepare them are set out in Table 3.

TABLE 1

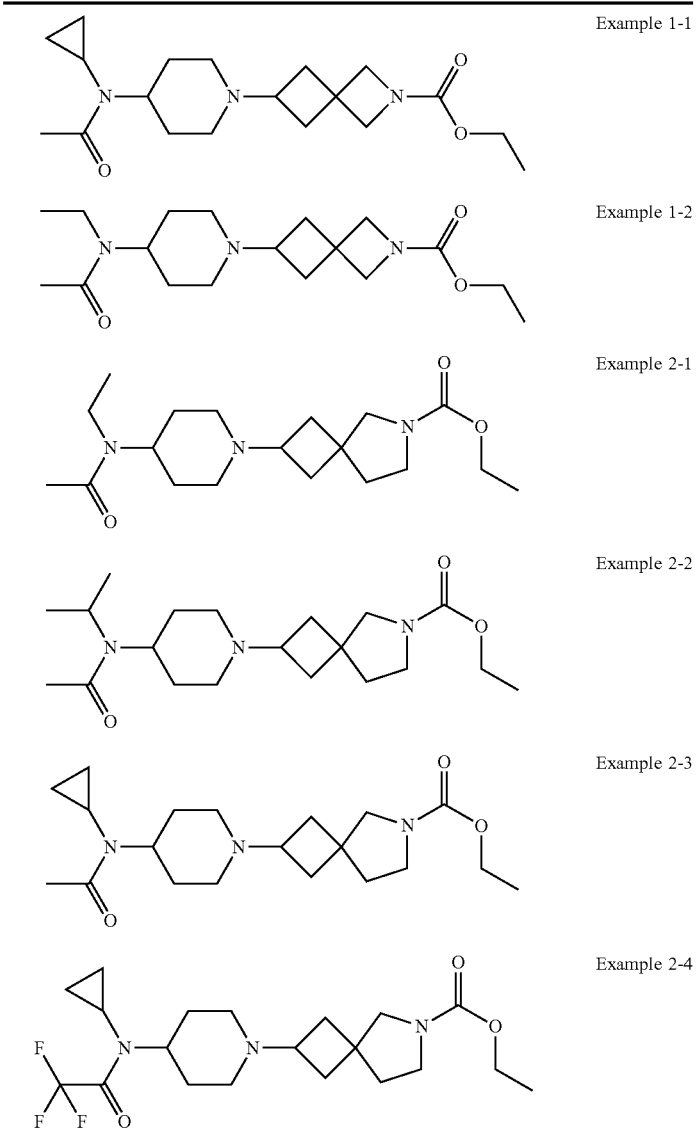

TABLE 1-continued
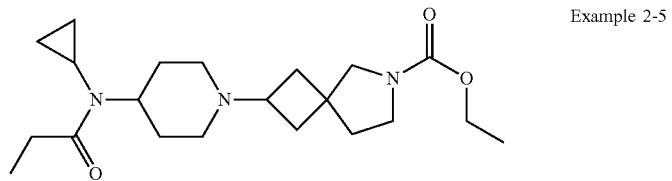
Example 2-5
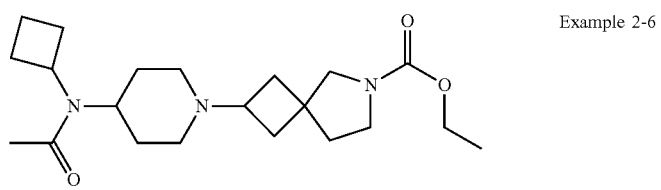
Example 2-6
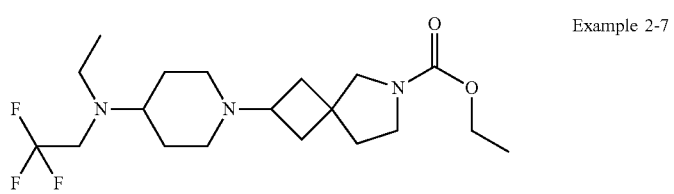
Example 2-7
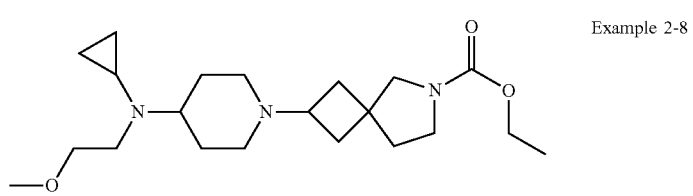
Example 2-8
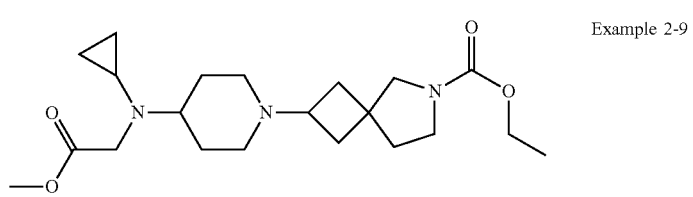
Example 2-9
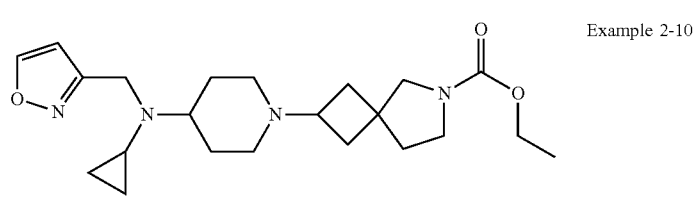
Example 2-10
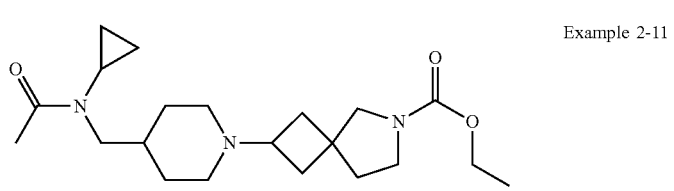
Example 2-11
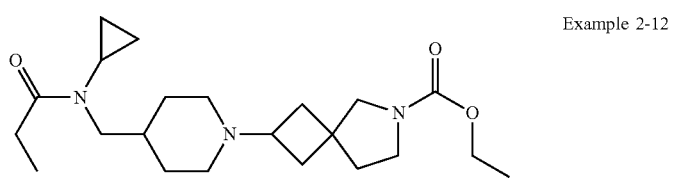
Example 2-12

TABLE 1-continued
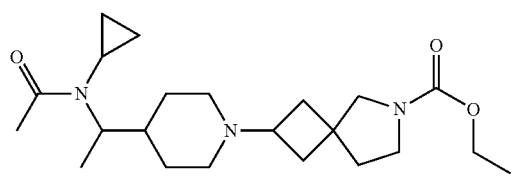 [SMILES: CCOC(=O)N1CCC2(CC(N3CCC(C(C)N(C(C)=O)C4CC4)CC3)C2)C1] Example 2-13
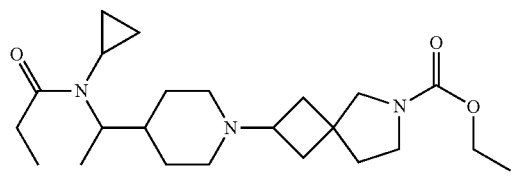 [SMILES: CCOC(=O)N1CCC2(CC(N3CCC(C(C)N(C(=O)CC)C4CC4)CC3)C2)C1] Example 2-14
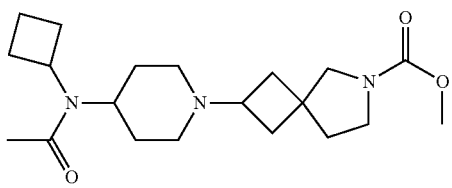 [SMILES: COC(=O)N1CCC2(CC(N3CCC(N(C(C)=O)C4CCC4)CC3)C2)C1] Example 2-15
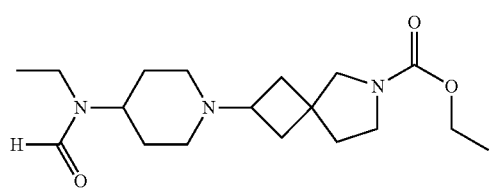 [SMILES: CCOC(=O)N1CCC2(CC(N3CCC(N(C=O)CC)CC3)C2)C1] Example 2-16
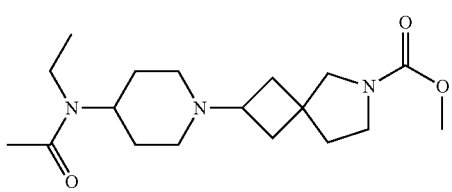 [SMILES: CCN(C(C)=O)C1CCN(C2CC3(CCN(C(=O)OC)C3)C2)CC1] Example 2-17
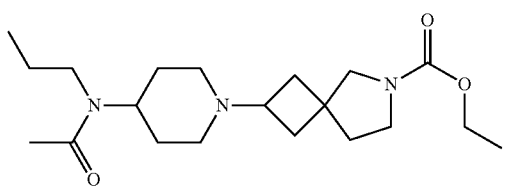 [SMILES: CCCN(C(C)=O)C1CCN(C2CC3(CCN(C(=O)OCC)C3)C2)CC1] Example 2-18
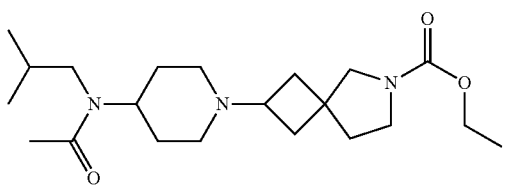 [SMILES: CCOC(=O)N1CCC2(CC(N3CCC(N(CC(C)C)C(C)=O)CC3)C2)C1] Example 2-19
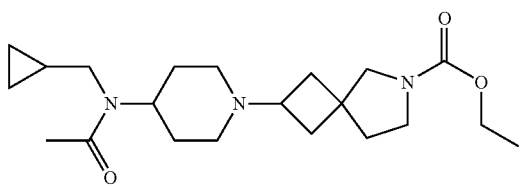 [SMILES: CCOC(=O)N1CCC2(CC(N3CCC(N(CC4CC4)C(C)=O)CC3)C2)C1] Example 2-20

TABLE 1-continued
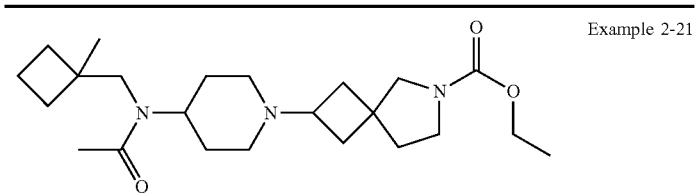 Example 2-21
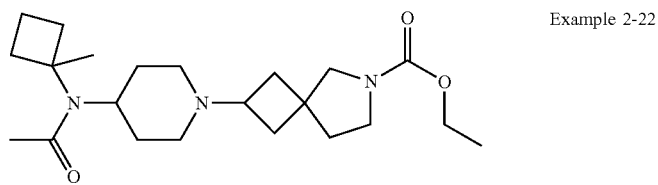 Example 2-22
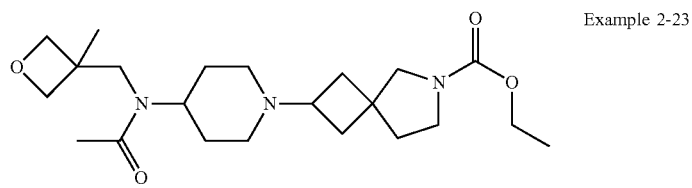 Example 2-23
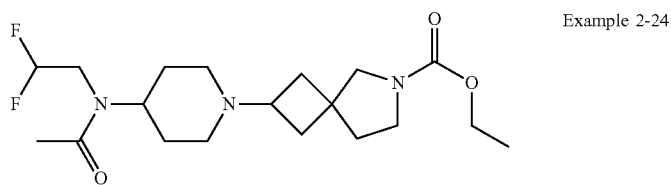 Example 2-24
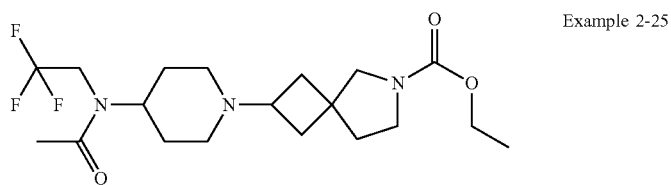 Example 2-25
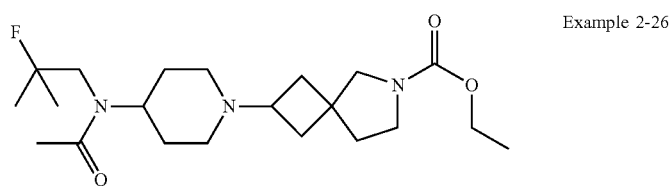 Example 2-26
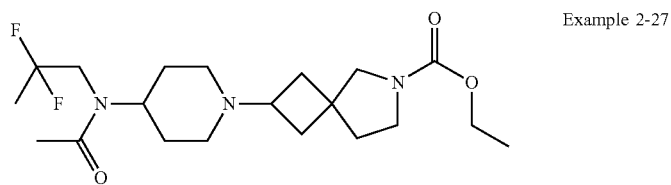 Example 2-27
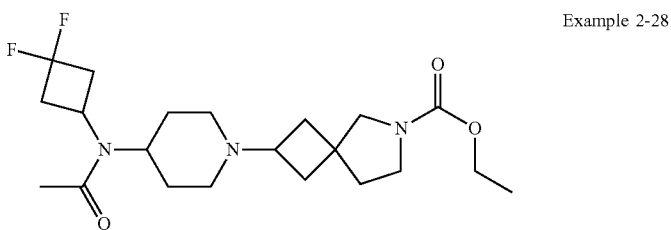 Example 2-28

TABLE 1-continued
| | |
|---|---|
| 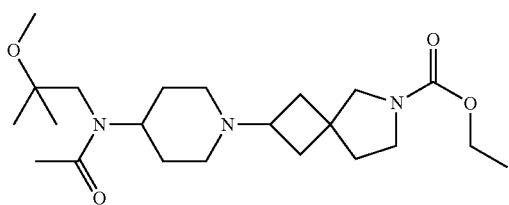 [SMILES: CCOC(=O)N1CCC2(CC(N3CCC(N(CC(C)(C)OC)C(C)=O)CC3)C2)C1] | Example 2-29 |
| 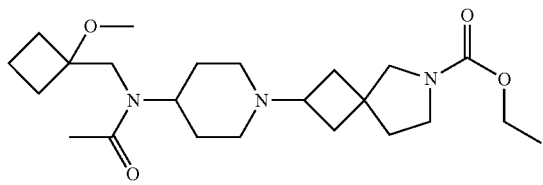 [SMILES: CCOC(=O)N1CCC2(CC(N3CCC(N(CC4(OC)CCC4)C(C)=O)CC3)C2)C1] | Example 2-30 |
| 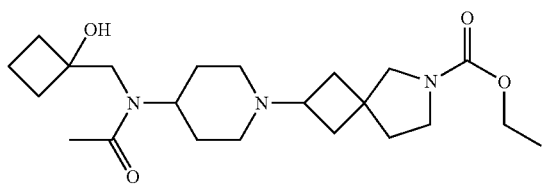 [SMILES: CCOC(=O)N1CCC2(CC(N3CCC(N(CC4(O)CCC4)C(C)=O)CC3)C2)C1] | Example 2-31 |
| 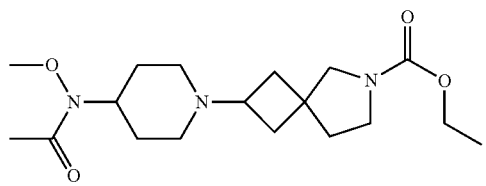 [SMILES: CCOC(=O)N1CCC2(CC(N3CCC(N(OC)C(C)=O)CC3)C2)C1] | Example 2-32 |
| 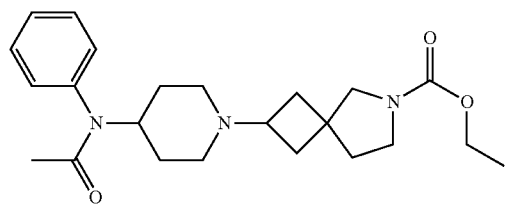 [SMILES: CCOC(=O)N1CCC2(CC(N3CCC(N(C(C)=O)c4ccccc4)CC3)C2)C1] | Example 2-33 |
| 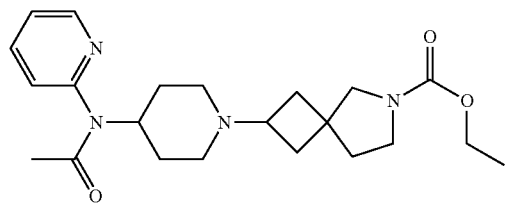 [SMILES: CCOC(=O)N1CCC2(CC(N3CCC(N(C(C)=O)c4ccccn4)CC3)C2)C1] | Example 2-34 |
| 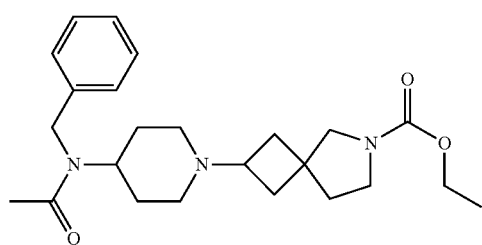 [SMILES: CCOC(=O)N1CCC2(CC(N3CCC(N(Cc4ccccc4)C(C)=O)CC3)C2)C1] | Example 2-35 |

TABLE 1-continued
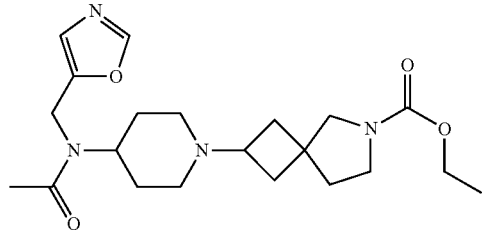 [SMILES: CCOC(=O)N1CCC2(CC(N3CCC(N(Cc4cnco4)C(C)=O)CC3)C2)C1]
Example 2-36
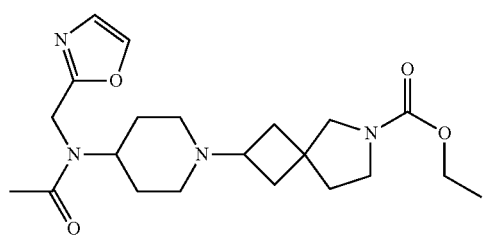 [SMILES: CCOC(=O)N1CCC2(CC(N3CCC(N(Cc4ncco4)C(C)=O)CC3)C2)C1]
Example 2-37
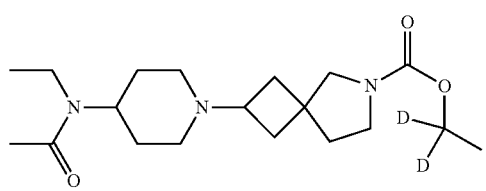 [SMILES: [2H]C([2H])(C)OC(=O)N1CCC2(CC(N3CCC(N(CC)C(C)=O)CC3)C2)C1]
Example 2-38
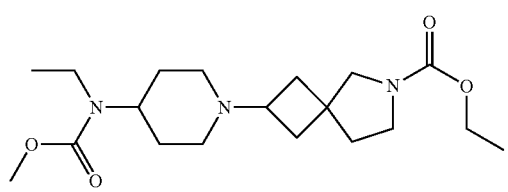 [SMILES: CCOC(=O)N1CCC2(CC(N3CCC(N(CC)C(=O)OC)CC3)C2)C1]
Example 2-39
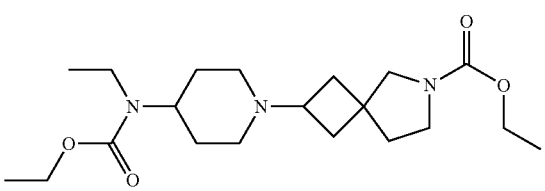 [SMILES: CCOC(=O)N1CCC2(CC(N3CCC(N(CC)C(=O)OCC)CC3)C2)C1]
Example 2-40
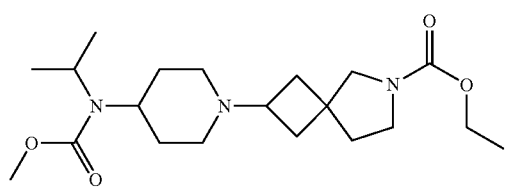 [SMILES: CCOC(=O)N1CCC2(CC(N3CCC(N(C(=O)OC)C(C)C)CC3)C2)C1]
Example 2-41
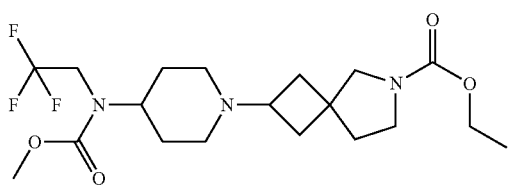 [SMILES: CCOC(=O)N1CCC2(CC(N3CCC(N(CC(F)(F)F)C(=O)OC)CC3)C2)C1]
Example 2-42

TABLE 1-continued
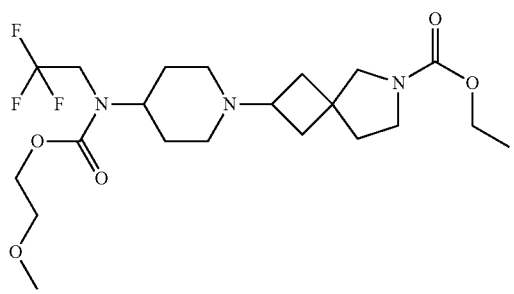 [SMILES: CCOC(=O)N1CCC2(CC(N3CCC(N(CC(F)(F)F)C(=O)OCCOC)CC3)C2)C1] Example 2-43
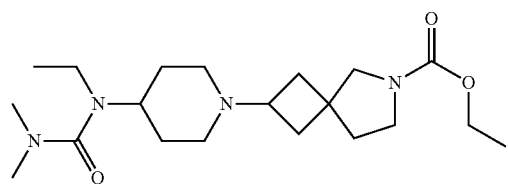 [SMILES: CCOC(=O)N1CCC2(CC(N3CCC(N(CC)C(=O)N(C)C)CC3)C2)C1] Example 2-44
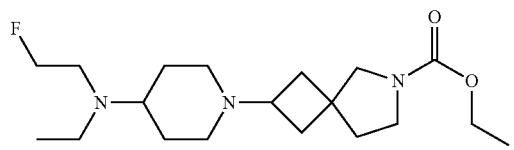 [SMILES: CCOC(=O)N1CCC2(CC(N3CCC(N(CC)CCF)CC3)C2)C1] Example 2-45
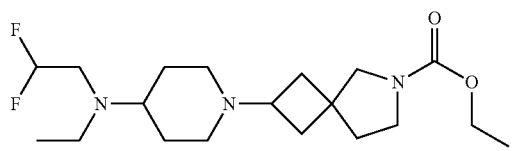 [SMILES: CCOC(=O)N1CCC2(CC(N3CCC(N(CC)CC(F)F)CC3)C2)C1] Example 2-46
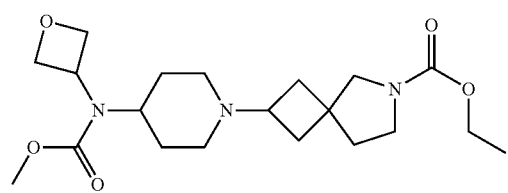 [SMILES: CCOC(=O)N1CCC2(CC(N3CCC(N(C(=O)OC)C4COC4)CC3)C2)C1] Example 2-47
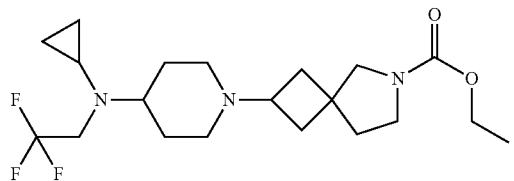 [SMILES: CCOC(=O)N1CCC2(CC(N3CCC(N(CC(F)(F)F)C4CC4)CC3)C2)C1] Example 2-48
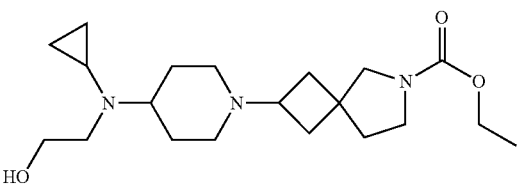 [SMILES: CCOC(=O)N1CCC2(CC(N3CCC(N(CCO)C4CC4)CC3)C2)C1] Example 2-49
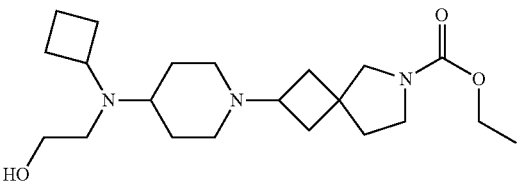 [SMILES: CCOC(=O)N1CCC2(CC(N3CCC(N(CCO)C4CCC4)CC3)C2)C1] Example 2-50

TABLE 1-continued
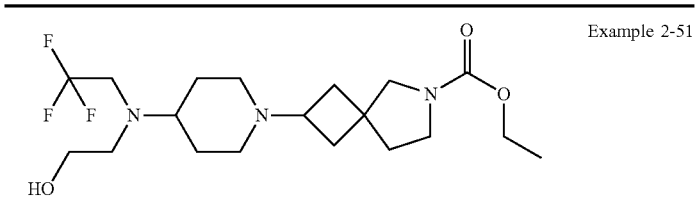 Example 2-51
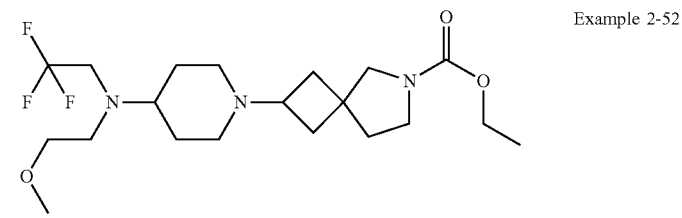 Example 2-52
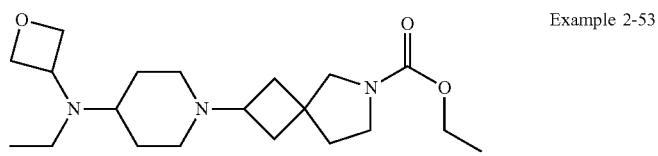 Example 2-53
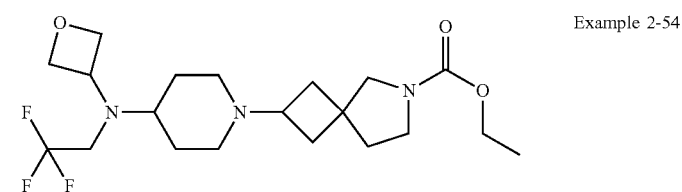 Example 2-54
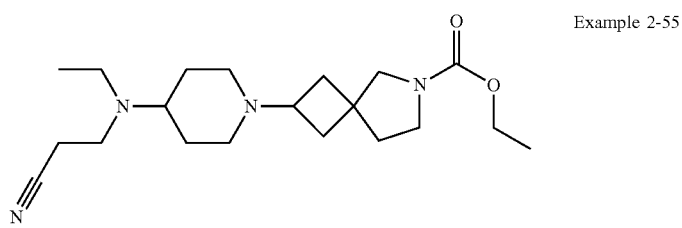 Example 2-55
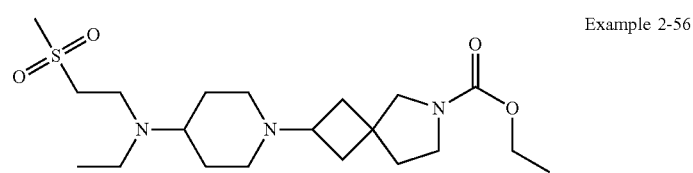 Example 2-56
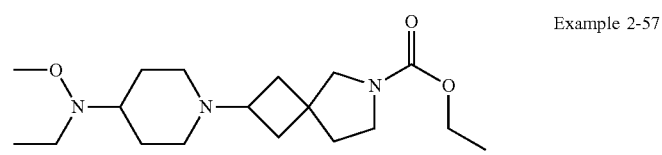 Example 2-57
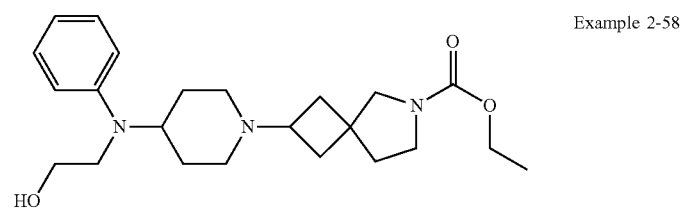 Example 2-58

TABLE 1-continued
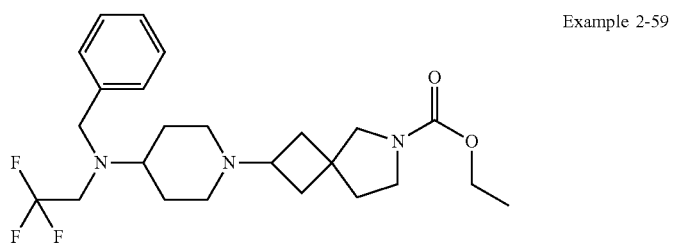 Example 2-59
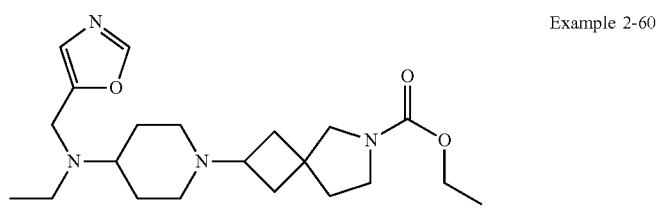 Example 2-60
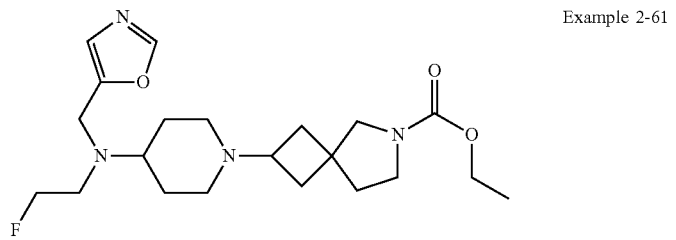 Example 2-61
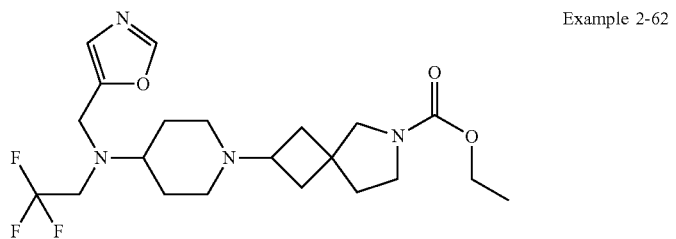 Example 2-62
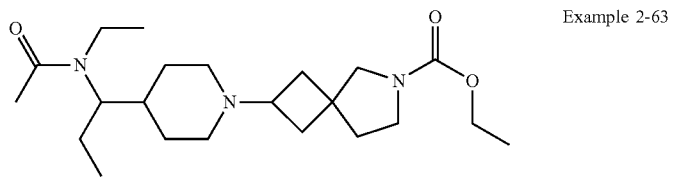 Example 2-63
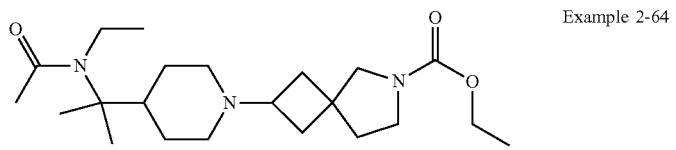 Example 2-64
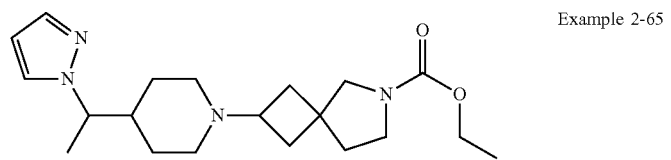 Example 2-65

TABLE 1-continued

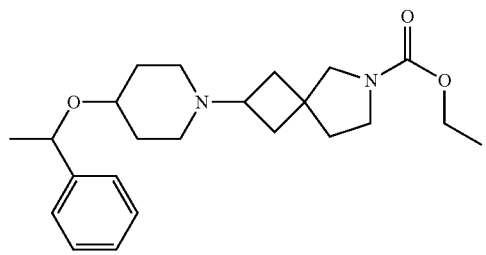 [SMILES: CCOC(=O)N1CCC2(CC(N3CCC(OC(C)c4ccccc4)CC3)C2)C1]

Example 2-66

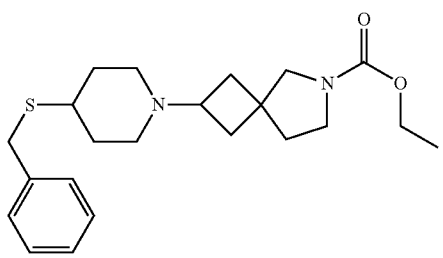 [SMILES: CCOC(=O)N1CCC2(CC(N3CCC(SCc4ccccc4)CC3)C2)C1]

Example 2-67

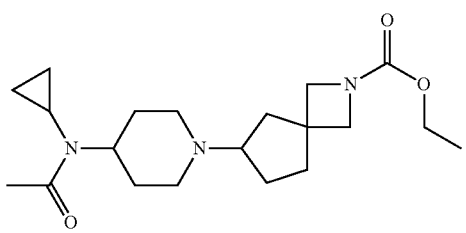 [SMILES: CCOC(=O)N1CC2(CCC(N3CCC(N(C(C)=O)C4CC4)CC3)C2)C1]

Example 3-1

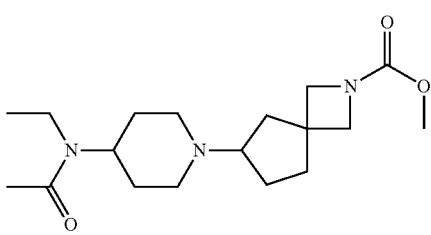 [SMILES: CCN(C(C)=O)C1CCN(C2CCC3(C2)CN(C(=O)OC)C3)CC1]

Example 3-2

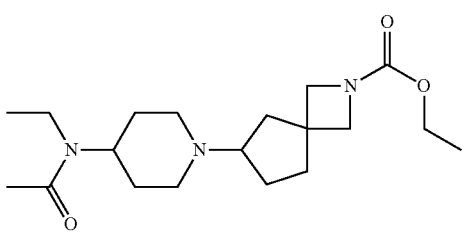 [SMILES: CCOC(=O)N1CC2(CCC(N3CCC(N(CC)C(C)=O)CC3)C2)C1]

Example 3-3

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ:)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and Silica gel F254 (Merck) as a stationary phase. Microwave-mediated reactions were performed in Biotage Initiator or CEM Discover microwave reactors.

LCMS experiments were typically carried out using electrospray conditions as specified for each compound under the following conditions:

LCMS Method C

Instruments: Agilent 1260 Infinity LC with Diode Array Detector, Agilent 6120B Single Quadrupole MS with API-ES Source; Column: Phenomenex Gemini-NX C-18, 3 micron, 2.0×30 mm; Gradient [time (min)/solvent B in A (%)]: Method: 0.00/5, 2.00/95, 2.50/95, 2.60/5, 3.00/5; Solvents: solvent A=2.5 L H$_2$O+2.5 mL of (28% NH$_3$ in H₂O); solvent B=2.5 L MeCN+129 mL H₂O+2.7 mL of (28% NH₃ in H₂O); Injection volume 0.5 µL; UV detection 190 to 400 nM; column temperature 40° C.; Flow rate 1.5 mL/min.

LCMS Methods D and E

Instruments: HP 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method D: 0.00/2, 0.10/2, 2.50/95, 3.50/95 or Method E: 0.00/2, 0.10/2, 8.40/95, 10.00/95; Solvents: solvent C=2.5 L H₂O+2.5 mL 28% ammonia in H₂O solution; solvent D=2.5 L MeCN+ 135 mL H₂O+2.5 mL 28% ammonia in H₂O solution); Injection volume 1 µL; UV detection 230 to 400 nM; Mass detection 130 to 800 AMU (+ve and −ve electrospray); column temperature 45° C.; Flow rate 1.5 mL/min.

LCMS Method F

Instruments: Waters Acquity H Class, Photo Diode Array, SQ Detector; Column: BEH C18, 1.7 micron, 2.1×50 mm; Gradient [time (min)/solvent B in A (%)]: 0.00/5, 0.40/5, 0.8/35, 1.20/55, 2.50/100, 3.30/100 4.00/5; Solvents: solvent A=5 mM mmonium acetate and 0.1% formic acid in H₂O; solvent B=0.1% formic acid in MeCN; Injection volume 2 µL; UV detection 200 to 400 nM; Mass detection 100 to 1200 AMU (+ve electrospray); column at ambient temperature; Flow rate 0.5 mL/min.

LCMS Method H

Instruments: Waters 2695, Photo Diode Array, ZQ-2000 Detector; Column: X-Bridge C18, 5 micron, 150×4.6 mm; Gradient [time (min)/solvent B in A (%)]: 0.00/100, 7.00/50, 9.00/0, 11.00/0, 11.01/100, 12.00/100; Solvents: solvent A=0.1% ammonia in H₂O; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

LCMS Method I

Instruments: Waters 2695, Photo Diode Array, ZQ-2000 Detector; Column: X-Bridge C18, 3.5 micron, 150×4.6 mm; Gradient [time (min)/solvent B in A (%)]: 0.00/5, 5.00/90, 5.80/95, 10/95; Solvents: solvent A=0.1% ammonia in H₂O; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

LCMS Method K

Instruments: Waters 2695, Photo Diode Array, ZQ-2000 Detector; Column: X-Bridge C18, 3.5 micron, 50×4.6 mm; Gradient [time (min)/solvent B in A (%)]: 0.01/0, 0.20/0, 5.00/90, 5.80/95, 7.20/95, 7.21/100, 10.00/100; Solvents: solvent A=0.1% ammonia in H₂O; solvent B=0.1% ammonia in MeCN; Injection volume 10 µL; UV detection 200 to 400 nM; Mass detection 60 to 1000 AMU (+ve electrospray); column at ambient temperature; Flow rate 1.0 mL/min.

LCMS data in the experimental section are given in the format: Mass ion, retention time, UV activity.

Abbreviations

AcOH=acetic acid
CDI=1,1'-Carbonyldiimidazole
d=day(s)
DAST=diethylaminosulfur trifluoride
DCE=dichloroethane
DCM=dichloromethane
DIPEA=diisopropylethylamine
DIAD=diisopropyl azodicarboxylate
DMF=dimethylformamide
DMP=Dess-Martin periodinane
DMSO=dimethylsulfoxide
ES=electro spray ionisation
EtOAc=ethyl acetate
h=hour(s)
HATU=1-[Bis(dimethylamino)methylene]-1H-1,2,3-triazolo[4,5-b]pyridinium 3-oxid hexafluorophosphate
HPLC=high performance liquid chromatography
LC=liquid chromatography
LiAlH₄/LAH=Lithium aluminium hydride
MeCN=acetonitrile
MeOH=methanol
min=minute(s)
MS=mass spectrometry
Et₃N=triethylamine
NMR=nuclear magnetic resonance
rt=room temperature
sat.=saturated
sol.=solution
STAB=sodium triacetoxyborohydride
THF=tetrahydrofuran
TLC=thin layer chromatography Prefixes n-, s-, i-, t- and tert- have their usual meanings: normal, secondary, iso, and tertiary.

Final compounds are named using the software package ACD/ChemSketch Version 12. Intermediates and reagents are named either using the software package ACD/ChemSketch Version 12 or are referred to using their common name as typically found in suppliers catalogues etc.

General Synthetic Procedures for the Intermediates

Route 1

Procedure for the Preparation of Intermediate 4, ethyl 2-oxo-6-azaspiro[3.4]octane-6-carboxylate

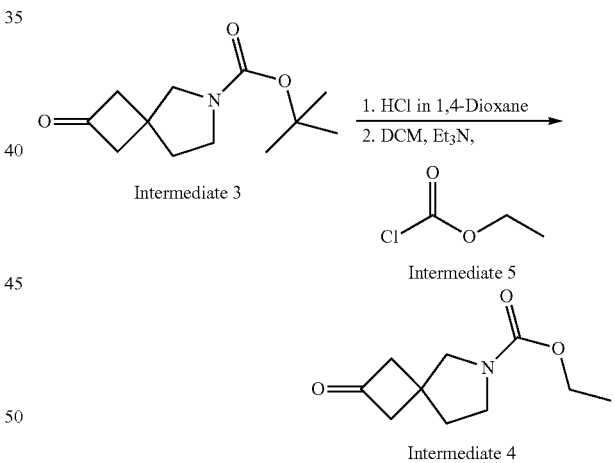

Intermediate 3, tert-butyl 2-oxo-6-azaspiro[3.4]octane-6-carboxylate (3.37 g, 15 mmol) was added portionwise to hydrogen chloride (4 M dioxane solution, 50 mL, 200 mmol). Caution: effervescence. After 24 h, the reaction was concentrated in vacuo and the residual solid was dissolved in a mixture of Et₃N (4.18 mL, 30 mmol) and DCM (66 mL). On completion of dissolution, the solution was immediately cooled to 0° C., then Intermediate 5, ethyl carbonochloridate (1.57 mL, 16 mmol) was added dropwise. After 18 h, the mixture was poured into DCM (100 mL) and NaHCO₃ (aq) (100 mL) and extracted with DCM (2×100 mL). The organic layers were collected, washed with brine (20 mL), dried over MgSO₄, then the residue after evaporation was purified by column chromatography (normal phase, [Biotage SNAP cartridge KP-sil 100 g, 40-63 μm, 60 Å, 50 mL per min, gradient 0% to 4% MeOH in DCM]) to give Intermediate 4, ethyl 2-oxo-6-azaspiro[3.4]octane-6-carboxylate as an oil (2.47 g, 83%).

The data for the title compound are in Table 2.

Route 2

Typical Procedure for the Preparation of Amines, as Exemplified by the Preparation of Intermediate 2, N-ethyl-N-(piperidin-4-yl)acetamide hydrochloride

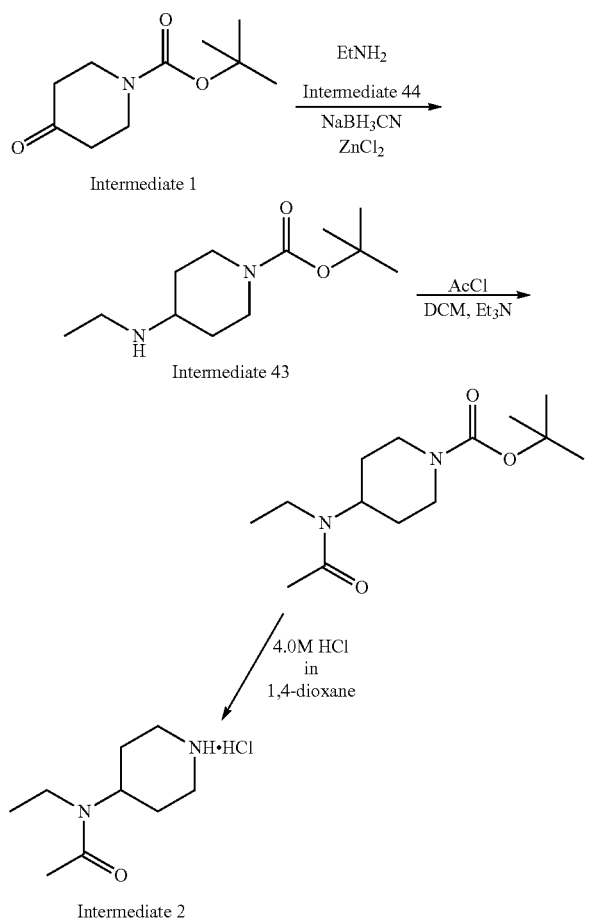

To Intermediate 1, tert-butyl 4-oxopiperidine-1-carboxylate (3.0 g, 15.1 mmol) in MeOH (40 mL) was added Intermediate 44, ethanamine (12.6 mL, 25.1 mmol, 2 M in THF), Et₃N (4.2 mL, 30.3 mmol) and ZnCl₂ (0.1 g, 0.7 mmol) and the reaction mixture was stirred at 60° C. for 7 h. NaBH₃CN (1.2 g, 19.6 mmol) was added portionwise and the resulting reaction mixture was stirred at 25° C. for 17 h. The solvents were removed in vacuo and the residue was partitioned between H₂O (250 mL) and EtOAc (200 mL). The aqueous layer was further extracted with EtOAc (2×200 mL), and the combined organic phases were dried (Na₂SO₄) and the solvent was removed in vacuo. The residue was purified by column chromatography (normal basic activated alumina, 10 to 30% EtOAc in hexane) to give Intermediate 43, tert-butyl 4-(ethylamino)piperidine-1-carboxylate (3.0 g, 88%) as a gum.

The data for Intermediate 43 are in Table 2.

To Intermediate 43, tert-butyl 4-(ethylamino)piperidine-1-carboxylate (0.20 g, 0.9 mmol) in DCM (10 mL) was added triethylamine (0.15 mL, 1.1 mmol) dropwise and the mixture was stirred at 0° C. for 30 min. Acetyl chloride (0.09 g, 1.1 mmol) was added dropwise at 0° C. and the resulting reaction mixture was stirred at 25° C. for 8 h before removal of the solvents in vacuo. The residue was partitioned between H₂O (120 mL) and EtOAc (100 mL) and the aqueous layer was further extracted with EtOAc (2×100 mL). The combined organic phases were dried (Na₂SO₄) and the solvent removed in vacuo. The residue was purified by column chromatography (normal basic activated alumina, 0.5 to 1.0% MeOH in DCM) to give tert-butyl 4-[acetyl(ethyl)amino]piperidine-1-carboxylate (0.15 g, 63%) as a liquid.

LCMS (Method I): m/z 271 [M+H]⁺ (ES⁺), at 3.79 min, UV active.

To tert-butyl 4-[acetyl(ethyl)amino]piperidine-1-carboxylate (0.20 g, 0.7 mmol) in 1,4-dioxane (5 mL) was added 4.0 M HCl in 1,4-dioxane (5 mL) dropwise and the resulting reaction mixture was stirred at 25° C. for 16 h. The solvent was removed in vacuo and the residue was purified by triturating with diethyl ether (3×5 mL) to give Intermediate 2, N-ethyl-N-(piperidin-4-yl)acetamide hydrochloride salt (0.15 g, 100%) as a solid.

The data for the title compound is in Table 2.

Route 3

Typical Procedure for the Preparation of Amines, as Exemplified by the Preparation of Intermediate 8, N-cyclopropyl-N-(piperidin-4-yl) acetamide

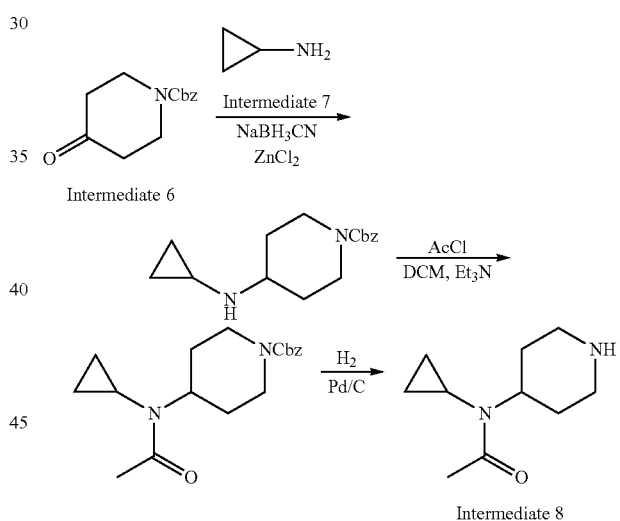

Intermediate 7, cyclopropanamine (1.2 g, 21.5 mmol), Intermediate 6, benzyl 4-oxopiperidine-1-carboxylate (5.0 g, 21.5 mmol), and zinc chloride (0.15 g, 1.1 mmol) were dissolved in MeOH (15 mL) and heated to 50-60° C. for 3 h under N₂. The mixture was then cooled to 0-10° C. before portionwise addition of NaCNBH₃ (1.8 g, 27.9 mmol) and further stirring at rt for 2 h. The reaction mixture was partitioned between H₂O (15 mL) and EtOAc (25 mL) and the aqueous layer was further extracted with EtOAc (2×25 mL). The combined organic phases were dried (Na₂SO₄) and the solvent was removed in vacuo to yield benzyl 4-(cyclopropylamino)piperidine-1-carboxylate (4.0 g, 68%) as a gum.

LCMS (Method F): m/z 275 [M+H]⁺ (ES⁺), at 1.60 min, UV active

To benzyl 4-(cyclopropylamino)piperidine-1-carboxylate (2.5 g, 9.1 mmol) in DCM (10 mL) cooled to 0-5° C. was added Et₃N (1.8 g, 18.2 mmol) and acetyl chloride (0.9 g, 11.9 mmol) dropwise and the reaction mixture was stirred at 25° C. for 16 h. The reaction mixture was partitioned between H₂O (15 mL) and DCM (25 mL) and the aqueous layer was further extracted with DCM (2×25 mL). The combined organic phases were dried (Na₂SO₄) and the solvent was removed in vacuo to yield benzyl 4-[acetyl (cyclopropyl)amino]piperidine-1-carboxylate (2.0 g, 70%) as a gum, which was used in the next step without further purification.

LCMS (Method I): m/z 317 [M+H]⁺ (ES⁺), at 4.17 min, UV active

To benzyl 4-[acetyl(cyclopropyl)amino]piperidine-1-carboxylate (2.0 g, 6.3 mmol) in MeOH (15 mL) was added 10% Pd/C (0.2 g) at rt and the reaction mixture was stirred under an atmosphere H₂ gas (10 kg pressure) for 16 h at rt. The reaction mixture was then filtered through Celite and the solvent was removed from the filtrate in vacuo to yield Intermediate 8, N-cyclopropyl-N-(piperidin-4-yl) acetamide (1.0 g, 86%) as a gum, which was used in the next step without further purification.

The data for the title compound are in Table 2.

Route 4

Typical Procedure for the Preparation of Amines Substituted with a Pendant Ester, as Exemplified by the Preparation of Intermediate 13, methyl [cyclopropyl(piperidin-4-yl)amino] acetate hydrochloride

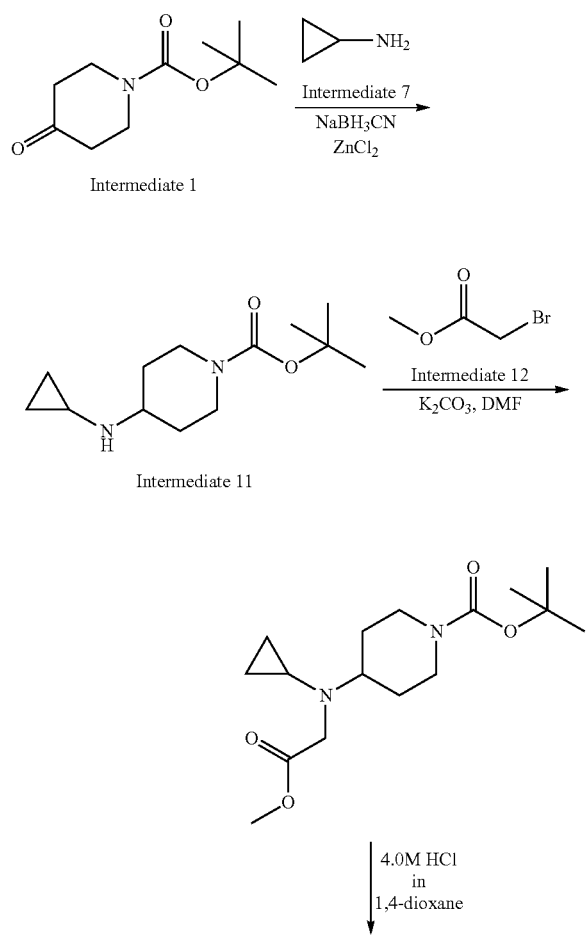

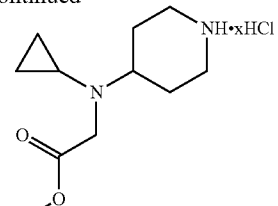

Intermediate 13

To Intermediate 1, tert-butyl 4-oxopiperidine-1-carboxylate (5.0 g, 25.1 mmol) in MeOH (40 mL) was added Intermediate 7, cyclopropanamine (1.4 g, 25.1 mmol), Et₃N (10.0 mL, 75.3 mmol) and ZnCl₂ (0.3 g, 2.5 mmol). The reaction mixture was stirred at 60° C. for 7 h, then NaBH₃CN (4.8 g, 75.3 mmol) was added portionwise. The resulting reaction mixture was stirred at 25° C. for 17 h. The solvents were removed in vacuo, and the residue was partitioned between H₂O (250 mL) and EtOAc (200 mL). The aqueous layer was extracted further with EtOAc (2×200 mL), the combined organic layers were dried (Na₂SO₄) and the solvent was removed in vacuo. The residue was purified by column chromatography (normal basic activated alumina, 10% to 30% EtOAc in hexane) to give Intermediate 11, tert-butyl 4-(cyclopropylamino)piperidine-1-carboxylate (5.3 g, 88%) as a gum.

The data for Intermediate 11 are in Table 2.

Intermediate 11, tert-butyl 4-(cyclopropylamino)piperidine-1-carboxylate (300 mg, 1.25 mmol) was dissolved in DMF (10 mL) and K₂CO₃ (517 mg, 3.75 mmol) was added. The reaction mixture was stirred at 70° C. for 3 h, then Intermediate 12, methyl bromoacetate (229 mg, 1.50 mmol) was added dropwise at 20° C. The resulting reaction mixture was stirred at 60° C. for 8 h. The solvents were removed in vacuo and the residue was partitioned between H₂O (150 mL) and EtOAc (100 mL). The aqueous layer was further extracted with EtOAc (2×100 mL), and the combined organic layers were dried (Na₂SO₄) and the solvents were removed in vacuo. The residue was purified by column chromatography (normal basic activated alumina, 0.5% to 1.0% MeOH in DCM) to give tert-butyl 4-[cyclopropyl(2-methoxy-2-oxoethyl)amino]piperidine-1-carboxylate (310 mg, 80%) as a gum.

LCMS (Method I): m/z 313 [M+H]⁺ (ES⁺), at 4.85 min, UV active tert-Butyl 4-[cyclopropyl(2-methoxy-2-oxoethyl)amino] piperidine-1-carboxylate (300 mg, 0.96 mmol) was dissolved in 1,4-dioxane (5 mL) and 4 M HCl in 1,4-dioxane (3 mL) was added dropwise. The resulting reaction mixture was stirred at 25° C. for 16 h. The solvents were removed in vacuo, and the residue was purified by triturating with diethyl ether (3×5 mL) to give Intermediate 13, methyl [cyclopropyl(piperidin-4-yl)amino]acetate hydrochloride salt (210 mg, 85%) as a solid.

The data for the title compound are in Table 2.

Route 5

Typical Procedure for the Preparation of Amines Substituted with an Arylmethyl Group, as Exemplified by the Preparation of Intermediate 15, N-cyclopropyl-N-(1,2-oxazol-3-ylmethyl)piperidin-4-amine hydrochloride Route 6

Typical Procedure for the Preparation of Amines Substituted with Two Alkyl Groups, as Exemplified by the Preparation of Intermediate 18, N-ethyl-N-(2,2,2-trifluoroethyl)piperidin-4-amine hydrochloride

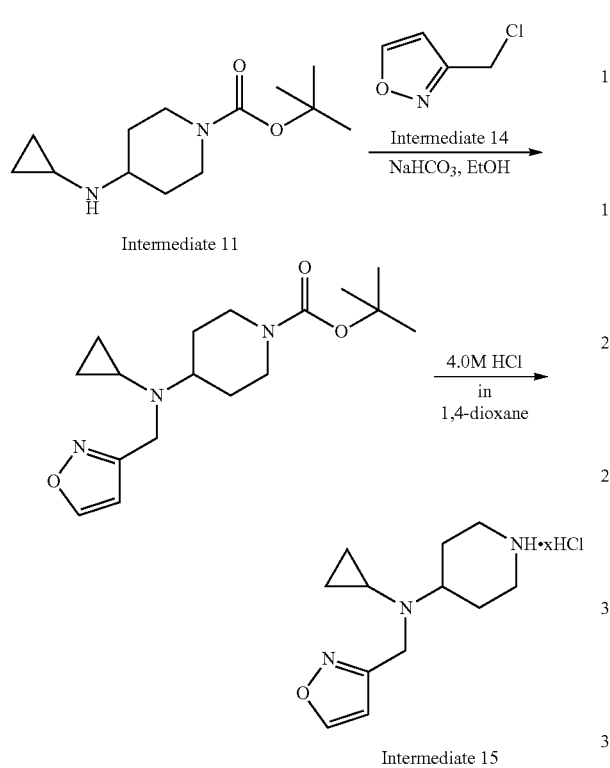

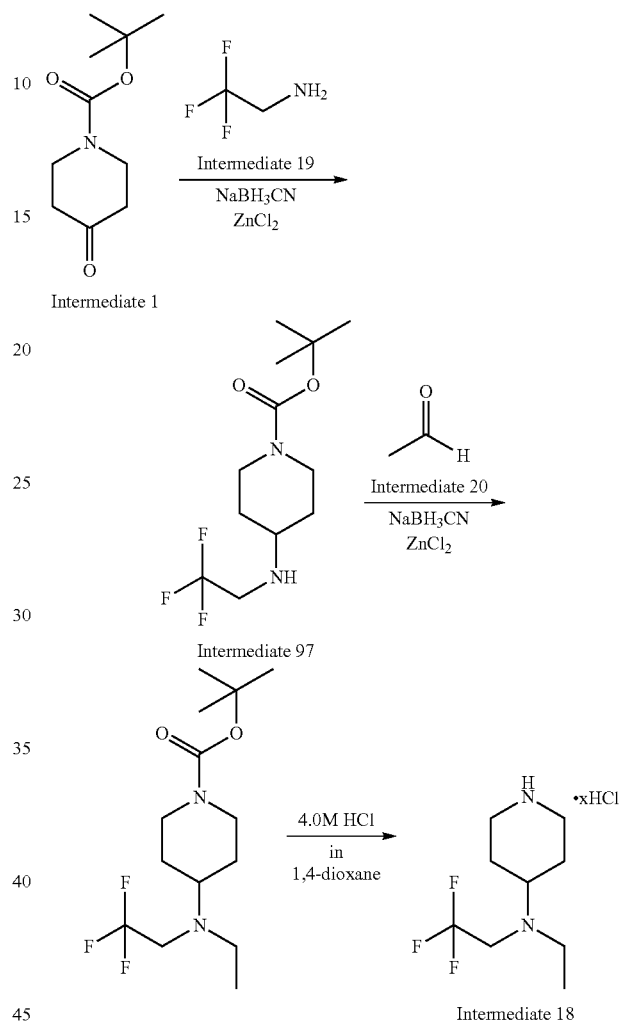

Intermediate 11, tert-butyl 4-(cyclopropylamino)piperidine-1-carboxylate (200 mg, 0.83 mmol) was dissolved in ethanol (10 mL) and sodium bicarbonate (200 mg, 2.38 mmol) was added. The reaction mixture was stirred at 0° C. for 30 min, then Intermediate 14, 3-(chloromethyl)-1,2-oxazole (97 mg, 0.83 mmol) was added dropwise at rt. The resulting reaction mixture was stirred at 60° C. for 16 h. The solvents were removed in vacuo and the residue was partitioned between H$_2$O (120 mL) and EtOAc (100 mL). The aqueous layer was further extracted with EtOAc (2×100 mL) and the combined organic layers were dried (Na$_2$SO$_4$), and the solvents were removed in vacuo. The residue was purified by column chromatography (normal basic activated alumina, 0.5% to 1.0% MeOH in DCM) to give tert-butyl 4-[cyclopropyl(1,2-oxazol-3-ylmethyl)amino]piperidine-1-carboxylate (150 mg, 58%) as a liquid.

LCMS (Method I): m/z 322 [M+H]$^+$ (ES$^+$), at 4.92 min, UV active tert-Butyl 4-[cyclopropyl(1,2-oxazol-3-ylmethyl)amino]piperidine-1-carboxylate (150 mg, 0.46 mmol) was dissolved in 1,4-dioxane (5 mL) and 4 M HCl in 1,4-dioxane (5 mL) was added dropwise. The resulting reaction mixture was stirred at 25° C. for 16 h. The solvents were removed in vacuo, and the residue was purified by triturating with diethyl ether (3×5 mL) to give Intermediate 15, N-cyclopropyl-N-(1,2-oxazol-3-ylmethyl)piperidin-4-amine hydrochloride salt (120 mg, 100%) as a solid.

The data for the title compound are in Table 2.

To Intermediate 1, tert-butyl 4-oxopiperidine-1-carboxylate (500 mg, 2.5 mmol) as a solution in MeOH (10 mL) was added Intermediate 19, 2,2,2-trifluoroethanamine (273 mg, 2.8 mmol), triethylamine (1.0 mL, 7.5 mmol) and ZnCl$_2$ (34 mg, 0.3 mmol) and the reaction mixture was stirred at 60° C. for 7 h. NaBH$_3$CN (475 mg, 7.5 mmol) was then added portionwise and the resulting reaction mixture was stirred at 25° C. for 17 h. The solvent was removed in vacuo and the residue was partitioned between H$_2$O (150 mL) and EtOAc (120 mL). The aqueous layer was further extracted with EtOAc (2×120 mL) and the combined organic phases were dried (Na$_2$SO$_4$) and the solvent was removed in vacuo. The residue was purified by column chromatography (normal basic activated alumina, 0.5% to 1.0% MeOH in DCM) to give Intermediate 97, tert-butyl 4-[(2,2,2-trifluoroethyl)amino]piperidine-1-carboxylate (350 mg, 49%) as a gum.

The data for Intermediate 97 are in Table 2.

To Intermediate 97, tert-butyl 4-[(2,2,2-trifluoroethyl)amino]piperidine-1-carboxylate (300 mg, 1.1 mmol) as a solution in MeOH (10 mL) was added Intermediate 20, acetaldehyde (69 mg, 1.6 mmol), triethylamine (0.4 mL, 3.2 mmol) and ZnCl$_2$ (14 mg, 0.1 mmol) and the reaction mixture was stirred at 50° C. for 7 h. The mixture was allowed to cool to rt before addition of NaBH$_3$CN (201 mg, 3.2 mmol) portionwise. The mixture was stirred at 25° C. for 17 h, then the solvent was removed in vacuo. The residue was partitioned between H$_2$O (150 mL) and EtOAc (120 mL) and the aqueous layer was further extracted with EtOAc (2×120 mL). The combined organic phases were dried (Na$_2$SO$_4$) and the solvent was removed in vacuo. The residue was purified by column chromatography (normal basic activated alumina, at 0.5% to 3% MeOH in DCM) to give tert-butyl 4-[ethyl(2,2,2-trifluoroethyl)amino]piperidine-1-carboxylate (280 mg, 85%) as a gum.

LCMS (Method I): m/z 311 [M+H]$^+$ (ES$^+$), at 5.65 min, UV active

To tert-butyl 4-[ethyl(2,2,2-trifluoroethyl)amino]piperidine-1-carboxylate (220 mg, 0.7 mmol) in 1,4-dioxane (5 mL) was added 4.0 M HCl in 1,4-dioxane (5 mL) dropwise and the resulting mixture was stirred at 25° C. for 16 h. The solvents were removed in vacuo and the residue was purified by trituration with ether (3×5 mL) to give Intermediate 18, N-ethyl-N-(2,2,2-trifluoroethyl)piperidin-4-amine hydrochloride salt (164 mg, 94%) as a solid.

The data for the title compound are in Table 2.

Route 7

Typical Procedure for the Preparation of Amines, as Exemplified by the Preparation of Intermediate 21, N-cyclopropyl-N-(2-methoxyethyl)piperidin-4-amine hydrochloride mixture was stirred at 75° C. for 70 h. The solvent was removed in vacuo and the residue was partitioned between H$_2$O (150 mL) and EtOAc (120 mL). The aqueous layer was further extracted with EtOAc (2×120 mL) and the combined organic phases were dried (Na$_2$SO$_4$) and the solvent was removed in vacuo. The residue was purified by column chromatography (normal basic activated alumina, 0.5% MeOH in DCM) to give tert-butyl 4-[cyclopropyl(2-methoxyethyl)amino]piperidine-1-carboxylate (0.27 g, 44%) as a gum.

LCMS (Method I): m/z 299 [M+H]$^+$ (ES$^+$), at 4.81 min, UV active

To a solution of tert-butyl 4-[cyclopropyl(2-methoxyethyl)amino]piperidine-1-carboxylate (0.27 g, 0.9 mmol) in 1,4-dioxane (5 mL) was added 4.0 M HCl in 1,4-dioxane (5 mL) dropwise and the resulting reaction mixture was stirred at 25° C. for 16 h. The solvent was removed in vacuo and the residue was purified by triturating with ether (3×5 mL) to give Intermediate 21, N-cyclopropyl-N-(2-methoxyethyl)piperidin-4-amine hydrochloride salt (0.17 g, 81%) as a solid.

The data for the title compound are in Table 2.

Route 8

Typical Procedure for the Preparation of Piperidines, as Exemplified by the Preparation of Intermediate 35, N-cyclopropyl-N-(piperidin-4-ylmethyl)acetamide hydrochloride

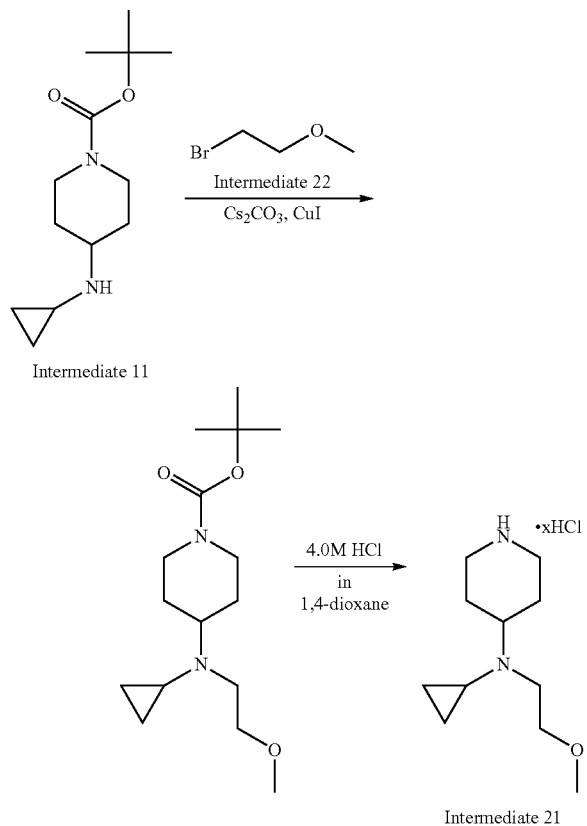

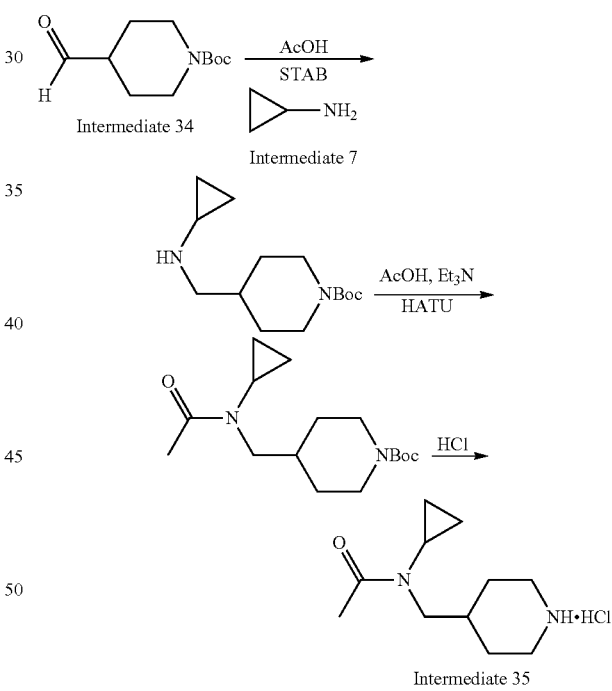

To a solution of Intermediate 11, tert-butyl 4-(cyclopropylamino)piperidine-1-carboxylate (0.50 g, 2.1 mmol) in acetonitrile (10 mL) was added Cs$_2$CO$_3$ (2.03 g, 6.2 mmol) and CuI (20 mg) and the reaction mixture was stirred at 70° C. for 1 h. Intermediate 22, 1-bromo-2-methoxyethane (0.43 g, 3.1 mmol) was then added dropwise at 25° C. and the To Intermediate 34, tert-butyl 4-formylpiperidine-1-carboxylate (427 mg, 2.0 mmol) and Intermediate 7, cyclopropanamine (114 mg, 2.0 mmol) as a solution in DCM (10 mL) at rt was added AcOH (0.23 mL, 4.0 mmol). The mixture was stirred for 3 h then STAB (1.06 g, 5.0 mmol) was added and the mixture was stirred at rt overnight. The reaction mixture was quenched with the addition of sat. aq. NaHCO$_3$ (20 mL). Solid Na$_2$CO$_3$ was added to ensure the aqueous layer was basic, then the reaction mixture was extracted with DCM (4×20 mL). The organic layers were combined, dried (MgSO$_4$), filtered and the solvents were removed in vacuo to give crude tert-butyl 4-[(cyclopropylamino)methyl]pip eridine-1-carboxylate (assumed 100%) which was used directly without further purification.

LCMS (Method C): m/z 255 (M+H)+ (ES+), at 1.38 min, UV active.

To a solution of tert-butyl 4-[(cyclopropylamino)methyl] piperidine-1-carboxylate (assumed 2.0 mmol) in DCM (10 mL) was added Et₃N (1.12 mL, 8.0 mmol), HATU (914 mg, 2.4 mmol) and AcOH (0.23 mL, 4.0 mmol) and the reaction mixture was stirred overnight. The mixture was quenched with the addition of sat. aq. NaHCO₃ (20 mL) and extracted with DCM (4×20 mL). The organic layers were combined, dried (MgSO₄), filtered and the solvents were removed in vacuo to give crude tert-butyl 4-{[acetyl(cyclopropyl) amino]methyl}piperidine-1-carboxylate (assumed 100%) which was used directly without further purification.

LCMS (Method C): m/z 319 (M+Na)+ (ES+), at 1.26 min, UV active.

To a suspension of tert-butyl 4-{[acetyl(cyclopropyl) amino]methyl}piperidine-1-carboxylate (assumed 2.0 mmol) in DCM (10 mL) was added 4.0 M HCl in 1,4-dioxane (2.5 mL, 10.0 mmol) and the mixture was stirred at rt overnight. The solvents were removed in vacuo to give Intermediate 35, N-cyclopropyl-N-(piperidin-4-ylmethyl) acetamide hydrochloride salt (assumed 2.0 mmol) as a solid which was used without further purification.

The data for the title compound are in Table 2

Route 9

Typical Procedure for the Preparation of Piperidines, as Exemplified by the Preparation of Intermediate 36, N-cyclopropyl-N-(piperidin-4-ylmethyl)propanamide hydrochloride

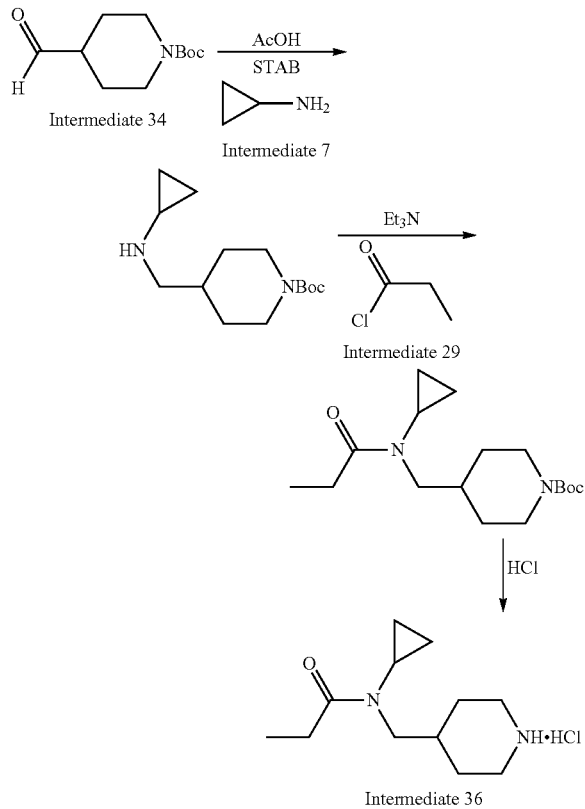

Intermediate 36

To a solution of Intermediate 34, tert-butyl 4-formylpiperidine-1-carboxylate (0.43 g, 2.0 mmol) and Intermediate 7, cyclopropanamine (0.11 g, 2.0 mmol) in DCM (10 mL) at rt was added AcOH (0.23 mL, 4.0 mmol) and the resulting mixture was stirred for 3 h. STAB (1.06 g, 5.0 mmol) was added and the mixture was stirred at rt overnight. The reaction mixture was quenched with the addition of sat. aq. NaHCO₃ (20 mL), then solid Na₂CO₃ was added to ensure the aqueous layer was basic. The mixture was extracted with DCM (4×20 mL) and the combined organic layers were dried (MgSO₄), filtered and the solvents were removed in vacuo to give crude tert-butyl 4-[(cyclopropylamino) methyl]piperidine-1-carboxylate (assumed 100%) which was used directly without further purification.

LCMS (Method C): m/z 255 (M+H)+ (ES+), at 1.38 min, UV active.

To a solution of tert-butyl 4-[(cyclopropylamino)methyl] piperidine-1-carboxylate (assumed 2.0 mmol) in DCM (10 mL), Et₃N (1.12 mL, 8.0 mmol) and Intermediate 29, propanoyl chloride (0.26 mL, 3.0 mmol) were added and the reaction mixture was stirred overnight. The mixture was quenched with the addition of sat. aq. NaHCO₃ (20 mL) and extracted with DCM (4×20 mL). The organic layers were combined, dried (MgSO₄), filtered and the solvents were removed in vacuo to give crude tert-butyl 4-{[cyclopropyl (propanoyl)amino]methyl}piperidine-1-carboxylate (assumed 100%) which was used directly without further purification.

LCMS (Method C): m/z 333 (M+Na)+ (ES+), at 1.39 min, UV active.

To a suspension of tert-butyl 4-{[cyclopropyl(propanoyl) amino]methyl}piperidine-1-carboxylate (assumed 2.0 mmol) in DCM (10 mL), 4.0 M HCl in 1,4-dioxane (2.5 mL, 10.0 mmol) was added and the mixture was stirred at rt overnight. The solvents were removed in vacuo to give Intermediate 36, N-cyclopropyl-N-(piperidin-4-ylmethyl) propanamide hydrochloride salt, (assumed 100%) as a solid which was used without further purification.

The data for the title compound are in Table 2

Route 10

Typical Procedure for the Preparation of Piperidines, as Exemplified by the Preparation of Intermediate 42, N-ethyl-N-(piperidin-4-yl) formamide

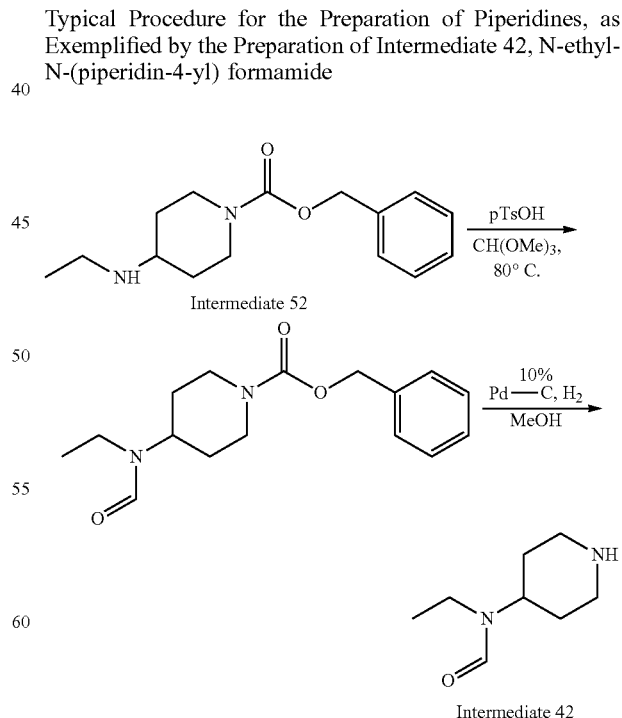

Intermediate 42

Intermediate 52, benzyl 4-(ethylamino)piperidine-1-carboxylate (500 mg, 1.91 mmol) and p-toluenesulphonic acid (10 mg, 0.06 mmol) were dissolved in triethyl orthoformate (3.3 mL, 19.84 mmol) at rt and the reaction mixture was stirred at 80° C. for 16 h. The reaction mixture was quenched with 0.1 N HCl (30 mL) and extracted with 10% MeOH in DCM (2×30 mL). The organic layers were combined, washed with sat. aqueous NaHCO$_3$ (30 mL) and dried (Na$_2$SO$_4$). The solvent was removed in vacuo to give crude benzyl 4-[ethyl(formyl)amino]piperidine-1-carboxylate (400 mg, 100%) as a gum, which was used without further purification.

LCMS (Method F): m/z 291 [M+H]$^+$ (ES$^+$), at 1.86 min, UV active.

Benzyl 4-[ethyl(formyl)amino]piperidine-1-carboxylate (180 mg, 0.62 mmol) was dissolved in MeOH (15 mL) and 10% Pd/C (50% moisture) (100 mg, 0.09 mmol) was added at rt under a nitrogen atmosphere. The system was purged of nitrogen and placed under hydrogen gas and stirred at rt for 16 h. The catalyst was removed by filtration and the filtrate was concentrated in vacuo to give crude Intermediate 42, N-ethyl-N-piperidin-4-ylformamide (100 mg, 100%) as a gum.

The data for the title compound is in Table 2.

Route 11

Typical Procedure for the Preparation of Piperidines, as Exemplified by the Preparation of Intermediate 53, N-ethyl-N-(piperidin-4-yl)acetamide trifluoroacetate

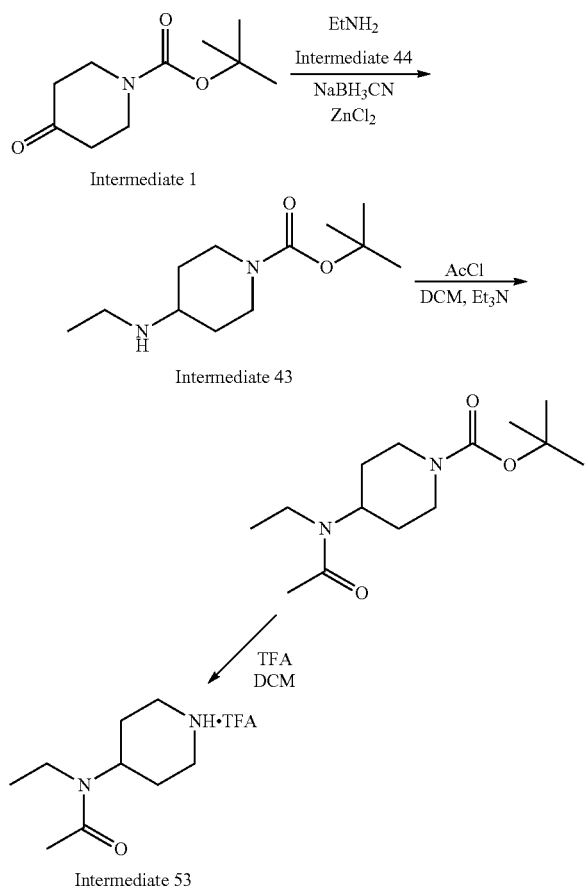

To Intermediate 1, tert-butyl 4-oxopiperidine-1-carboxylate (3.0 g, 15.1 mmol) in MeOH (40 mL) was added Intermediate 44, ethanamine (2 M in THF, 12.6 mL, 25.1 mmol), Et$_3$N (4.2 mL, 30.3 mmol) and ZnCl$_2$ (0.1 g, 0.7 mmol) and the reaction mixture was stirred at 60° C. for 7 h. NaBH$_3$CN (1.2 g, 19.6 mmol) was added portionwise and the resulting reaction mixture was stirred at rt for 17 h. The solvents were removed in vacuo and the residue was partitioned between H$_2$O (250 mL) and EtOAc (200 mL) and the aqueous layer was further extracted with EtOAc (2×200 mL). The combined organic phases were dried (Na$_2$SO$_4$), the solvent was removed in vacuo and the residue was purified by column chromatography (normal basic activated alumina, 10 to 30% EtOAc in hexane) to give Intermediate 43, tert-butyl 4-(ethylamino)piperidine-1-carboxylate (3.0 g, 88%) as a gum.

The data for Intermediate 43 is in Table 2.

To Intermediate 43, tert-butyl 4-(ethylamino)piperidine-1-carboxylate (0.20 g, 0.9 mmol) in DCM (10 mL) was added triethylamine (0.15 mL, 1.1 mmol) dropwise and the resulting mixture was stirred at 0° C. for 30 min. Acetyl chloride (0.09 g, 1.1 mmol) was then added dropwise at 0° C. and the resulting reaction mixture was stirred at rt for 8 h. The solvents were removed in vacuo and the residue was partitioned between H$_2$O (120 mL) and EtOAc (100 mL). The aqueous layer was further extracted with EtOAc (2×100 mL) and the combined organic phases were dried (Na$_2$SO$_4$) and the solvent was removed in vacuo. The crude residue was purified by column chromatography (normal basic activated alumina, 0.5 to 1.0% MeOH in DCM) to give tert-butyl 4-[acetyl(ethyl)amino]piperidine-1-carboxylate (0.15 g, 63%) as a liquid.

LCMS (Method I): m/z 271 [M+H]$^+$ (ES$^+$), at 3.79 min, UV active.

To tert-butyl 4-[acetyl(ethyl)amino]piperidine-1-carboxylate (450 mg, 1.66 mmol) in DCM (15 mL) was added trifluoroacetic acid (1.3 mL, 16.66 mmol) dropwise at 0° C. The resulting reaction mixture was stirred at rt for 16 h. The solvent was removed in vacuo and the residue was purified by triturating with diethyl ether (3×5 mL) to give Intermediate 53, N-ethyl-N-(piperidin-4-yl)acetamide trifluoroacetate salt (450 mg, 100%) as a gum.

The data for the title compound is in Table 2.

Route 12

Typical Procedure for the Preparation of Piperidines, as Exemplified by the Preparation of Intermediate 76, N-methoxy-N-(piperidin-4-yl)acetamide trifluoroacetate

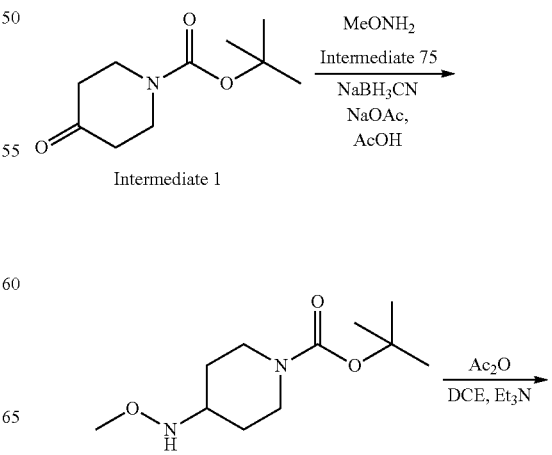

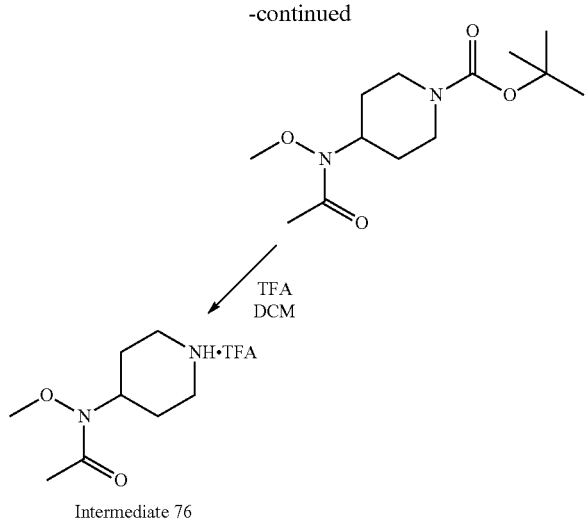

Intermediate 76

To Intermediate 75, O-methylhydroxylamine (0.5 g, 6.0 mmol) in MeOH (25 mL) was added sodium acetate (0.51 g, 6.2 mmol) and the reaction mixture was stirred at rt for 5 minutes. Intermediate 1, tert-Butyl 4-oxopiperidine-1-carboxylate (1.0 g, 5.0 mmol), AcOH (0.5 g, 8.8 mmol) and NaBH$_3$CN (0.3 g, 5.0 mmol) were added. The resulting reaction mixture was stirred at rt for 24 h, then partitioned between H$_2$O (30 mL) and EtOAc (50 mL). The organic phase was washed with sat. aq. NaHCO$_3$ (20 mL) and sat. aq. NaCl (20 mL). The organic phase was dried (Na$_2$SO$_4$), the solvent was removed in vacuo and the residue was purified by column chromatography (normal phase silica, EtOAc and hexanes) to give tert-butyl 4-(methoxyamino)piperidine-1-carboxylate(1 g, 90%) as a solid.

LCMS (Method F): m/z 231 [M+H]$^+$ (ES)$^+$, at 2.07 min, UV active.

To a stirred solution of tert-butyl 4-(methoxyamino)piperidine-1-carboxylate (120 mg, 0.52 mmol) in DCE (3 ml) was added Ac$_2$O (79 mg, 0.78 mmol) and Et$_3$N (0.1 mL, 0.78 mmol) at 0° C. The reaction mixture was heated to 50-60° C. for 3 h, then partitioned between H$_2$O (5 mL) and DCM (10 mL). The aqueous layer was further extracted with DCM (2×10 mL), and the combined organic phases were washed with sat. aq. NaHCO$_3$ (30 mL) and sat. aq. NaCl (30 mL), then dried (Na$_2$SO$_4$) and the solvent was removed in vacuo to give crude tert-butyl 4-[acetyl(methoxy)amino]piperidine-1-carboxylate (110 mg, 77%) which was used in the next step without further purification.

LCMS (Method F): m/z 273 [M+H]$^+$ (ES)$^+$, at 2.02 min, UV active

To a stirred solution of tert-butyl 4-[acetyl(methoxy)amino]piperidine-1-carboxylate (110 mg, 0.40 mmol) in DCM (5 mL) was added TFA (2 mL) dropwise at 0° C. and the resulting mixture was stirred at rt for 3 h. The solvent was removed in vacuo and the residue was dried by coevaporation from toluene (x 3) to give Intermediate 76, N-methoxy-N-(piperidin-4-yl)acetamide trifluoroacetate salt (120 mg, 100%) as a gum which was used without further purification.

The data for the title compound is in Table 2.

Route 13
Typical Procedure for the Preparation of Amines, as Exemplified by the Preparation of Intermediate 89, 1-(1,3-oxazol-5-yl)methanamine hydrochloride

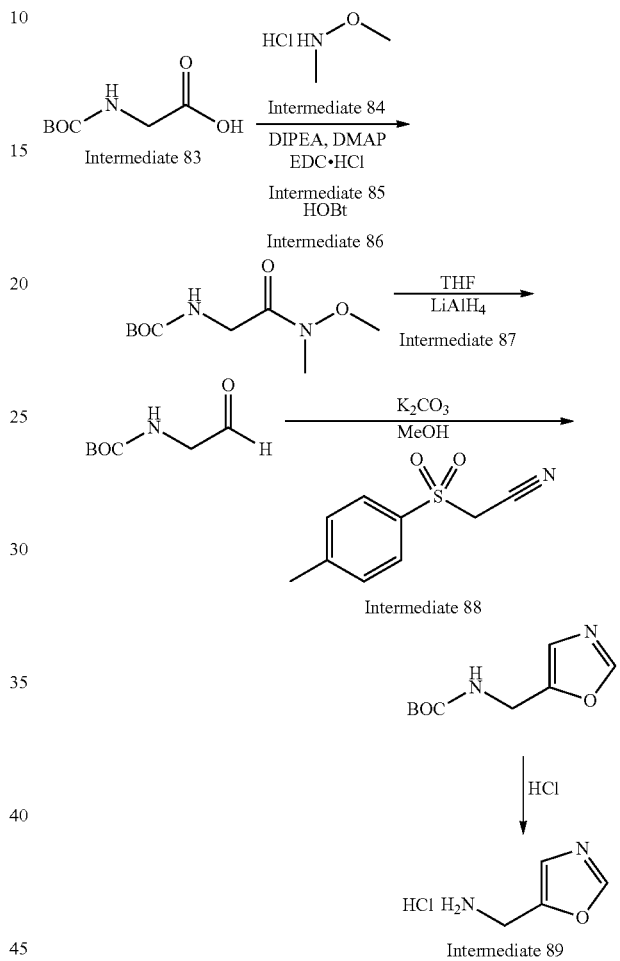

Intermediate 83, [(tert-butoxycarbonyl)amino]acetic acid (5.00 g, 28.5 mmol), DIPEA (14.75 g, 104 mmol) and Intermediate 84, N-methoxymethanamine hydrochloride (5.60 g, 57.0 mmol) were dissolved in DCM (100 mL) and DMF (100 mL) and Intermediate 85, EDC hydrochloride (6.56 g, 34.0 mmol) was added. The reaction mixture was stirred under nitrogen at 0° C. for 1 h, then Intermediate 86, HOBt (4.63 g, 34.0 mmol) and DMAP (100 mg) were added portionwise and the resulting mixture was stirred for 16 h at room temperature. The reaction mixture was partitioned between H$_2$O (250 mL) and DCM (100 mL), and the aqueous layer was further extracted with EtOAc (2×100 mL). The combined organic layers were dried (Na$_2$SO$_4$), filtered and the solvent was removed in vacuo. The residue was purified by column chromatography (Normal-Phase Silica, 0 to 3% methanol in DCM) to give tert-butyl {2-[methoxy(methyl)amino]-2-oxoethyl}carbamate (4.50 g, 72%) as a solid.

LCMS (Method F): m/z 219 (M+H)$^+$ (ES$^+$), at 1.77 min, UV active.

tert-Butyl {2-[methoxy(methyl)amino]-2-oxoethyl}carbamate (4.50 g, 20.6 mmol), was dissolved in THF (50.0 mL) and Intermediate 87, lithium aluminium hydride (1.0 M in THF, 20.6 mL, 20.6 mmol) was added at −30° C. dropwise. The mixture was stirred for 20 min at −30° C., then excess sodium sulfate decahydrate was added portionwise. The mixture was stirred for 30 min, then filtered through a Celite pad and the filtrate was concentrated in vacuo to give crude tert-butyl (2-oxoethyl)carbamate (390 mg, 85%) as a gum which was used without further purification.

$^1$H NMR: (400 MHz, DMSO-$d_6$) δ: 1.39-1.40 (m, 12 H), 2.46-2.47 (m, 3 H), 2.89-2.95 (m, 1 H), 3.05-3.12 (m, 1 H), 4.11-4.19 (m, 1 H).

tert-Butyl (2-oxoethyl)carbamate (3.00 g, 18.8 mmol), Intermediate 88, p-toluenesulfonylmethyl isocyanide (5.52 g, 28.2 mmol) and $K_2CO_3$ (7.78 g, 56.4 mmol) were mixed in methanol (50 mL) and stirred at 0° C. over 70 h. The reaction mixture was partitioned between $H_2O$ (30 mL) and EtOAc (20 mL), and the aqueous layer was further extracted with EtOAc (2×20 mL). The combined organic layers were dried ($Na_2SO_4$), filtered and concentrated in vacuo. The residue was purified by column chromatography (Normal-Phase Silica, 0 to 3% MeOH in DCM) to give tert-butyl (1,3-oxazol-5-ylmethyl)carbamate (900 mg, 24%) as a gum.

LCMS (Method F): m/z 199 (M+H)$^+$ (ES$^+$), at 1.72 min, UV active.

tert-Butyl (1,3-oxazol-5-ylmethyl)carbamate (900 mg, 0.45 mmol) was dissolved in 1,4-dioxane (10 mL) and 4 M HCl in 1,4-dioxane (10 mL) was added and the resulting mixture was stirred for 3 h at room temperature. The reaction mixture was concentrated and the residue was dried by co-evaporation from diethyl ether (5 mL) to give Intermediate 89, 1-(1,3-oxazol-5-yl)methanamine hydrochloride salt (400 mg, 90%) as a gum which was used without further purification.

The data for the title compound are in Table 2

Route 14

Typical Procedure for the Preparation of Amines, as Exemplified by the Preparation of Intermediate 98, methyl piperidin-4-yl(2,2,2-trifluoroethyl)carbamate hydrochloride

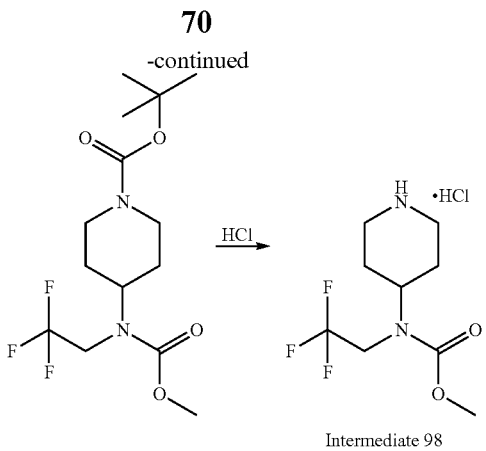

Intermediate 98

Intermediate 97, tert-butyl 4-[(2,2,2-trifluoroethyl)amino]piperidine-1-carboxylate (300 mg, 1.06 mmol) was dissolved in acetonitrile (10 mL) and $K_2CO_3$ (450 mg, 3.19 mmol) was added. The mixture was stirred at 70° C. for 2 h then cooled to 0° C. Intermediate 40, methyl carbonochloridate (0.12 mL, 1.59 mmol) was added dropwise and the resulting reaction mixture stirred at 25° C. for 8 h. The solvents were removed in vacuo and the residue was partitioned between $H_2O$ (120 mL) and EtOAc (100 mL). The aqueous layer was further extracted with EtOAc (2×100 mL) and the combined organic layers were dried ($Na_2SO_4$), filtered and concentrated in vacuo. The residue was purified by column chromatography (normal neutral activated alumina, at 10% to 15% EtOAc in hexane) to give tert-butyl 4-[(methoxycarbonyl)(2,2,2-trifluoroethyl)amino]piperidine-1-carboxylate (330 mg, 92%) as a gum.

LCMS (Method I): m/z 284 (M+H-56)$^+$ (ES$^+$), at 5.01 min, UV active.

tert-Butyl 4-[(methoxycarbonyl)(2,2,2-trifluoroethyl)amino]piperidine-1-carboxylate (330 mg, 0.97 mmol) was dissolved in 1,4-dioxane (5 mL), 4.0 M HCl in 1,4-dioxane (10 mL) was added dropwise and the resulting mixture was stirred at 25° C. for 8 h. The solvents were removed in vacuo and the residue was triturated with diethyl ether (3×3 mL) to give Intermediate 98, methyl piperidin-4-yl(2,2,2-trifluoroethyl)carbamate hydrochloride salt (210 mg, 90%) as a solid which was used without further purification.

The data for the title compound are in Table 2.

Route 15

Typical Procedure for the Preparation of Amines, as Exemplified by the Preparation of Intermediate 99, 2-methoxyethyl piperidin-4-yl(2,2,2-trifluoroethyl)carbamate hydrochloride

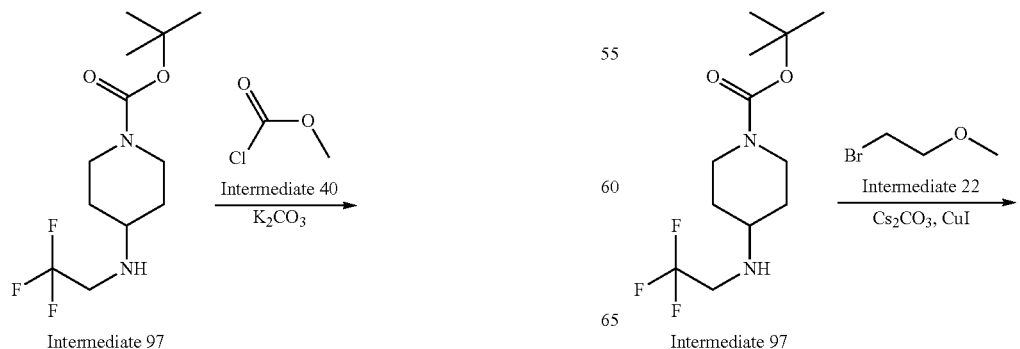

-continued

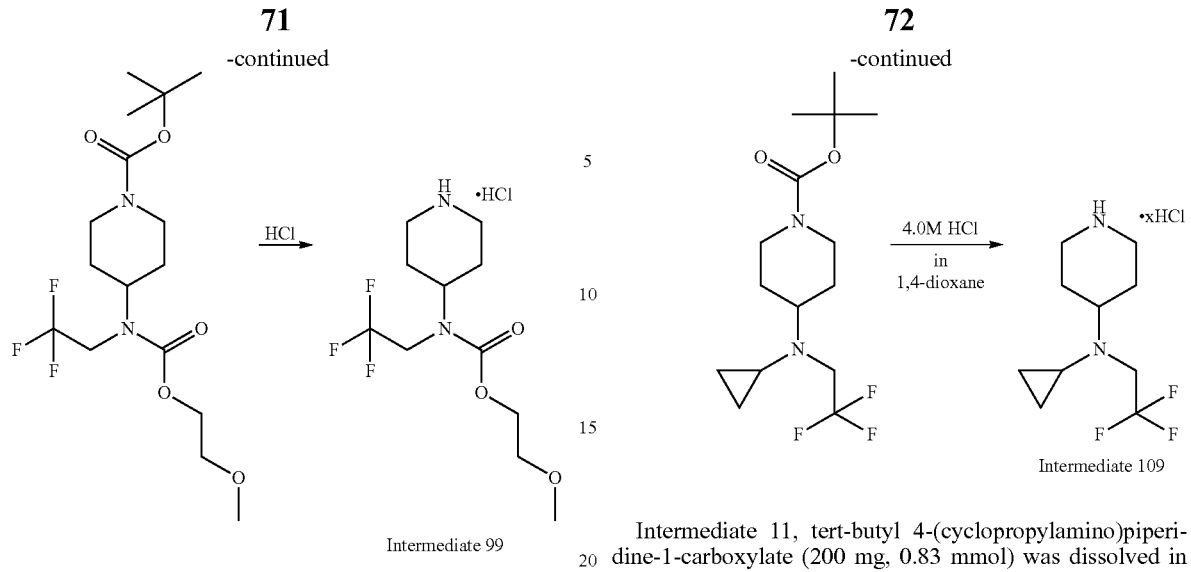

Intermediate 99

Intermediate 109

Intermediate 97, tert-butyl 4-((2,2,2-trifluoroethyl)amino)piperidine-1-carboxylate (1.0 g, 3.50 mmol) was dissolved in DMF (15 mL), $Cs_2CO_3$ (3.46 g, 10.6 mmol) and CuI (336 mg, 1.77 mmol) were added, and the reaction mixture was stirred at 70° C. for 5 h then cooled to 25° C.

Intermediate 22, 1-bromo-2-methoxyethane (986 mg, 7.09 mmol) was added and the reaction mixture was stirred at 90° C. for 7 days. The solvents were removed in vacuo and the residue was partitioned between $H_2O$ (180 mL) and EtOAc (120 mL). The aqueous layer was further extracted with EtOAc (3×120 mL) and the combined organic layers were dried ($Na_2SO_4$), filtered and concentratred in vacuo. The residue was purified by column chromatography (normal neutral activated alumina, at 8% EtOAc in hexane) to give tert-butyl 4-{[(2-methoxyethoxy)carbonyl](2,2,2-trifluoroethyl)amino}piperidine-1-carboxylate (280 mg, 21%) as a gum.

LCMS (Method I): m/z 329 (M+H-56)$^+$ (ES$^+$), at 4.90 min, UV active.

tert-Butyl 4-{[(2-methoxyethoxy)carbonyl](2,2,2-trifluoroethyl)amino}piperidine-1-carboxylate (240 mg, 0.71 mmol) was dissolved in 1,4-dioxane (5 mL), 4.0 M HCl in 1,4-dioxane (10 mL) was added dropwise and the resulting reaction mixture was stirred at 25° C. for 8 h. The solvents were removed in vacuo, and the residue was purified by triturating with diethyl ether (3×3 mL) to give Intermediate 99, 2-methoxyethyl piperidin-4-yl(2,2,2-trifluoroethyl)carbamate hydrochloride salt (170 mg, 96%) as a solid.

The data for the title compound are in Table 2.

Route 16

Typical Procedure for the Preparation of Amines, as Exemplified by the Preparation of Intermediate 109, N-cyclopropyl-N-(2,2,2-trifluoroethyl)piperidin-4-amine hydrochloride Intermediate 11, tert-butyl 4-(cyclopropylamino)piperidine-1-carboxylate (200 mg, 0.83 mmol) was dissolved in THF (10 mL), Intermediate 107, N-methyl-2-pyrrolidinone (0.6 mL) and triethylamine (0.5 mL, 3.30 mmol) were added and the reaction mixture was stirred at 70° C. for 1 h then cooled to room temperature. Intermediate 108, 2,2,2-trifluoroethyl trifluoromethanesulfonate (385 mg, 1.66 mmol) was added and the resulting reaction mixture was stirred at 80° C. for 70 h. The solvents were removed in vacuo, and the residue was partitioned between $H_2O$ (120 mL) and EtOAc (100 mL) and the aqueous layer was further extracted with EtOAc (2×100 mL). The combined organic layers were dried ($Na_2SO_4$), filtered and concentrated in vacuo and the residue was purified by column chromatography (normal neutral activated alumina, 0.5% MeOH in $CH_2Cl_2$) to give tert-butyl 4-[cyclopropyl(2,2,2-trifluoroethyl)amino]piperidine-1-carboxylate (220 mg, 82%) as a gum.

LCMS (Method I): m/z 267 (M+H-56)$^+$ (ES$^+$), at 5.90 min, UV active.

tert-Butyl 4-[cyclopropyl(2,2,2-trifluoroethyl)amino]piperidine-1-carboxylate (200 mg, 0.62 mmol) was dissolved in 1,4-dioxane (5 mL), 4.0 M HCl in 1,4-dioxane (5 mL) was added dropwise and the resulting reaction mixture was stirred at 25° C. for 16 h. The solvents were removed in vacuo and the residue was purified by triturating with diethyl ether (3×5 mL) to give Intermediate 109, N-cyclopropyl-N-(2,2,2-trifluoroethyl)piperidin-4-amine hydrochloride salt (160 mg, 100%) as a solid.

The data for the title compound are in Table 2.

Route 17

Typical Procedure for the Preparation of Amines, as Exemplified by the Preparation of Intermediate 111, 2-[cyclopropyl(piperidin-4-yl)amino]ethanol trifluoroacetate

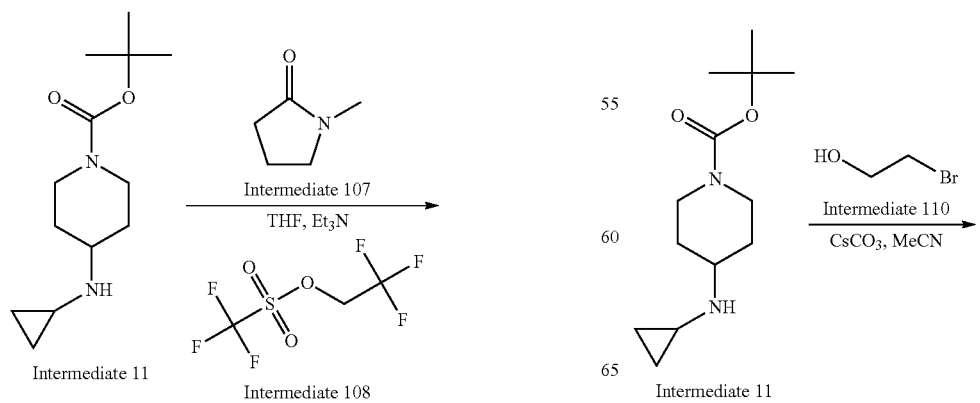

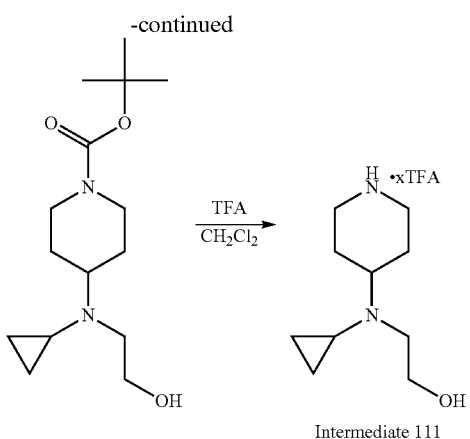

Intermediate 111

Intermediate 11, tert-butyl 4-(cyclopropylamino)piperidine-1-carboxylate (200 mg, 0.833 mmol) and cesium carbonate (0.812 g, 2.5 mmol) were added to MeCN (10 mL) and stirred at 25° C. for 15 min. Intermediate 110, 2-bromoethanol (134 mg, 1.08 mmol) was added and the reaction mixture was stirred at 60° C. for 16 h. The reaction mixture was partitioned between water (30 mL) and 10% methanol in CH$_2$Cl$_2$ (30 mL) and the aqueous layer was further extracted with 10% methanol in CH$_2$Cl$_2$ (2×30 mL). The organic layers were then combined, dried (Na$_2$SO$_4$), filtered and concentrated to give tert-butyl 4-[cyclopropyl(2-hydroxyethyl)amino]piperidine-1-carboxylate (180 mg, 76%) as a gum which was used without further purification.

LCMS (Method F): m/z 285 (M+H)$^+$ (ES$^+$), at 1.46 min, UV active.

tert-Butyl 4-[cyclopropyl(2-hydroxyethyl)amino]piperidine-1-carboxylate (365 mg, 1.29 mmol) was dissolved in CH$_2$Cl$_2$ (10 mL), trifluoroacetic acid (1.1 mL, 12.9 mmol) was added and the resulting reaction mixture was stirred at 25° C. for 16 h. The solvents were removed in vacuo and the residue was purified by triturating with diethyl ether (3×10 mL) to give Intermediate 111, 2-[cyclopropyl(piperidin-4-yl)amino]ethanol trifluoroacetate salt (380 mg, 100%) as a gum.

The data for the title compound are in Table 2.

Route 18

Typical Procedure for the Preparation of Amines, as Exemplified by the Preparation of Intermediate 112, tert-butyl 4-(cyclobutylamino)piperidine-1-carboxylate

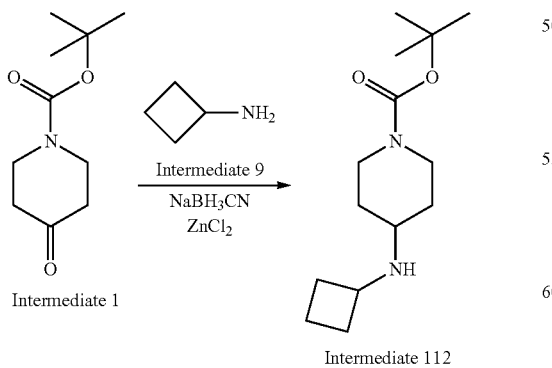

Intermediate 1, tert-butyl 4-oxopiperidine-1-carboxylate (500 mg, 2.51 mmol) was dissolved in methanol (10 mL), Intermediate 9, cyclobutanamine (178 mg, 2.51 mmol), triethylamine (1.0 mL, 7.53 mmol) and ZnCl$_2$ (34 mg, 0.25 mmol) were added at room temperature and the reaction mixture was stirred at 60° C. for 4 h. NaBH$_3$CN (475 mg, 7.53 mmol) was added portionwise, the resulting reaction mixture was stirred at 25° C. for 12 h and then the solvents were removed in vacuo. The residue was partitioned between H$_2$O (150 mL) and EtOAc (120 mL) and the aqueous layer was further extracted with EtOAc (2×120 mL). The organic layers were combined, dried (Na$_2$SO$_4$), filtered and concentrated in vacuo. The residue was purified by column chromatography (normal basic activated alumina, at 10% to 30% EtOAc in hexane) to give Intermediate 112, tert-butyl 4-(cyclobutylamino)piperidine-1-carboxylate (560 mg, 88%) as a gum.

The data for the title compound are in Table 2.

Route 19

Typical Procedure for the Preparation of Piperidines, as Exemplified by the Preparation of Intermediate 119, N-(2-methoxyethyl)-N-(2,2,2-trifluoroethyl)piperidin-4-amine trifluoroacetate

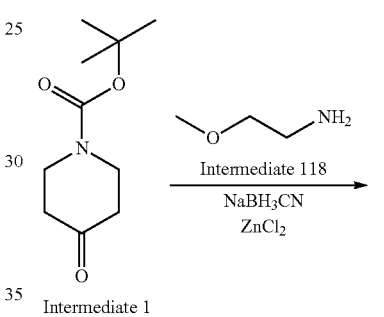

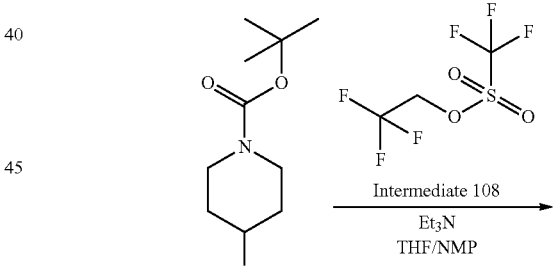

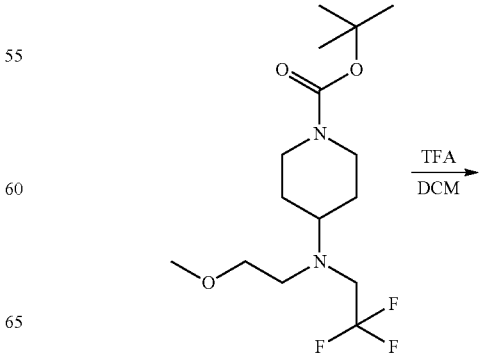

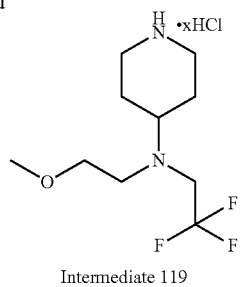

Intermediate 119

Intermediate 1, tert-butyl 4-oxopiperidine-1-carboxylate (1.0 g, 5.02 mmol), was dissolved in methanol (15 mL) and treated with Intermediate 118, 2-methoxyethylamine (490 mg, 6.53 mmol), triethylamine (2.1 mL, 15.1 mmol) and ZnCl$_2$ (68 mg, 0.50 mmol). The reaction mixture was stirred at 65° C. for 7 h, then NaBH$_3$CN (949 mg, 15.1 mmol) was added portionwise. The resulting reaction mixture was stirred at 25° C. for 17 h. The solvents were removed in vacuo, and the residue was partitioned between H$_2$O (150 mL) and EtOAc (120 mL). The aqueous layer was extracted with EtOAc (2×120 mL), and the organic layers were combined, dried (Na$_2$SO$_4$), and the solvent was removed in vacuo. The residue was purified by column chromatography (Normal basic activated alumina, 40% to 50% EtOAc in hexane) to give tert-butyl 4-[(2-methoxyethyl)amino]piperidine-1-carboxylate (480 mg, 37%) as a liquid.

LCMS (Method I): m/z 203 (M+H-56)$^+$ (ES$^+$), at 3.60 min, UV active.

tert-Butyl 4-[(2-methoxyethyl)amino]piperidine-1-carboxylate (300 mg, 1.16 mmol) was dissolved in THF (10 mL) and treated with N-methyl-2-pyrrolidinone (344 mg, 3.48 mmol) and triethylamine (0.7 mL, 4.65 mmol). The reaction mixture was stirred at 70° C. for 1 h, then Intermediate 108, 2,2,2-trifluoroethyl trifluoromethanesulfonate (297 mg, 1.28 mmol) was added dropwise at 25° C. The resulting reaction mixture was stirred at 70° C. for 16 h. The solvents were removed in vacuo and the reaction mixture was partitioned between H$_2$O (120 mL) and EtOAc (100 mL). The aqueous layer was further extracted with EtOAc (2×100 mL), and the combined organic layers were dried (Na$_2$SO$_4$). The solvent was removed in vacuo and residue was purified by column chromatography (Normal neutral activated alumina, at 10% to % EtOAc in hexane) to give tert-butyl 4-[(2-methoxyethyl)(2,2,2-trifluoroethyl)amino]piperidine-1-carboxylate (180 mg, 46%) as a gum.

LCMS (Method I): m/z 341 (M+H)$^+$ (ES$^+$), at 5.31 min, UV active.

tert-Butyl 4-[(2-methoxyethyl)(2,2,2-trifluoroethyl)amino]piperidine-1-carboxylate (150 mg, 0.44 mmol) was dissolved in DCM (3 mL) and cooled to 0° C. Trifluoroacetic acid (0.8 mL) was added dropwise and the resulting reaction mixture was stirred at 25° C. for 8 h. The solvents were removed in vacuo and the residue was purified by triturating with diethyl ether (3×2 mL) to give Intermediate 119, N-(2-methoxyethyl)-N-(2,2,2-trifluoroethyl)piperidin-4-amine trifluoroacetate salt (105 mg, 67%) as a gum.

The data for the title compound are in Table 2

Route 20
Typical Procedure for the Preparation of Piperidines, as Exemplified by the Preparation of Intermediate 120, N-ethyl-N-(oxetan-3-yl)piperidin-4-amine trifluoroacetate

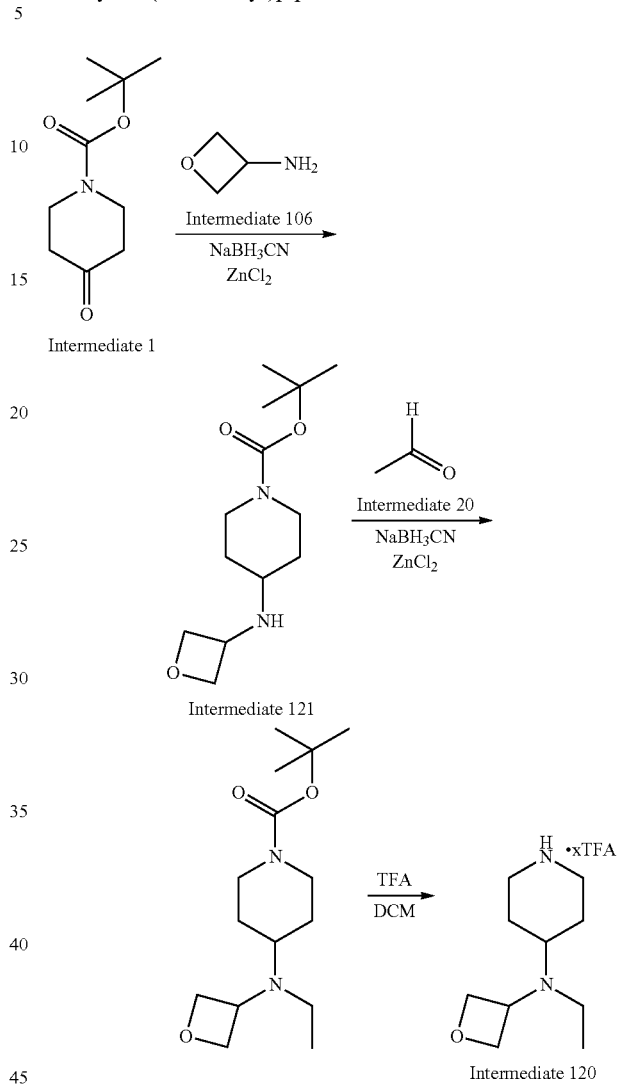

Intermediate 1, tert-butyl 4-oxopiperidine-1-carboxylate (546 mg, 4.10 mmol) was dissolved in methanol (20 mL). Intermediate 106, oxetan-3-amine (300 mg, 4.10 mmol), triethylamine (1.7 mL, 12.3 mmol) and ZnCl$_2$ (56 mg, 0.41 mmol) were added and then the reaction mixture was stirred at 65° C. for 8 h. NaBH$_3$CN (776 mg, 1.23 mmol) was then added portionwise and the resulting reaction mixture was stirred at 25° C. for 17 h. The solvents were removed in vacuo, and the residue was partitioned between H$_2$O (120 mL) and EtOAc (100 mL). The aqueous layer was further extracted with EtOAc (2×100 mL) and the combined organic layers were dried (Na$_2$SO$_4$). The solvent was removed in vacuo and the residue was purified by triturating with pentane and decanting off the solvents to give tert-butyl 4-(oxetan-3-ylamino)piperidine-1-carboxylate (680 mg, 97%) as a gum.

LCMS (Method I): m/z 257 (M+H)$^+$ (ES$^+$), at 2.92 min, UV active.

tert-Butyl 4-(oxetan-3-ylamino)piperidine-1-carboxylate (200 mg, 0.78 mmol) was dissolved in methanol (10 mL)

and Intermediate 20, acetaldehyde (103 mg, 2.34 mmol), triethylamine (0.3 mL, 2.34 mmol) and ZnCl$_2$ (11 mg, 0.08 mmol) were added. The reaction mixture was stirred at 50° C. for 7 h, then NaBH$_3$CN (148 mg, 2.34 mmol) was added portionwise. The resulting reaction mixture was stirred at 25° C. for 17 h. The solvents were removed in vacuo, and the residue was partitioned between H$_2$O (100 mL) and EtOAc (80 mL). The aqueous layer was further extracted with EtOAc (2×80 mL), and the combined organic layers were dried (Na$_2$SO$_4$). The solvent was removed in vacuo and the residue was purified by column chromatography (Normal basic activated alumina, 0.5% to 3% MeOH in DCM) to give tert-butyl 4-[ethyl(oxetan-3-yl)amino]piperidine-1-carboxylate (180 mg, 81%) as a gum.

LCMS (Method I): m/z 285 (M+H)$^+$ (ES$^+$), at 3.84 min, UV active.

tert-Butyl 4-[ethyl(oxetan-3-yl)amino]piperidine-1-carboxylate (180 mg, 0.63 mmol) was dissolved in DCM (8 mL) and cooled to 0° C. Trifluoroacetic acid (2 mL) was added dropwise and the resulting reaction mixture was stirred at 25° C. for 6 h. The solvents were removed in vacuo, and the residue was purified by triturating with diethyl ether (3×1 mL) to give Intermediate 120, N-ethyl-N-(oxetan-3-yl)piperidin-4-amine trifluoroacetate salt (110 mg, 95%) as a gum.

The data for the title compound are in Table 2

Route 21

Typical Procedure for the Preparation of Piperidines, as Exemplified by the Preparation of Intermediate 128, N-ethyl-N-methoxypiperidin-4-amine trifluoroacetate To a stirred solution of Intermediate 75, O-methylhydroxylamine (0.5 g, 6.0 mmol) in MeOH (25 mL) was added NaOAc (0.51 g, 6.2 mmol) and the reaction mixture was stirred at rt for five minutes. Intermediate 1, tert-butyl 4-oxopiperidine-1-carboxylate (1 g, 5.0 mmol), AcOH (0.5 g, 8.8 mmol) and NaCNBH$_3$ (0.3 g, 5.0 mmol) were added and the reaction mixture was stirred at rt for 24 hours. The reaction mixture was distributed between EtOAc and water, and the EtOAc phase was separated and washed with aq. NaHCO$_3$ and brine solution. The organic phase was dried with Na$_2$SO$_4$ and concentrated in vacuo to give the crude product, which was purified by column chromatography (Normal-Phase Silica and EtOAc and hexanes as eluent solvents) to give tert-butyl 4-(methoxyamino)piperidine-1-carboxylate (1 g, 90%) as a solid.

LCMS (Method F): m/z 231 (M+H)$^+$ (ES$^+$), at 2.07 min, UV active.

To a stirred solution of tert-butyl 4-(methoxyamino)piperidine-1-carboxylate (300 mg, 1.30 mmol) in DMF (5 ml) was added K$_2$CO$_3$ (540 mg, 3.91 mmol) and the mixture was stirred at 80° C. for 1 hour. Intermediate 127, iodoethane (305 mg, 1.96 mmol) was then added and the mixture was stirred at 80° C. for 16 hours. The reaction mixture was cooled to RT, diluted with cold water (10 ml) and the compound was extracted with EtOAc (20 ml). The aqueous layer was further extracted with EtOAc (2×20 mL) and the combined organic layers were washed with brine solution then dried with Na$_2$SO$_4$. The solvent was removed in vacuo to give the crude product, which was purified by column chromatography (Normal-Phase Silica and EtOAc and hexanes as eluent solvents) to give tert-butyl 4-[ethyl (methoxy)amino]piperidine-1-carboxylate (160 mg, 47%).

LCMS (Method F): m/z 259 (M+H)$^+$ (ES$^+$), at 2.02 min, UV active.

To a stirred solution of tert-butyl 4-[ethyl(methoxy)amino]piperidine-1-carboxylate (160 mg, 0.62 mmol) in DCM (8 ml) was added TFA (3 mL) dropwise at 0° C. and the resulting mixture was stirred at room temperature for 3 h. The solvent was then evaporated in vacuo and the residue was dried by co-evaporation from toluene (×3) to give Intermediate 128, N-ethyl-N-methoxypiperidin-4-amine trifluoroacetate salt (150 mg, 63%) as a gum.

The data for the title compound are in Table 2

Route 22

Typical Procedure for the Preparation of Piperidines, as Exemplified by the Preparation of Intermediate 130, 2-[phenyl(piperidin-4-yl)amino]ethanol hydrochloride

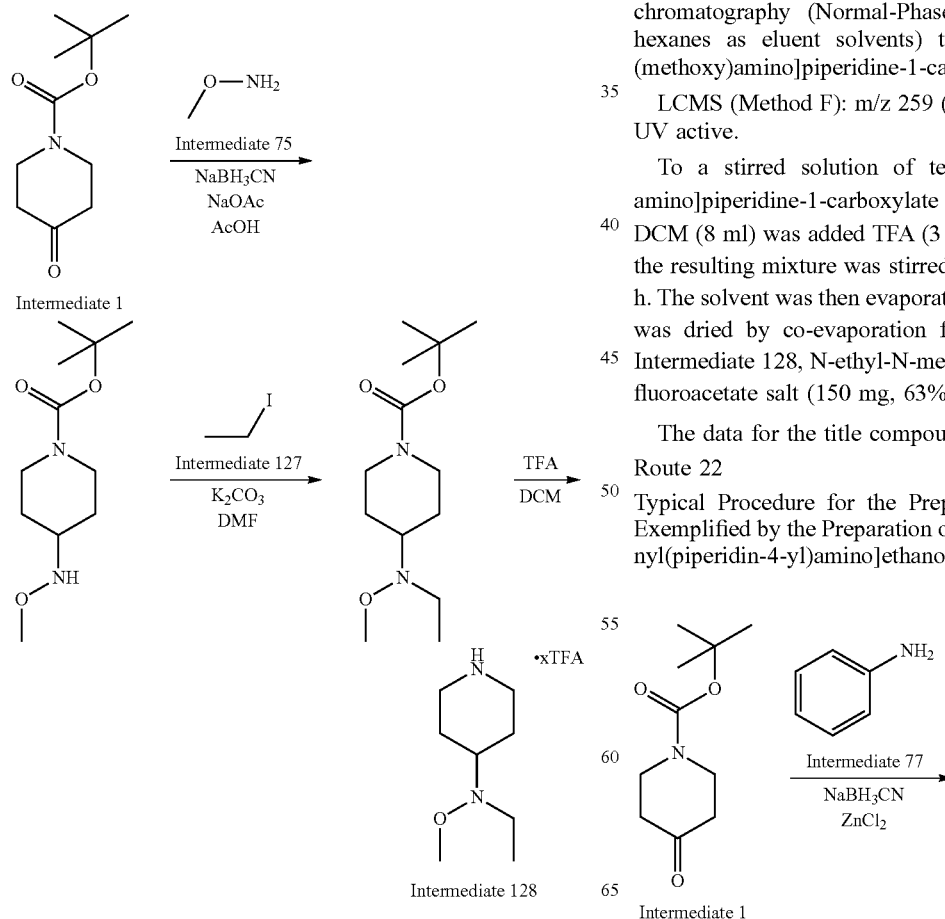

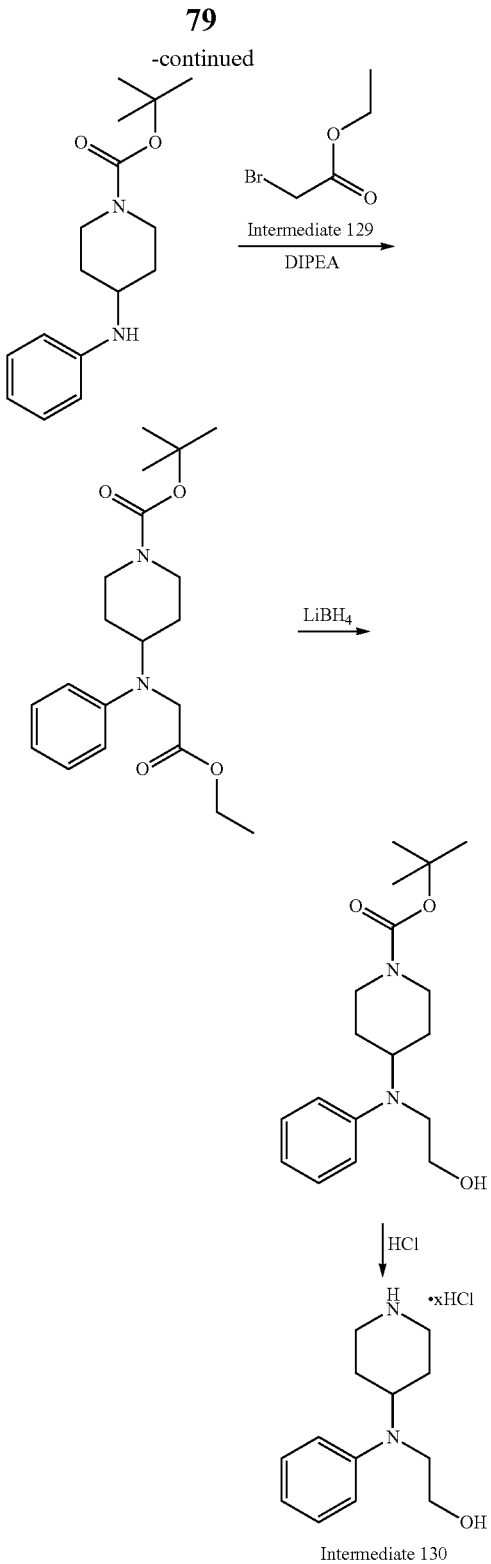

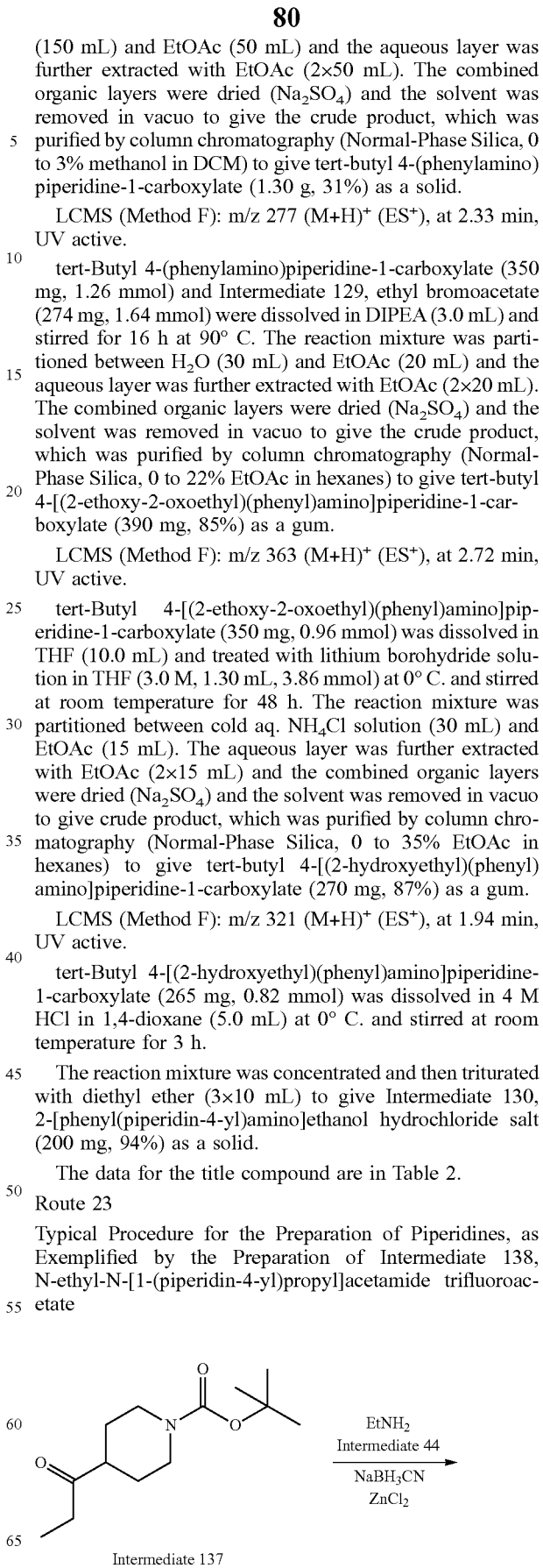

Intermediate 130

Intermediate 1, tert-butyl 4-oxopiperidine-1-carboxylate (3.00 g, 15.0 mmol), Intermediate 77, aniline (1.40 g, 15.0 mmol), triethylamine (6.35 mL, 45.0 mmol) and zinc chloride (0.75 mL, 0.75 mmol) were dissolved in methanol (25.0 mL) under nitrogen and stirred at 50-60° C. for 16 h. NaCNBH$_3$ (2.84 g, 45.0 mmol) was added portionwise at 0-10° C. and the resulting mixture was stirred at 50-60° C. for 16 h. The reaction mixture was partitioned between H$_2$O (150 mL) and EtOAc (50 mL) and the aqueous layer was further extracted with EtOAc (2×50 mL). The combined organic layers were dried (Na$_2$SO$_4$) and the solvent was removed in vacuo to give the crude product, which was purified by column chromatography (Normal-Phase Silica, 0 to 3% methanol in DCM) to give tert-butyl 4-(phenylamino)piperidine-1-carboxylate (1.30 g, 31%) as a solid.

LCMS (Method F): m/z 277 (M+H)$^+$ (ES$^+$), at 2.33 min, UV active.

tert-Butyl 4-(phenylamino)piperidine-1-carboxylate (350 mg, 1.26 mmol) and Intermediate 129, ethyl bromoacetate (274 mg, 1.64 mmol) were dissolved in DIPEA (3.0 mL) and stirred for 16 h at 90° C. The reaction mixture was partitioned between H$_2$O (30 mL) and EtOAc (20 mL) and the aqueous layer was further extracted with EtOAc (2×20 mL). The combined organic layers were dried (Na$_2$SO$_4$) and the solvent was removed in vacuo to give the crude product, which was purified by column chromatography (Normal-Phase Silica, 0 to 22% EtOAc in hexanes) to give tert-butyl 4-[(2-ethoxy-2-oxoethyl)(phenyl)amino]piperidine-1-carboxylate (390 mg, 85%) as a gum.

LCMS (Method F): m/z 363 (M+H)$^+$ (ES$^+$), at 2.72 min, UV active.

tert-Butyl 4-[(2-ethoxy-2-oxoethyl)(phenyl)amino]piperidine-1-carboxylate (350 mg, 0.96 mmol) was dissolved in THF (10.0 mL) and treated with lithium borohydride solution in THF (3.0 M, 1.30 mL, 3.86 mmol) at 0° C. and stirred at room temperature for 48 h. The reaction mixture was partitioned between cold aq. NH$_4$Cl solution (30 mL) and EtOAc (15 mL). The aqueous layer was further extracted with EtOAc (2×15 mL) and the combined organic layers were dried (Na$_2$SO$_4$) and the solvent was removed in vacuo to give crude product, which was purified by column chromatography (Normal-Phase Silica, 0 to 35% EtOAc in hexanes) to give tert-butyl 4-[(2-hydroxyethyl)(phenyl)amino]piperidine-1-carboxylate (270 mg, 87%) as a gum.

LCMS (Method F): m/z 321 (M+H)$^+$ (ES$^+$), at 1.94 min, UV active.

tert-Butyl 4-[(2-hydroxyethyl)(phenyl)amino]piperidine-1-carboxylate (265 mg, 0.82 mmol) was dissolved in 4 M HCl in 1,4-dioxane (5.0 mL) at 0° C. and stirred at room temperature for 3 h.

The reaction mixture was concentrated and then triturated with diethyl ether (3×10 mL) to give Intermediate 130, 2-[phenyl(piperidin-4-yl)amino]ethanol hydrochloride salt (200 mg, 94%) as a solid.

The data for the title compound are in Table 2.

Route 23

Typical Procedure for the Preparation of Piperidines, as Exemplified by the Preparation of Intermediate 138, N-ethyl-N-[1-(piperidin-4-yl)propyl]acetamide trifluoroacetate

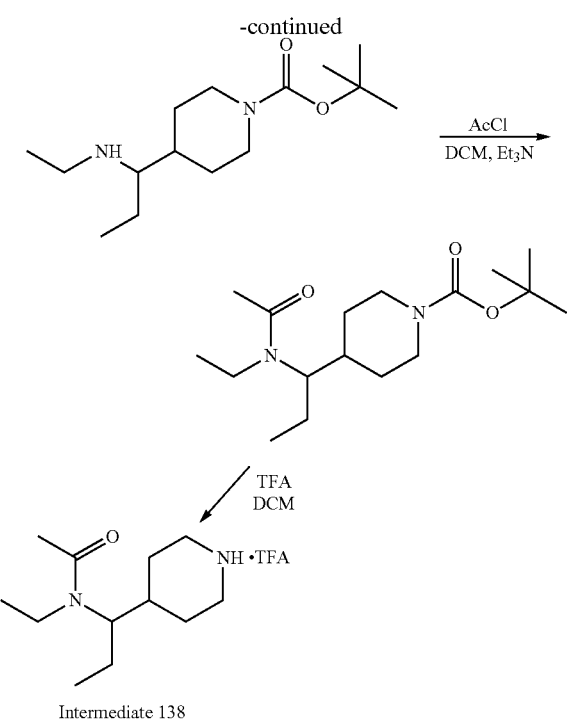

Intermediate 138

Intermediate 137, tert-butyl 4-propanoylpiperidine-1-carboxylate (450 mg, 1.86 mmol), Intermediate 44, ethanamine (2.0 M solution in THF, 2.33 mL, 4.66 mmol), Et₃N (0.780 mL, 5.60 mmol), ZnCl₂ (0.2 mL) and MeOH (10 mL) were charged into a vial. The reaction mixture was heated at 60° C. for 4 h then the reaction mixture was cooled to 0° C. and NaCNBH₃ (351 mg, 5.60 mmol) was added. The reaction mixture was allowed to warm to room temperature and was stirred for 16 h. The reaction mixture was concentrated in vacuo and the residue was partitioned between H₂O (100 mL) and EtOAc (100 mL). The aqueous layer was further extracted with EtOAc (2×50 mL) and the combined organic layers were dried (Na₂SO₄) and the solvent was removed in vacuo to give the crude product, which was purified by combi-flash column chromatography (Normal phase, Neutral silica gel, 60-120 mesh, 0 to 1% MeOH in DCM) to give tert-butyl 4-[1-(ethylamino)propyl]piperidine-1-carboxylate (440 mg, 87%) as a gum.

LCMS (Method F): m/z 271 (M+H)$^+$ (ES$^+$), at 5.34 min, UV active.

tert-Butyl 4-[1-(ethylamino)propyl]piperidine-1-carboxylate (435 mg, 1.61 mmol) was dissolved in DCM (10 mL) and triethylamine (0.67 mL, 4.83 mmol) was added dropwise at 0-5° C. The reaction mixture was stirred at 0-5° C. for 10 min then acetyl chloride (0.17 mL, 2.41 mmol) was added dropwise at 0-5° C. The resulting reaction mixture was stirred at 25° C. for 8 h, then the solvents were removed in vacuo. The residue was partitioned between H₂O (50 mL) and DCM (50 mL) and the aqueous layer was further extracted with DCM (2×30 mL). The combined organic layers were dried (Na₂SO₄) and the solvents were removed in vacuo. The residue was purified by column chromatography (Normal basic activated alumina, at 0.5% to 1.0% MeOH in DCM) to give tert-butyl 4-{1-[acetyl(ethyl)amino]propyl}piperidine-1-carboxylate (415 mg, 63%) as a gum.

LCMS (Method I): m/z 313 (M+H)$^+$ (ES$^+$), at 4.53 min, UV active.

tert-Butyl 4-{1-[acetyl(ethyl)amino]propyl}piperidine-1-carboxylate (415 mg, 1.33 mmol) was dissolved in DCM (5.0 mL) at 0° C. and TFA (2.5 mL) was added to the solution at 0° C. The reaction mixture was allowed to warm at room temperature and was stirred for 6 h. The reaction mixture was then concentrated and dried by co-evaporation from diethyl ether (3×5 mL) to give Intermediate 138, N-ethyl-N-[1-(piperidin-4-yl)propyl]acetamide trifluoroacetate salt (250 mg, 80%) as a gum.

The data for the title compound are in Table 2.

Route 24

Typical Procedure for the Preparation of Piperidines, as Exemplified by the Preparation of Intermediate 140, N-ethyl-N-[2-(piperidin-4-yl)propan-2-yl]acetamide hydrochloride

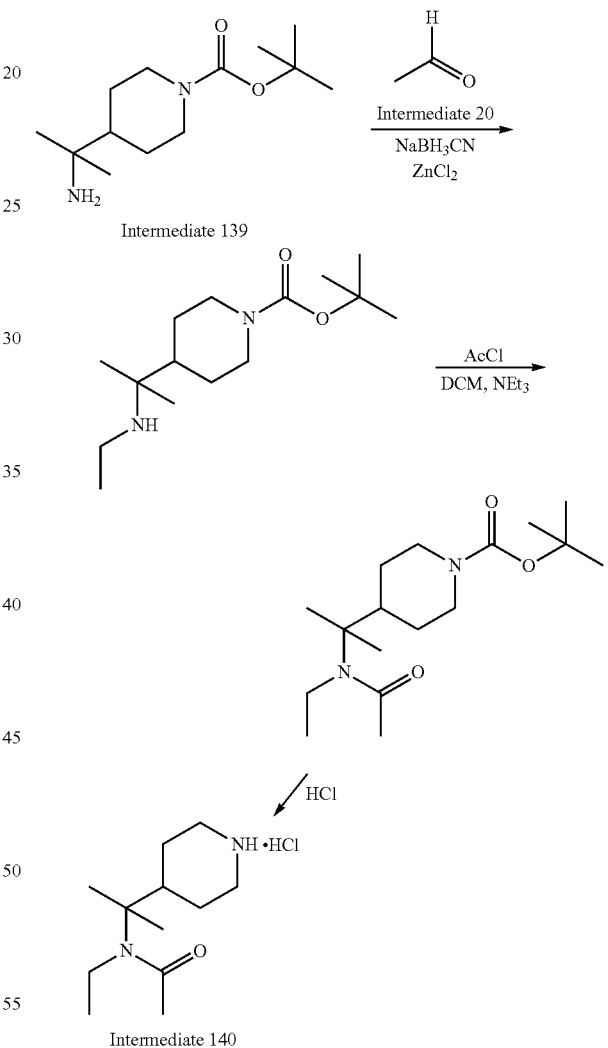

Intermediate 140

Intermediate 139, tert-butyl 4-(2-aminopropan-2-yl)piperidine-1-carboxylate (300 mg, 1.24 mmol), Intermediate 20, acetaldehyde (163 mg, 3.71 mmol), triethylamine (0.52 mL, 3.71 mmol) and zinc chloride (0.06 mL, 0.06 mmol) were dissolved in methanol (10 mL) under nitrogen and stirred for 16 h at 50-60° C. After 16 h, NaCNBH₃ (233 mg, 3.74 mmol) was added portionwise at 0-10° C. and the resulting mixture was stirred for 6 h at 50-60° C. The reaction mixture was partitioned between H₂O (40 mL) and EtOAc (25 mL) and the aqueous layer was further extracted with EtOAc (2×25 mL). The combined organic layers were dried (Na$_2$SO$_4$) and the solvent was removed in vacuo to give the crude product, which was purified by column chromatography (Normal-Phase Silica, 0 to 4% MeOH in DCM) to give tert-butyl 4-[2-(ethylamino)propan-2-yl]piperidine-1-carboxylate (180 mg, 54%) as a gum.

LCMS (Method F): m/z 271 (M+H)$^+$ (ES$^+$), at 1.71 min, UV active.

tert-butyl 4-[2-(ethylamino)propan-2-yl]piperidine-1-carboxylate (180 mg, 0.66 mmol) and triethylamine (0.27 mL, 19.9 mmol) were dissolved in dry DCM (5.0 mL) under nitrogen. Acetyl chloride (78.0 mg, 0.99 mmol) was added at 0° C. and the resulting mixture was stirred for 30 min at room temperature. The reaction mixture was then partitioned between sat. aq. NaHCO$_3$ solution (20 mL) and EtOAc (15 mL) and the aqueous layer was further extracted with EtOAc (2×25 mL). The combined organic layers were dried (Na$_2$SO$_4$) and the solvent was removed in vacuo to give the crude product, which was purified by column chromatography (Normal-Phase Silica, 0 to 65% EtOAc in hexanes) to give tert-butyl 4-{2-[acetyl(ethyl)amino]propan-2-yl}piperidine-1-carboxylate (160 mg, 77%) as a gum.

LCMS (Method I): m/z 257 (M+H-56)$^+$ (ES$^+$), at 4.75 min, UV active.

tert-butyl 4-{2-[acetyl(ethyl)amino]propan-2-yl}piperidine-1-carboxylate (160 mg, 0.51 mmol) and 4 M HCl in 1,4-dioxane (5 mL) were dissolved in 1,4-dioxane (5 mL) under nitrogen and stirred together for 3 h at room temperature. The reaction mixture was poured into toluene and then triturated with diethyl ether (2×5 mL) and concentrated in vacuo to give Intermediate 140, N-ethyl-N-[2-(piperidin-4-yl)propan-2-yl]acetamide hydrochloride salt (110 mg, 95%) as a solid.

The data for the title compound are in Table 2.

Route 25

Typical Procedure for the Preparation of Piperidines, as Exemplified by the Preparation of Intermediate 144, 4-[1-(1H-pyrazol-1-yl)ethyl]piperidine trifluoroacetate

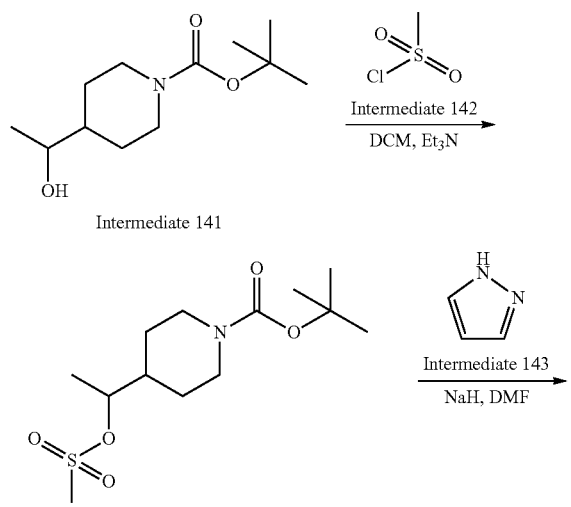

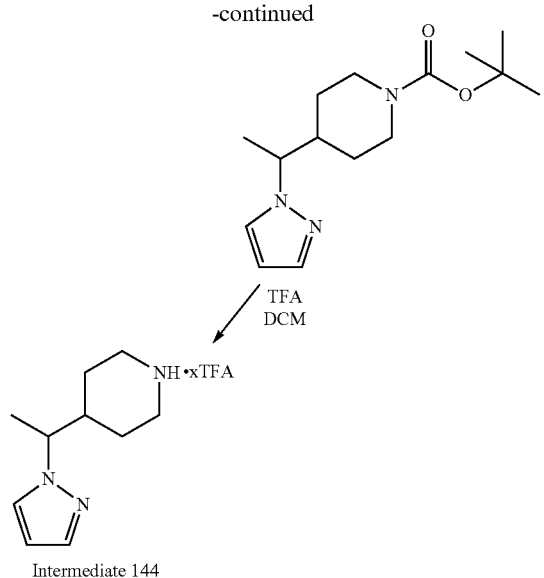

Intermediate 144

Intermediate 141, tert-butyl 4-(1-hydroxyethyl)piperidine-1-carboxylate (2.0 g, 8.73 mmol) and Et$_3$N (3.64 mL, 26.3 mmol) were dissolved in dichloromethane (20.0 mL) and cooled to 0° C. Intermediate 142, methanesulfonyl chloride (0.82 mL, 10.4 mmol) was added dropwise and the reaction mixture was allowed to stir at 0° C. for 2 h. The reaction mixture was diluted with water (100 mL) and extracted with DCM (2×30 mL). The combined organic layers were dried (Na$_2$SO$_4$) and concentrated in vacuo to give crude tert-butyl 4-{1-[(methylsulfonyl)oxy]ethyl}piperidine-1-carboxylate (2.0 g, 75%) as an oil. The crude product was used in the next step without further purification.

LCMS (Method I): m/z 252 (M+H-56)$^+$ (ES$^+$), at 4.51 min, UV active.

Intermediate 143, 1H-pyrazole (887 mg, 13.03 mmol) was dissolved in DMF (15.0 mL) and cooled to 0° C. 60% sodium hydride suspension in mineral oil (281 mg, 7.0 mmol) was added and the mixture was allowed to stir at 0° C. for 1 h. After the completion of 1 h, tert-butyl 4-{1-[(methylsulfonyl)oxy]ethyl}piperidine-1-carboxylate (2.0 g, 6.51 mmol) in DMF (1.0 mL) was added dropwise at 0° C. and the reaction mixture was stirred at room temperature for 16 h. The mixture was diluted with water (100 mL) and extracted with DCM (2×30 mL). The combined organic layers were dried (Na$_2$SO$_4$) and concentrated in vacuo to give the crude product, which was purified by column chromatography (Normal phase, Neutral silica gel, 60-120 mesh, 0 to 30% EtOAc in hexane) to give tert-butyl 4-[1-(1H-pyrazol-1-yl)ethyl]piperidine-1-carboxylate (430 mg, 24%) as a gum.

LCMS (Method I): m/z 280 (M+H)$^+$ (ES$^+$), at 4.51 min, UV active.

tert-Butyl 4-[1-(1H-pyrazol-1-yl)ethyl]piperidine-1-carboxylate (430 mg, 1.54 mmol) was dissolved in dichloromethane (8.0 mL) and cooled to 0° C. TFA (4.0 mL) was added and the reaction mixture was stirred at room temperature for 2 h. The reaction mixture was then concentrated in vacuo to give crude Intermediate 144, 4-[1-(1H-pyrazol-1-yl)ethyl]piperidine trifluoroacetate salt (450 mg, 100%) as a gum, which was used without further purification.

The data for the title compound are in Table 2.

Route 26

Typical Procedure for the Preparation of Piperidines, as Exemplified by the Preparation of Intermediate 147, 4-(1-phenylethoxy)piperidine hydrochloride Route 27

Typical Procedure for the Preparation of Piperidines, as Exemplified by the Preparation of Intermediate 150, 4-(benzylsulfanyl)piperidine hydrochloride

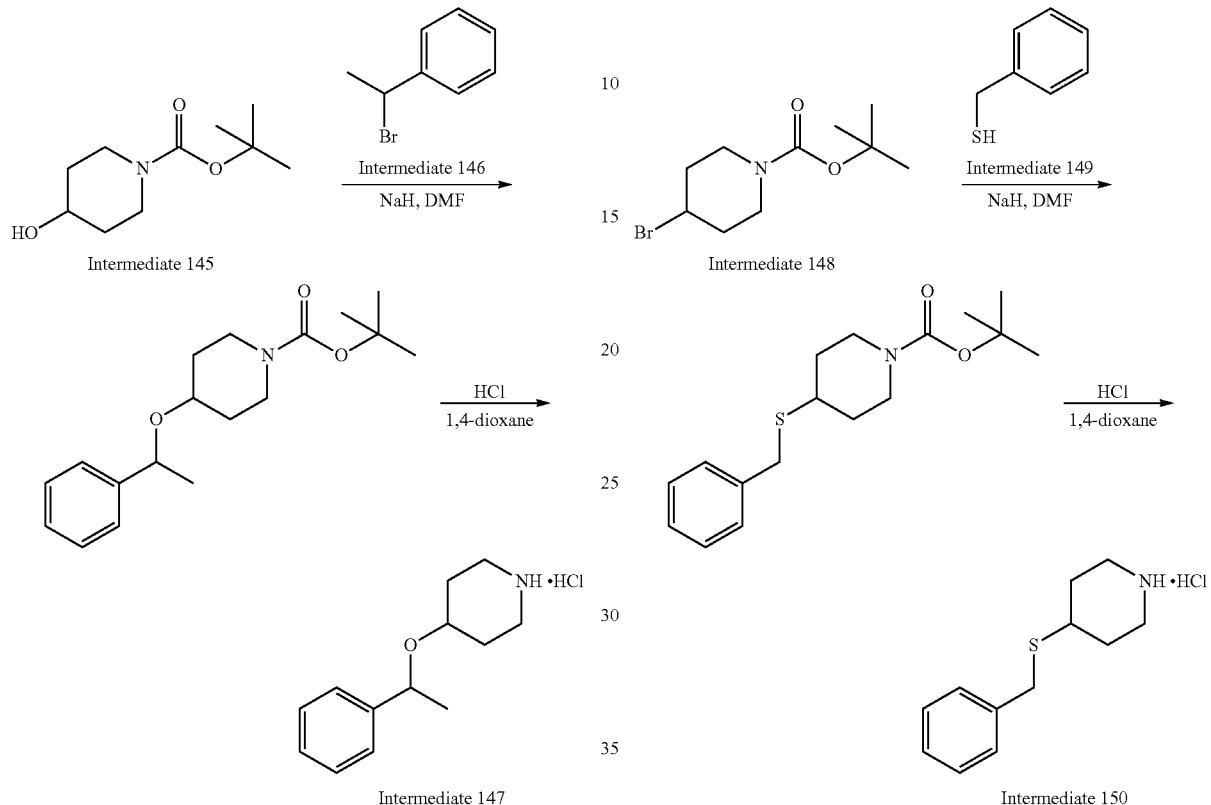

Intermediate 145, tert-butyl 4-hydroxypiperidine-1-carboxylate (543 mg, 2.69 mmol) was dissolved in DMF (10 mL), 60% sodium hydride suspension in mineral oil (183 mg, 4.58 mmol) was added portionwise under nitrogen at 0° C. and the mixture was stirred at room temperature for 1 h. After 1 h, Intermediate 146, (1-bromoethyl)benzene (500 mg, 2.69 mmol) was added dropwise and the resulting mixture was stirred for 16 h at 90° C. The reaction mixture was partitioned between H$_2$O (50 mL) and EtOAc (25 mL) and the aqueous layer was further extracted with EtOAc (2×25 mL). The organic layers were combined, dried (Na$_2$SO$_4$) and the solvent was removed in vacuo to give the crude product, which was purified by column chromatography (Normal-Phase Silica, 0 to 15% EtOAc in hexanes) to give tert-butyl 4-(1-phenylethoxy)piperidine-1-carboxylate (161 mg, 20%) as a gum.

LCMS (Method F): m/z 306 (M+H)$^+$ (ES$^+$), at 2.79 min, UV active.

tert-Butyl 4-(1-phenylethoxy)piperidine-1-carboxylate (160 mg, 5.27 mmol) was dissolved in 4 M HCl in 1,4-dioxane (5 mL) at 0° C. and stirred at room temperature for 3 h. The reaction mixture was concentrated and the residue was triturated with diethyl ether (3×10 mL) to give Intermediate 147, 4-(1-phenylethoxy)piperidine hydrochloride salt (100 mg, 89%) as a solid.

The data for the title compound are in Table 2.

Intermediate 149, phenylmethanethiol (9.6 mL, 81.8 mmol) was dissolved in DMF (80 mL), 60% sodium hydride suspension in mineral oil (3.27 g, 81.8 mmol) was added portionwise under nitrogen at 0° C. and the resulting mixture was stirred at room temperature for 30 min. After 30 min, Intermediate 148, tert-butyl 4-bromopiperidine-1-carboxylate (5.4 g, 20.4 mmol) was added dropwise and the resulting mixture was stirred for 16 h at room temperature. The reaction mixture was partitioned between H$_2$O (150 mL) and EtOAc (50 mL) and the aqueous layer was further extracted with EtOAc (2×50 mL). The combined organic layers were dried (Na$_2$SO$_4$) and the solvent was removed in vacuo to give the crude product, which was purified by column chromatography (Normal-Phase Silica, 0 to 12% EtOAc in hexanes) to give tert-butyl 4-(benzylsulfanyl)piperidine-1-carboxylate (1.59 g, 25%) as a gum.

LCMS (Method F): m/z 252 (M+H-56)$^+$ (ES$^+$), at 2.73 min, UV active.

tert-Butyl 4-(benzylsulfanyl)piperidine-1-carboxylate (1.00 g, 3.25 mmol) was dissolved in 4 M HCl in 1,4-dioxane (10 mL) at 0° C. and stirred at room temperature for 3 h. The reaction mixture was concentrated and the residue was triturated with diethyl ether (3×10 mL) to give Intermediate 150, 4-(benzylsulfanyl)piperidine hydrochloride salt (750 mg, 95%) as a gum.

The data for the title compound are in Table 2.

Route 28
Procedure for the Preparation of Intermediate 152, methyl 6-oxo-2-azaspiro[3.4]octane-2-carboxylate

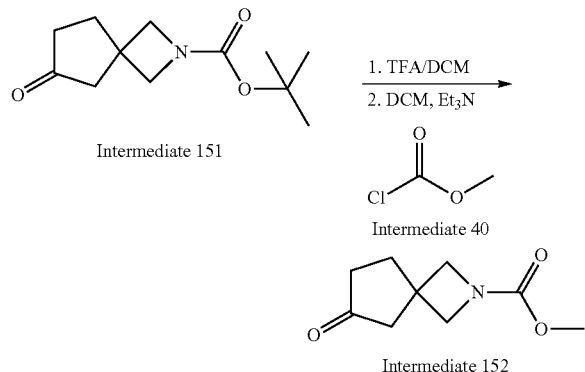

Intermediate 151, tert-butyl 6-oxo-2-azaspiro[3.4]octane-2-carboxylate (120 mg, 0.533 mmol) was dissolved in DCM (2.0 mL) at 0° C. and TFA (1.0 mL) was added. The reaction mixture was allowed to warm to room temperature and was stirred for 2 h, then concentrated in vacuo. The residue was dried by co-evaporation from diethyl ether (3×10 mL) to give 2-azaspiro[3.4]octan-6-one trifluoroacetate salt (120 mg, 100%) as a gum.

LCMS (Method I): m/z 125 (M+H)$^+$ (ES$^+$), at 0.60 min, UV active.

2-Azaspiro[3.4]octan-6-one trifluoroacetate salt (60 mg, 0.251 mmol) was dissolved in DCM (5 mL) and triethylamine (0.2 mL, 1.25 mmol) was added at 0° C. Intermediate 40, methyl carbonochloridate (94.4 mg, 0.37 mmol) was added at 0° C. and the reaction mixture was allowed to warm to room temperature and was stirred for 2 h. The mixture was concentrated in vacuo and the residue was partitioned between H$_2$O (25 mL) and EtOAc (25 mL). The aqueous layer was further extracted with EtOAc (2×10 mL) and the combined organic layers were dried (Na$_2$SO$_4$) and the solvent was removed in vacuo to give Intermediate 152, methyl 6-oxo-2-azaspiro[3.4]octane-2-carboxylate (30 mg, 34%) as an oil.

The data for the title compound are in Table 2.

General Synthetic Procedures for the Examples

Route a

Typical Procedure for the Preparation of Piperidines Via Reductive Amination, as Exemplified by the Preparation of Example 2-2, Ethyl 2-{4-[acetyl(ethyl)amino]piperidin-1-yl}-6-azaspiro[3.4]octane-6-carboxylate

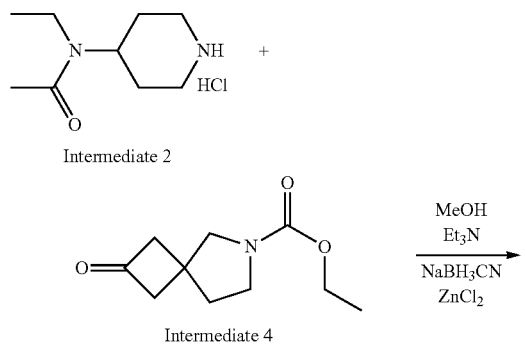

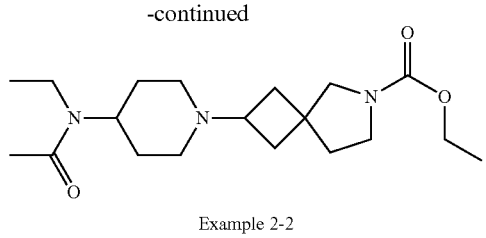

Intermediate 2, N-ethyl-N-(piperidin-4-yl)acetamide hydrochloride (150 mg, 0.9 mmol), Intermediate 4, ethyl 2-oxo-6-azaspiro[3.4]octane-6-carboxylate (170 mg, 0.9 mmol), Et$_3$N (0.24 mL, 1.9 mmol) and ZnCl$_2$ (6 mg) were dissolved in MeOH (10 mL) and the reaction mixture was stirred at 60° C. for 8 h. The mixture was then cooled to 0° C. and NaBH$_3$CN (72 mg, 1.2 mmol) was added portion-wise, after which the mixture was stirred at 25° C. for 17 h. The solvent was removed in vacuo, and the residue was partitioned between H$_2$O (100 mL) and EtOAc (80 mL). The aqueous layer was further extracted with EtOAc (2×80 mL) and the combined organic phases were dried (Na$_2$SO$_4$) and the solvent was removed in vacuo. The residue was purified by prep. HPLC [reverse phase (X-BRIDGE C-18, 150×19 mm, 5 µm, 15 mL per min, gradient 25% to 100% (over 20 min), 100% (over 3 min), then 30% (over 2 min), 0.1% NH$_3$ in MeCN/water] to give Example 2-2 Isomer 1, ethyl 2-{4-[acetyl(ethyl)amino]piperidin-1-yl}-6-azaspiro[3.4]octane-6-carboxylate (30 mg, 9%) as a gum and Example 2-2 Isomer 2, ethyl 2-{4-[acetyl(ethyl)amino]piperidin-1-yl}-6-azaspiro[3.4]octane-6-carboxylate (25 mg, 7%) as a gum.

The data for Example 2-2 Isomer 2 are in Table 3.

Route b

Typical Procedure for the Preparation of Piperidines Via Sodium Triacetoxyborohydride Reductive Amination as Exemplified by the Preparation of Example 2-12, ethyl 2-(4-{[acetyl(cyclopropyl)amino]methyl}piperidin-1-yl)-6-azaspiro[3.4]octane-6-carboxylate

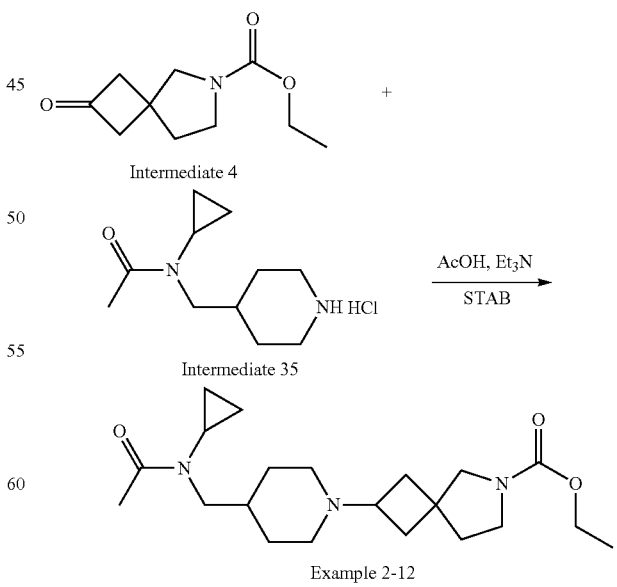

Intermediate 4, ethyl 2-oxo-6-azaspiro[3.4]octane-6-carboxylate (99 mg, 0.5 mmol) and Intermediate 35, N-cyclopropyl-N-(piperidin-4-ylmethyl)acetamide hydrochloride (116 mg, 0.5 mmol) were dissolved in DCM (10 mL) at rt and Et₃N (0.35 mL, 2.5 mmol) was added. The mixture was stirred for 30 min before addition of AcOH (0.29 mL, 5.0 mmol). The mixture was stirred for 3 h, then STAB (265 mg, 1.3 mmol) was added and the mixture was stirred at rt overnight. The reaction mixture was quenched with the addition of sat. aq. NaHCO₃ (20 mL), and solid Na₂CO₃ was added to ensure the aqueous layer was basic. The resulting mixture was extracted with DCM (4×20 mL) and the organic layers were combined, dried (MgSO₄), filtered and the solvents were removed in vacuo. The residue was purified by column chromatography (normal phase, [Biotage SNAP cartridge KP-sil 10 g, 40-63 µm, 60 Å, 20 mL per min, gradient 0% to 10% MeOH in DCM]) to give an inseparable mixture of diastereoisomers. This mixture was purified by preparative reversed phase HPLC (Phenomenex Gemini-NX 5 µm C18 110A Axia column, 100×30 mm, eluting with 30 to 60% MeCN/Solvent B over 14.4 min at 30 mL/min [where solvent B is 0.2% of (28% NH₃/H₂O) in H₂O] and collecting fractions by monitoring at 205 nm) to give Example 2-12 Isomer 1, ethyl 2-(4-{[acetyl(cyclopropyl)amino]methyl}piperidin-1-yl)-6-azaspiro[3.4]octane-6-carboxylate (42 mg, 22%) as a solid and Example 2-12 Isomer 2 ethyl 2-(4-{[acetyl(cyclopropyl)amino]methyl}piperidin-1-yl)-6-azaspiro[3.4]octane-6-carboxylate (36 mg, 19%) as a solid.

The data for Example 2-12 Isomer 2 are in Table 3.
Route c
Typical Procedure for the Preparation of Piperidines Via Use of a Protected Ketone as Exemplified by the Preparation of Example 2-23, ethyl 2-(4-{acetyl[(3-methyloxetan-3-yl)methyl]amino}piperidin-1-yl)-6-azaspiro[3.4]octane-6-carboxylate Intermediate 57, 1,4-dioxa-8-azaspiro[4.5]decane (1.0 g, 6.99 mmol) was dissolved in methanol (20 mL) and Intermediate 4, ethyl 2-oxo-6-azaspiro[3.4]octane-6-carboxylate (1.38 g, 6.99 mmol), triethylamine (2.9 mL, 20.9 mmol) and ZnCl₂ (95 mg, 0.70 mmol) were added and then the reaction mixture was stirred at 65° C. for 8 h. NaBH₃CN (1.32 g, 20.9 mmol) was added portionwise and the resulting reaction mixture was stirred at 25° C. for 17 h. The solvents were removed in vacuo, and the residue was partitioned between H₂O (120 mL) and EtOAc (100 mL). The aqueous layer was further extracted with EtOAc (2×100 mL), the organic layers were combined, dried (Na₂SO₄) and the solvent was removed in vacuo. The residue was purified by triturating with pentane and decanting off the solvents to give ethyl 2-(1,4-dioxa-8-azaspiro[4.5]dec-8-yl)-6-azaspiro[3.4]octane-6-carboxylate (1.80 g, 79%) as a gum.

LCMS (Method I): m/z 325 (M+H)⁺ (ES⁺), at 3.54 and 3.69 min, UV active.

Ethyl 2-(1,4-dioxa-8-azaspiro[4.5]dec-8-yl)-6-azaspiro[3.4]octane-6-carboxylate (1.80 g, 5.55 mmol) was dissolved in ethanol (20 mL) and 4.0 M HCl in 1,4-dioxane (30 mL) was added. The resulting reaction mixture was stirred at 70° C. for 18 h and then basified with sat. sodium bicarbonate solution. The solvents were removed in vacuo and the residue was partitioned between H₂O (100 mL) and EtOAc (80 mL). The aqueous layer was further extracted with EtOAc (2×80 mL) and the combined organic layers were dried (Na₂SO₄). The solvent was removed in vacuo and the residue was triturated with pentane to give ethyl 2-(4-oxopiperidin-1-yl)-6-azaspiro[3.4]octane-6-carboxylate (1.20 g, 77%) as a gum.

LCMS (Method I): m/z 281 (M+H)⁺ (ES⁺), at 3.30 and 3.41 min, UV active.

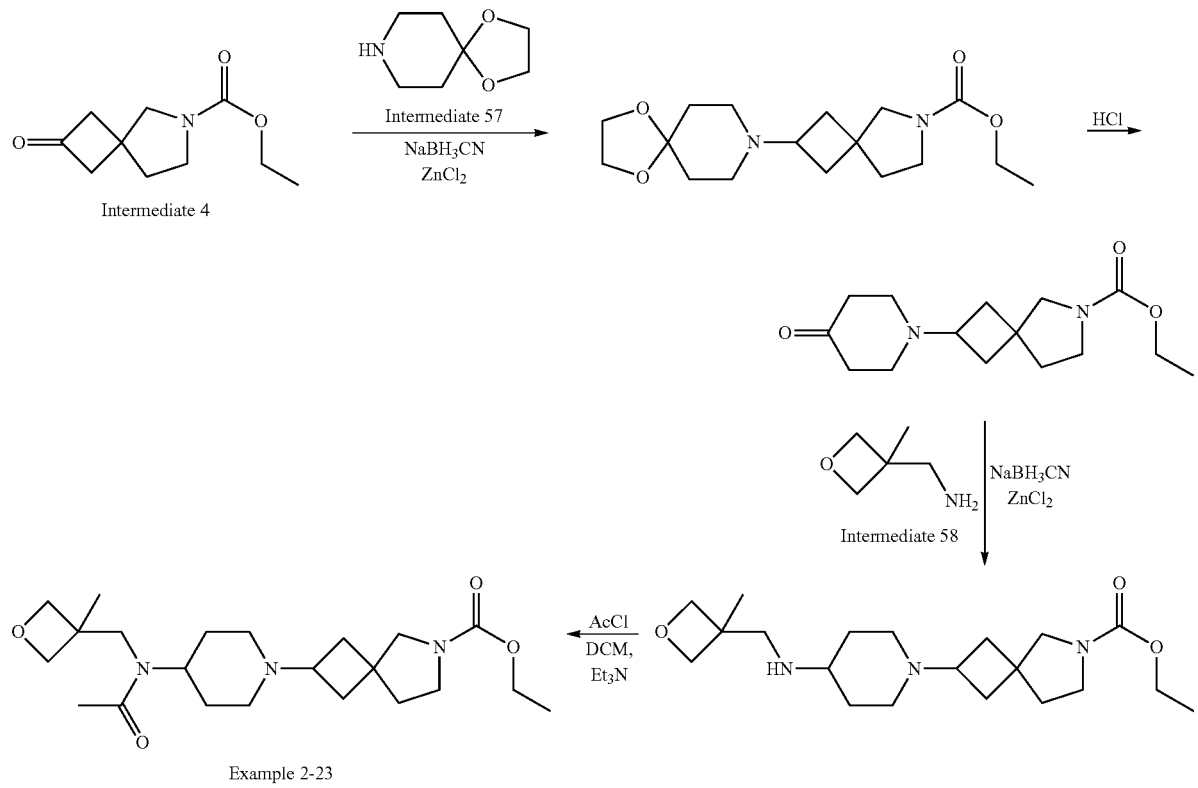

Example 2-23

Intermediate 58, 1-(3-methyloxetan-3-yl)methanamine (72 mg, 0.72 mmol), ethyl 2-(4-oxopiperidin-1-yl)-6-azaspiro[3.4]octane-6-carboxylate (200 mg, 0.71 mmol), triethylamine (0.4 mL, 2.85 mmol) and ZnCl$_2$ (9 mg, 0.07 mmol) were dissolved in MeOH (10 mL) and the reaction mixture was stirred at 65° C. for 8 h. The mixture was cooled to 0° C. and NaBH$_3$CN (134 mg, 2.14 mmol) was added portionwise. The resulting reaction mixture was stirred at 25° C. for 17 h. The solvents were removed in vacuo and the residue was partitioned between H$_2$O (80 mL) and EtOAc (60 mL). The aqueous layer was further extracted with EtOAc (2×60 mL) and the combined organic layers were dried (Na$_2$SO$_4$) and the solvent was removed in vacuo.

The residue was purified by triturating with pentane (3×1 mL) to give ethyl 2-(4-{[(3-methyloxetan-3-yl)methyl] amino}piperidin-1-yl)-6-azaspiro[3.4]octane-6-carboxylate (210 mg, 81%) as a gum.

LCMS (Method I): m/z 366 (M+H)$^+$ (ES$^+$), at 3.63 and 3.81 min, UV active.

bicarbonate+0.1% ammonia in water and (B) 100% acetonitrile] to give Example 2-23 Isomer 1, ethyl 2-(4-{acetyl[(3-methyloxetan-3-yl)methyl]amino}piperidin-1-yl)-6-azaspiro[3.4]octane-6-carboxylate (47 mg, 21%) as a liquid and Example 2-23 Isomer 2, ethyl 2-(4-{acetyl[(3-methyloxetan-3-yl)methyl]amino}piperidin-1-yl)-6-azaspiro[3.4] octane-6-carboxylate (45 mg, 20%) as a liquid.

The data for Example 2-23 Isomer 2 are in Table 3.

Route d

Typical Procedure for the Preparation of Piperidines Via Nucleophilic Displacement on a 4-nitrophenyl carbamate as exemplified by the preparation of Example 2-38, (1,1-$^2$H$_2$)-ethyl 2-{4-[acetyl(ethyl)amino]piperidin-1-yl}-6-azaspiro [3.4]octane-6-carboxylate

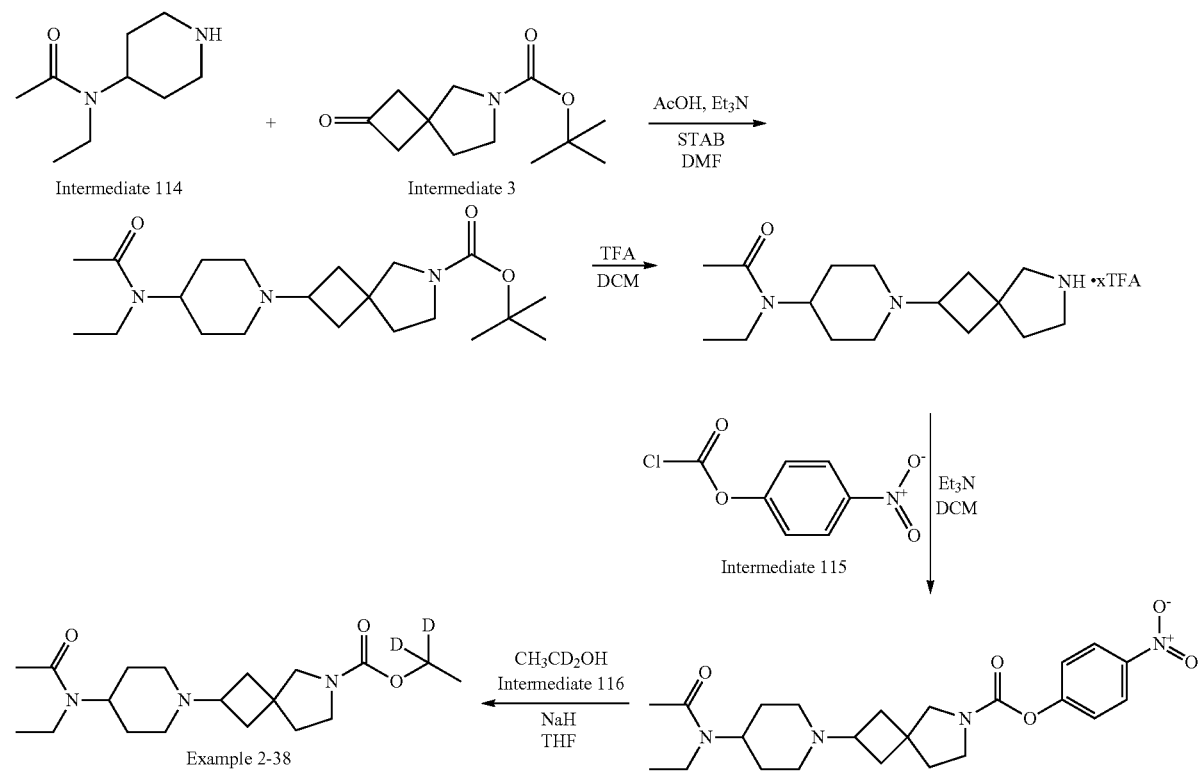

Ethyl 2-(4-{[(3-methyloxetan-3-yl)methyl] amino}piperidin-1-yl)-6-azaspiro[3.4]octane-6-carboxylate (200 mg, 0.55 mmol) was dissolved in DCM (10 mL), triethylamine (0.2 mL, 1.64 mmol) was added and the reaction mixture was stirred at 0° C. for 20 min. Acetyl chloride (0.06 mL, 0.82 mmol) was added portionwise and the resulting reaction mixture was stirred at 25° C. for 2 h. The solvents were removed in vacuo, the residue was partitioned between H$_2$O (80 mL) and EtOAc (60 mL) and the aqueous layer was further extracted with EtOAc (2×60 mL). The combined organic layers were dried (Na$_2$SO$_4$), the solvent was removed in vacuo and the residue was purified by preparative HPLC [reverse phase (X-BRIDGE C18, 250×19 mm, 5 μm, 15 mL per min, gradient 5% to 30% (over 36 min), 30% (over 9 min), 100% (over 5 min), then 5% (over 5 min), mobile phase (A) 5 mM ammonium Intermediate 114, N-ethyl-N-(piperidin-4-yl)acetamide (1.70 g, 10 mmol) and Intermediate 3, tert-butyl 2-oxo-6-azaspiro[3.4]octane-6-carboxylate (2.25 g, 10 mmol) were mixed in DMF (40 mL) under an atmosphere of nitrogen. AcOH (0.86 mL, 15 mmol) and STAB (4.24 g, 20 mmol) were added and the resulting mixture was stirred at rt for 6 d. The mixture was concentrated to remove DMF and the residue was treated with toluene and concentrated to remove AcOH. The residue was dissolved in MeOH and concentrated onto flash silica (15 mL). The resulting powder was purified by column chromatography (normal phase, [Biotage SNAP cartridge KP-sil 100 g, 40-63 μm, 60 Å, 40 mL per min, gradient 0% to 10% Solvent A in DCM over 15 CV, where Solvent A is 10% of {7 M NH$_3$ in MeOH} in MeOH])

to give tert-butyl 2-{4-[acetyl(ethyl)amino]piperidin-1-yl}-6-azaspiro[3.4]octane-6-carboxylate as a gum (2.92 g, 77%).

LCMS (Method D): m/z 380 (M+H)⁺ (ES⁺), at 2.11 min, UV active.

tert-Butyl 2-{4-[acetyl(ethyl)amino]piperidin-1-yl}-6-azaspiro[3.4]octane-6-carboxylate (2.80 g, 7.38 mmol) was dissolved in a mixture of DCM (50 mL) and TFA (50 mL) under an atmosphere of nitrogen and stirred ar rt for 3.5 h. The mixture was diluted with toluene and concentrated. The oily residue was diluted with toluene and concentrated to afford N-[1-(6-azaspiro[3.4]oct-2-yl)piperidin-4-yl]-N-ethylacetamide trifluoroacetate salt as a gum (5.73 g, assumed 100%).

LCMS (Method D): m/z 280 (M+H)⁺ (ES⁺), at 1.67 and 1.79 min, weakly UV active.

N-[1-(6-Azaspiro[3.4]oct-2-yl)piperidin-4-yl]-N-ethylacetamide trifluoroacetate salt (5.73 g, assumed 7.38 mmol) was dissolved in DCM (140 mL) under an atomosphere of nitrogen. Et₃N (5.1 ml, 36.6 mmol) and Intermediate 115, 4-nitrophenyl carbonochloridate (1.78 g, 8.83 mmol) were added and the resulting mixture was stirred at rt overnight. More Et₃N (2 ml, 14.3 mmol) and Intermediate 115, 4-nitrophenyl carbonochloridate (0.74 g, 3.67 mmol) were added and the mixture was stirred at rt for a further 3 d. The reaction mixture was concentrated onto flash silica (15 mL) and the resulting powder was purified by column chromatography (normal phase, [Biotage SNAP cartridge KP-sil 100 g, 40-63 μm, 60 Å, 40 mL per min, gradient 0% to 5% Solvent A in DCM over 10 CV, where Solvent A is 10% of {7 M NH₃ in MeOH} in MeOH]) to give an oil which was further purified by column chromatography (normal phase, [Biotage SNAP cartridge KP-sil 100 g, 40-63 μm, 60 Å, 40 mL per min, isochratic 5% EtOAc in DCM over 5 CV then isochratic 5% Solvent A in DCM over 5 CV, where Solvent A is 10% of {7 M NH₃ in MeOH} in MeOH]) to give an oil (6.85 g). The oil was dissolved in DCM, washed with H₂O (×2), dried by passing through a phase separator cartridge and concentrated to give 4-nitrophenyl 2-{4-[acetyl(ethyl)amino]piperidin-1-yl}-6-azaspiro[3.4]octane-6-carboxylate as a foam (2.41 g, 73%).

LCMS (Method C): m/z 445 (M+H)⁺ (ES⁺), at 1.32 min, UV active.

Intermediate 116, (1,1-²H₂)-ethanol (0.42 mL, 7.19 mmol) was dissolved in THF (18 mL) under an atmosphere of nitrogen and treated with 60% sodium hydride suspension in mineral oil (0.29 g, 7.25 mmol). The mixture was stirred at rt for 1 h, then 4-nitrophenyl 2-{4-[acetyl(ethyl)amino]piperidin-1-yl}-6-azaspiro[3.4]octane-6-carboxylate (0.800 g, 1.80 mmol) was added and the resulting mixture was stirred at rt for 4 d. The reaction mixture was concentrated to remove THF then the residue was diluted with H₂O and extracted with EtOAc (×2). The combined organic phases were passed through a phase separator cartidge and concentrated onto flash silica (10 mL). The resulting powder was purified by column chromatography (normal phase, [Biotage SNAP cartridge KP-sil 50 g, 40-63 μm, 60 Å, 40 mL per min, isochratic 20% EtOAc in DCM over 5 CV, gradient 20% EtOAc in DCM to 10% Solvent A in DCM over 1 CV, isochratic 10% Solvent A in DCM over 10 CV, where Solvent A is 10% of {7 M NH₃ in MeOH} in MeOH]) to give an inseparable mixture of diastereoisomers (0.359 g, 56%). This mixture was purified by preparative reversed phase HPLC (Phenomenex Gemini-NX 5 μm C18 110A Axia column, 100×30 mm, eluting with 20 to 50% MeCN/Solvent B over 14.4 min at 30 mL/min [where solvent B is 0.2% of (28% NH₃/H₂O) in H₂O] and collecting fractions by monitoring at 205 nm) to give Example 2-38 Isomer 1, (1,1-²H2)-ethyl 2-{4-[acetyl(ethyl)amino]piperidin-1-yl}-6-azaspiro[3.4]octane-6-carboxylate (140 mg, 22%) as a gum and Example 2-38 Isomer 2, (1,1-²H2)-ethyl 2-{4-[acetyl (ethyl)amino]piperidin-1-yl}-6-azaspiro[3.4]octane-6-carboxylate (129 mg, 20%) as a gum.

The data for Example 2-38 Isomer 2 are in Table 3.

Route e

Typical Procedure for the Preparation of Piperidines where a Mixture of More than Two Isomers is Separated by Using Reversed Phase Chromatography Followed by Chiral Chromatography as Exemplified by the Preparation of Example 2-63, ethyl 2-(4-{1-[acetyl(ethyl)amino]propyl}piperidin-1-yl)-6-azaspiro[3.4]octane-6-carboxylate

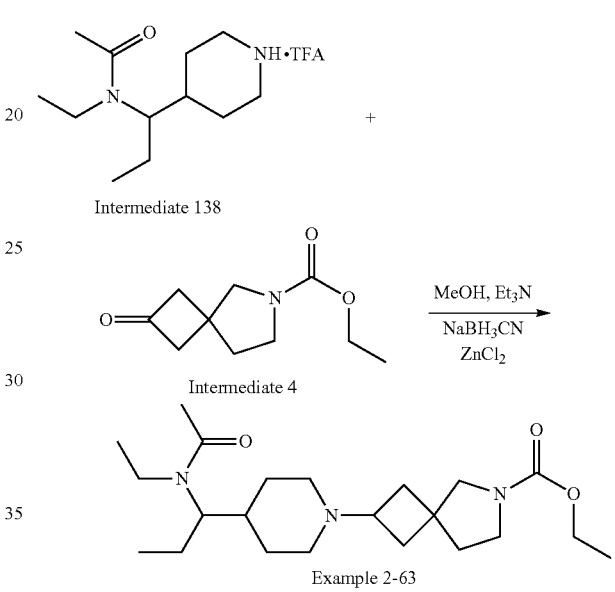

Intermediate 138, N-ethyl-N-[1-(piperidin-4-yl)propyl] acetamide trifluoroacetate (250 mg, 1.18 mmol), Intermediate 4, ethyl 2-oxo-6-azaspiro[3.4]octane-6-carboxylate (232 mg, 1.18 mmol), Et₃N (0.821 mL, 5.89 mmol), ZnCl₂ (0.3 mL) and MeOH (5 mL) were charged into a vial. The resulting mixture was heated at 60° C. for 4 h then cooled to 0° C. NaCNBH₃ (222 mg, 3.53 mmol) was added at 0° C. and the mixture was allowed to warm to room temperature and stirred for 16 h. The mixture was concentrated in vacuo and the residue was partitioned between H₂O (50 mL) and EtOAc (50 mL). The aqueous layer was further extracted with EtOAc (2×50 mL) and the combined organic layers were dried (Na₂SO₄) and the solvent was removed in vacuo to give the crude product, which was purified by preparative HPLC [reverse phase HPLC (X-BRIDGE, 250×19 mm, 5 μm, 15 mL per min, gradient 48% (over 60 min), 100% (over 2 min) then 48% (over 3 min), (A) 10 mM ammonium bicarbonate in water+0.1% NH₃ in water, (B) 50:50 (MeCN: MeOH)] to give two isomers—isomer 1 and isomer 2. The two isomers were taken in turn and further purified by chiral preparative HPLC [CHIRALCEL OX-H 250×4.6 mm, 5 μm {0.3% DEA in IPA:MeOH (50:50)} to give Example 2-63 Isomer 1a, ethyl 2-{4-[(2-hydroxyethyl)(phenyl)amino]piperidin-1-yl}-6-azaspiro[3.4]octane-6-carboxylate (13 mg, 3%) as a gum, Example 2-63 Isomer 1b, ethyl 2-{4-[(2-hydroxyethyl)(phenyl)amino]piperidin-1-yl}-6-azaspiro[3.4]octane-6-carboxylate (10 mg, 2%) as a gum, Example 2-63 Isomer 2a, ethyl 2-{4-[(2-hydroxyethyl)(phenyl)

amino]piperidin-1-yl}-6-azaspiro[3.4]octane-6-carboxylate (11 mg, 2%) as a gum and Example 2-63 Isomer 2b, ethyl 2-{4-[(2-hydroxyethyl)(phenyl)amino]piperidin-1-yl}-6-azaspiro[3.4]octane-6-carboxylate (10 mg, 2%) as a gum.

The data for Example 2-63 Isomer 2b are in Table 3.

Route f

Typical Procedure for the Preparation of Piperidines where a Mixture of More than Two Isomers is Separated by Using Reversed Phase Chromatography Followed by Chiral Chromatography as Exemplified by the Preparation of Example 2-65, ethyl 2-{4-[1-(1H-pyrazol-1-yl)ethyl]piperidin-1-yl}-6-azaspiro[3.4]octane-6-carboxylate

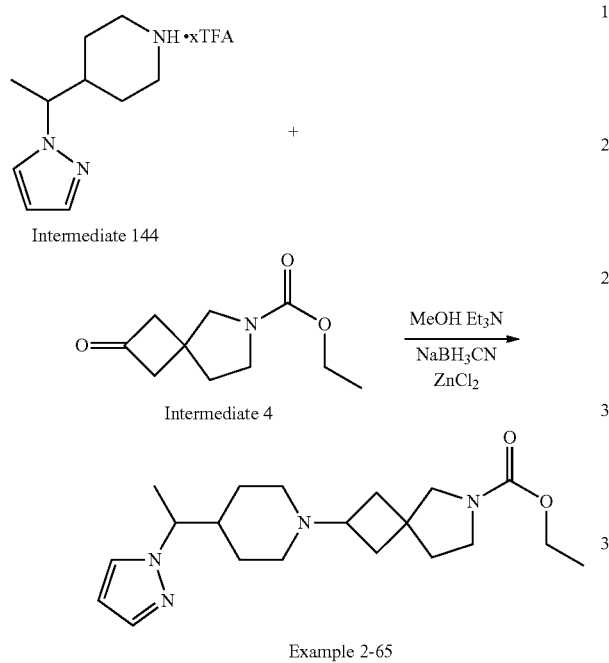

Intermediate 144, 4-[1-(1H-pyrazol-1-yl)ethyl]piperidine trifluoroacetate salt (430 mg, 2.40 mmol) and Et₃N (1.6 mL, 12.0 mmol) were dissolved in methanol (10 mL). Intermediate 4, ethyl 2-oxo-6-azaspiro[3.4]octane-6-carboxylate (473 mg, 2.40 mmol) and ZnCl₂ (0.12 mL, 0.12 mmol) were added and the reaction mixture was stirred at 70° C. for 5 h. The reaction mixture was cooled to 0° C. and NaCNBH₃ (452 mg, 7.21 mmol) was added and the reaction mixture was stirred at room temperature for 16 h. The reaction mixture was concentrated in vacuo, diluted with water (30 mL) and extracted with ethyl acetate (2×10 mL). The combined organic layers were washed with brine, dried over Na₂SO₄ and concentrated in vacuo. The crude product was purified by preparative HPLC [X-BRIDGE C18 (250×19 mm) 5 µm, 12 mL per min, gradient 30% to 100% (over 120 min) then 100% (5 min) [5 mM ammonium bicarbonate in water/MeCN:MeOH (50:50)] to give two isomers—isomer 1 and isomer 2.

Isomer 1 was further purified by Chiral SFC [Chiral CEL OX-H (250×4.6 mm) 5 µm, co-solvent: 15% of 0.3% DEA in IPA:MeOH (50:50) to give Example 2-65 Isomer 1a, ethyl 2-{4-[1-(1H-pyrazol-1-yl)ethyl]piperidin-1-yl}-6-azaspiro [3.4]octane-6-carboxylate (17 mg, 28%) and Example 2-65 Isomer 1b, ethyl 2-{4-[1-(1H-pyrazol-1-yl)ethyl]piperidin-1-yl}-6-azaspiro[3.4]octane-6-carboxylate (25 mg, 42%).

The data for Example 2-65 Isomer 1a are in Table 3.

Isomer 2 was further purified by Chiral SFC [Chiral PAK ADH (250×4.6 mm) 5 µm, co-solvent: 35% of 0.3% DEA in MeOH to give Example 2-65 Isomer 2a, ethyl 2-{4-[1-(1H-pyrazol-1-yl)ethyl]piperidin-1-yl}-6-azaspiro[3.4]octane-6-carboxylate (19 mg, 32%) and Example 2-65 Isomer 2b, ethyl 2-{4-[1-(1H-pyrazol-1-yl)ethyl]piperidin-1-yl}-6-azaspiro[3.4]octane-6-carboxylate (21 mg, 35%).

The data for Example 2-65 Isomer 2a are in Table 3.

Route g

Typical Procedure for the Preparation of Piperidines Containing the 2-azaspiro[3.4]octane Ring System where a Mixture of Two Enantiomers is Separated by Using by Using Reversed Phase Chromatography Followed by Chiral Chromatography as Exemplified by the Preparation of Example 3-2, methyl 6-{4-[acetyl(ethyl)amino]piperidin-1-yl}-2-azaspiro[3.4]octane-2-carboxylate

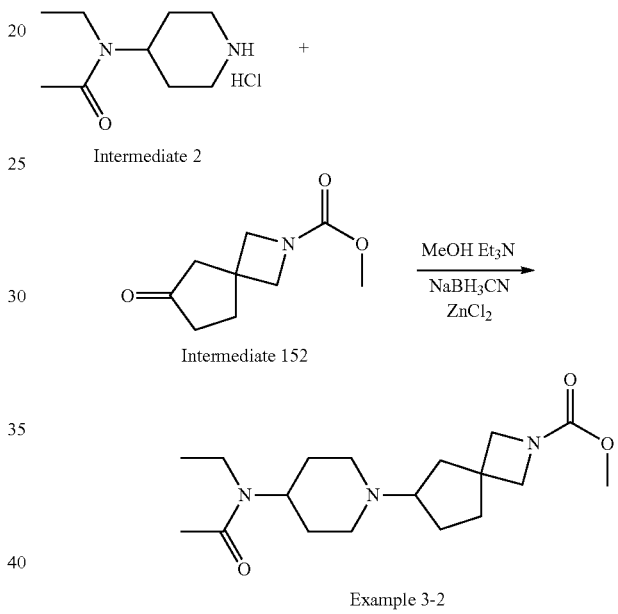

Intermediate 2, N-ethyl-N-(piperidin-4-yl)acetamide hydrochloride (150 mg, 0.818 mmol), Intermediate 152, methyl 6-oxo-2-azaspiro[3.4]octane-2-carboxylate (139 mg, 0.818 mmol), triethylamine (0.342 mL, 2.45 mmol) and ZnCl₂ (1.0 M solution in diethyl ether, 0.2 mL, 0.2 mmol) were dissolved in MeOH (100 mL) and the mixture was stirred at 60° C. for 8 h. The mixture was then cooled down to 0-5° C. and NaBH₃CN (154 mg, 2.45 mmol) was added portionwise. The resulting reaction mixture was stirred at 25° C. for 17 h, then the solvents were removed in vacuo. The residue was partitioned between H₂O (100 mL) and EtOAc (100 mL) and the aqueous layer was further extracted with EtOAc (2×50 mL). The combined organic layers were dried (Na₂SO₄) and the solvent was removed in vacuo. The residue was purified by prep. HPLC [reverse phase (PHENYL HEXYL, 250×19 mm, 5 µm, 14 mL per min, gradient 35% (over 9 min), 100% (over 2 min), then 35% (over 2 min), A: 0.1% ammonia in water, B: 100% MeCN] to give methyl 6-{4-[acetyl(ethyl)amino]piperidin-1-yl}-2-azaspiro[3.4]octane-2-carboxylate (65 mg, 22%) as a gum. This was further purified by chiral prep. HPLC (CHIRALPAK AD-H 250×4.6 mm, 5 µm, co-solvent: 0.3% diethylamine in MeOH) to give Example 3-2 Isomer 1, methyl 6-{4-[acetyl(ethyl)amino]piperidin-1-yl}-2-azaspiro

[3.4]octane-2-carboxylate (27 mg, 9%) as a gum and Example 3-2 Isomer 2, methyl 6-{4-[acetyl(ethyl)amino]piperidin-1-yl}-2-azaspiro[3.4]octane-2-carboxylate (31 mg, 11%) as a gum.

The data for Example 3-2 Isomer 2 are in Table 3.

Table 2

Characterising Data and Commercial Sources for Starting Materials and Intermediates

TABLE 2

| Intermediate | Route | Name | Data |
|---|---|---|---|
| 1 | | tert-butyl 4-oxopiperidine-1-carboxylate | Comercially available, CAS: 79099-07-3 |
| 2 | Route 2 and intermediates 1 and 44 | N-ethyl-N-(piperidin-4-yl)acetamide hydrochloride | (LC/MS Method I): m/z 171 [M + H]$^+$ (ES$^+$), at 2.21 min, UV active. |
| 3 | | tert-butyl 2-oxo-6-azaspiro[3.4]octane-6-carboxylate | Commercially available, CAS: 203661-71-6 |
| 4 | Route 1 and intermediates 3 and 5 | ethyl 2-oxo-6-azaspiro[3.4]octane-6-carboxylate | $^1$H NMR (400 MHz, CDCl$_3$) δ: 1.27 (t, J = 7.0 Hz, 3 H), 2.08 (t, J = 6.2 Hz, 2 H), 2.94-3.17 (m, 4 H), 3.49-3.59 (m, 4 H), 4.15 (q, J = 7.0 Hz, 2 H) |
| 5 | | ethyl carbonochloridate | Commercially available, CAS: 541-41-3 |
| 6 | | benzyl 4-oxopiperidine-1-carboxylate | Commercially available, CAS: 19099-93-5 |
| 7 | | cyclopropanamine | Commercially available, CAS: 765-30-0 |
| 8 | Route 3 and intermediates 6 and 7 | N-cyclopropyl-N-(piperidin-4-yl)acetamide | (LC/MS Method F) m/z 183 (M + H)$^+$ (ES+) at 0.26 min, UV active |
| 9 | | cyclobutanamine | Commercially available, CAS: 2516-34-9 |
| 10 | Route 2 and intermediates 1 and 9 | N-cyclobutyl-N-(piperidin-4-yl)acetamide hydrochloride | (LC/MS Method K) m/z 197 (M + H)$^+$ (ES$^+$) at 3.58 min, UV active |
| 11 | Route 4 and intermediates 1 and 7 | tert-butyl 4-(cyclopropylamino)piperidine-1-carboxylate | (LC/MS Method I) m/z 241 (M + H)$^+$ (ES+) at 4.16 min, UV active. |
| 12 | | methyl bromoacetate | Commercially available, CAS: 96-32-2 |
| 13 | Route 4 and Intermediates 11 and 12 | methyl [cyclopropyl(piperidin-4-yl)amino]acetate hydrochloride | (LC/MS Method K) m/z 213 (M + H)$^+$ (ES$^+$) at 3.17 min, UV active |
| 14 | | 3-(chloromethyl)-1,2-oxazole | Commercially available, CAS: 57684-71-6 |
| 15 | Route 5 and intermediates 11 and 14 | N-cyclopropyl-N-(1,2-oxazol-3-ylmethyl)piperidin-4-amine hydrochloride | (LC/MS Method K) m/z 222 (M + H)$^+$ (ES+) at 3.24 min, UV active |
| 16 | | tert-butyl 6-oxo-2-azaspiro[3.3]heptane-2-carboxylate | Commercially available, CAS: 1181816-12-5 |
| 17 | Route 1 and Intermediates 5 and 16 | ethyl 6-oxo-2-azaspiro[3.3]heptane-2-carboxylate | $^1$H NMR (400 MHz, CDCl$_3$) δ: 1.26 (t, J = 6.6 Hz, 3 H), 3.31 (s, 4 H), 4.06-4.24 (m, 6 H) |
| 18 | Route 6 and intermediates 1, 19 and 20 | N-ethyl-N-(2,2,2-trifluoroethyl)piperidin-4-amine hydrochloride | (LC/MS Method F) m/z 211 (M + H)$^+$ (ES+) at 1.41 min, UV active |
| 19 | | 2,2,2-trifluoroethanamine | Commercially available, CAS: 753-90-2 |
| 20 | | acetaldehyde | Commercially available, CAS: 75-07-0 |
| 21 | Route 7 and intermediates 11 and 22 | N-cyclopropyl-N-(2-methoxyethyl)piperidin-4-amine hydrochloride | (LC/MS Method K) m/z 199 (M + H)$^+$ (ES+) at 3.64 min, UV active |
| 22 | | 1-bromo-2-methoxyethane | Commercially available, CAS: 6482-24-2 |
| 23 | Route 2 and intermediates 1 and 9 | N-cyclobutyl-N-(piperidin-4-yl)acetamide hydrochloride | (LC/MS Method K) m/z 197 (M + H)$^+$ (ES+) at 3.58 min, UV active |
| 24 | Route 2 and intermediates 1 and 25 | N-methyl-N-(piperidin-4-yl)acetamide hydrochloride | (LC/MS Method K) m/z 157 (M + H)$^+$ (ES+) at 3.21 min, UV active |
| 25 | | methylamine | Commercially available, CAS: 74-89-5 |
| 26 | Route 2 and intermediates 1 and 27 | N-(piperidin-4-yl)-N-(propan-2-yl)acetamide hydrochloride | (LC/MS Method K) m/z 185 (M + H)$^+$ (ES+) at 3.31 min, UV active |
| 27 | | isopropylamine | Commercially available, CAS: 75-31-0 |

TABLE 2-continued

| Intermediate | Route | Name | Data |
|---|---|---|---|
| 28 | Route 2 and intermediates 1, 7 and 29 | N-cyclopropyl-N-(piperidin-4-yl)propanamide hydrochloride | (LC/MS Method K) m/z 197 (M + H)$^+$ (ES+) at 3.21 min, UV active |
| 29 | | propanoyl chloride | Commercially available, CAS: 79-03-8 |
| 30 | Route 1 and Intermediates 5 and 31 | ethyl 6-oxo-2-azaspiro[3.4]octane-2-carboxylate | $^1$H NMR (400 MHz, MeOD-d$_4$) δ: 1.24 (q, J = 7.0 Hz, 3 H), 2.16-2.32 (m, 4 H), 2.47 (s, 2 H), 3.85-3.97 (m, 4 H), 4.08 (q, J = 7.0 Hz, 2 H) |
| 31 | | tert-butyl 6-oxo-2-azaspiro[3.4]octane-2-carboxylate | Commercially available, CAS: 1363382-39-1 |
| 32 | Route 2 and intermediates 1, 7 and 33 | N-cyclopropyl-2,2,2-trifluoro-N-(piperidin-4-yl)acetamide hydrochloride | (LC/MS Method K) m/z 237 (M + H)$^+$ (ES+) at 3.66 min, UV active |
| 33 | | trifluoroacetic anhydride | Commercially available, CAS: 407-25-0 |
| 34 | | tert-butyl 4-formylpiperidine-1-carboxylate | Commercially available, CAS: 137076-22-3 |
| 35 | Route 8 and Intermediates 7 and 34 | N-cyclopropyl-N-(piperidin-4-ylmethyl)acetamide hydrochloride | (LC/MS Method C): m/z 197 (M + H)$^+$ (ES$^+$), at 0.87 min, UV active |
| 36 | Route 9 and intermediates 7, 29 and 34 | N-cyclopropyl-N-(piperidin-4-ylmethyl)propanamide hydrochloride | (LC/MS Method C): m/z 211 (M + H)$^+$ (ES$^+$), at 1.06 min, UV active. |
| 37 | | tert-butyl 4-acetylpiperidine-1-carboxylate | Commercially available, CAS: 206989-61-9 |
| 38 | Route 8 and intermediates 7 and 37 | N-cyclopropyl-N-[1-(piperidin-4-yl)ethyl]acetamide hydrochloride | (LC/MS Method C): m/z 211 (M + H)$^+$ (ES$^+$), at 1.07 min, UV active |
| 39 | Route 9 and intermediates 7, 29 and 37 | N-cyclopropyl-N-[1-(piperidin-4-yl)ethyl]propanamide hydrochloride | (LC/MS Method C): m/z 225 (M + H)$^+$ (ES$^+$), at 1.34 min, UV active. |
| 40 | | methyl carbonochloridate | Commercially available, CAS: 79-22-1 |
| 41 | Route 1 and intermediates 3 and 40 | methyl 2-oxo-6-azaspiro[3.4]octane-6-carboxylate | $^1$H NMR: (400 MHz, MeOD-d$_4$) δ: 2.06-2.15 (m, 2 H), 2.94-3.04 (m, 2 H), 3.05-3.17 (m, 2 H), 3.47 (td, J = 6.8, 2.5 Hz, 2 H), 3.54 (d, J = 2.5 Hz, 2 H), 3.69 (s, 3 H) |
| 42 | Route 10 and intermediate 52 | N-ethyl-N-(piperidin-4-yl)formamide | (LC/MS Method K): m/z 157 (M + H)$^+$ (ES$^+$), at 2.31 min, UV active. |
| 43 | Route 2 and intermediates 1 and 44 | tert-butyl 4-(ethylamino)piperidine-1-carboxylate | (LC/MS Method F): m/z 229 [M + H]$^+$ (ES$^+$), at 1.52 min, UV active. |
| 44 | | ethanamine | Commercially available, CAS: 75-04-7 |
| 45 | | propan-1-amine | Commercially available, CAS: 107-10-8 |
| 46 | Route 11 and intermediates 1 and 45 | N-(piperidin-4-yl)-N-propylacetamide trifluoroacetate | (LC/MS Method K): m/z 185 (M + H)$^+$ (ES$^+$), at 3.13 min, UV active. |
| 47 | Route 11 and intermediates 1 and 48 | N-(2-methylpropyl)-N-(piperidin-4-yl)acetamide trifluoroacetate | (LC/MS Method I): m/z 199 (M + H)$^+$ (ES$^+$), at 2.92 min, UV active. |
| 48 | | 2-methylpropan-1-amine | Commercially available, CAS: 78-81-9 |
| 49 | | 1-cyclopropylmethanamine | Commercially available, CAS: 2516-47-4 |
| 50 | Route 11 and intermediates 1 and 49 | N-(cyclopropylmethyl)-N-(piperidin-4-yl)acetamide trifluoroacetate | (LC/MS Method H): m/z 197 (M + H)$^+$ (ES$^+$), at 2.68 min, UV active. |
| 51 | | 1-(1-methylcyclobutyl)methanamine | Commercially available, CAS: 1245647-53-3 |
| 52 | | benzyl 4-(ethylamino)piperidine-1-carboxylate | Commercially available, CAS: 159874-38-1 |
| 53 | Route 11 and intermediates 1 and 44 | N-ethyl-N-(piperidin-4-yl)acetamide trifluoroacetate | (LC/MS Method K): m/z 171 (M + H)$^+$ (ES$^+$), at 2.24 min, UV active. |
| 54 | Route 11 and intermediates 1 and 51 | N-[(1-methylcyclobutyl)methyl]-N-(piperidin-4-yl)acetamide trifluoroacetate | (LC/MS Method K): m/z 225 (M + H)$^+$ (ES$^+$), at 1.52 min, UV active. |
| 55 | | 1-methylcyclobutanamine hydrochloride | Commercially available, CAS: 174886-05-6 |

TABLE 2-continued

| Intermediate | Route | Name | Data |
|---|---|---|---|
| 56 | Route 11 and intermediates 1 and 55 | N-(1-methylcyclobutyl)-N-(piperidin-4-yl)acetamide trifluoroacetate | (LC/MS Method I): m/z 211 (M + H)$^+$ (ES$^+$), at 3.50 min, UV active. |
| 57 | | 1,4-dioxa-8-azaspiro[4.5]decane | Commercially available, CAS: 177-11-7 |
| 58 | | 1-(3-methyloxetan-3-yl)methanamine | Commercially available, CAS: 153209-97-3 |
| 59 | | 2,2-difluoroethanamine | Commercially available, CAS: 430-67-1 |
| 60 | Route 2 and intermediates 1 and 59 | N-(2,2-difluoroethyl)-N-(piperidin-4-yl)acetamide hydrochloride | (LC/MS Method F): m/z 207 (M + H)$^+$ (ES$^+$), at 0.39 min, UV active. |
| 61 | | 2,2,2-trifluoroethanamine | Commercially available, CAS: 753-90-2 |
| 62 | Route 2 and intermediates 1 and 61 | N-(piperidin-4-yl)-N-(2,2,2-trifluoroethyl)acetamide hydrochloride | (LC/MS Method K): m/z 225 (M + H)$^+$ (ES$^+$), at 3.21 min, UV active. |
| 63 | | 2-fluoro-2-methylpropan-1-amine | Commercially available, CAS: 879121-42-3 |
| 64 | Route 2 and intermediates 1 and 63 | N-(2-fluoro-2-methylpropyl)-N-(piperidin-4-yl)acetamide hydrochloride | (LC/MS Method I): m/z 217 (M + H)$^+$ (ES$^+$), at 2.96 min, UV active. |
| 65 | | 2,2-difluoropropan-1-amine | Commercially available, CAS: 421-00-1 |
| 66 | Route 11 and intermediates 1 and 65 | N-(2,2-difluoropropyl)-N-(piperidin-4-yl)acetamide trifluoroacetate | (LC/MS Method I): m/z 221 (M + H)$^+$ (ES$^+$), at 2.82 min, UV active. |
| 67 | | 3,3-difluorocyclobutanamine | Commercially available, CAS: 791061-00-2 |
| 68 | Route 11 and intermediates 1 and 67 | N-(3,3-difluorocyclobutyl)-N-(piperidin-4-yl)acetamide trifluoroacetate | (LC/MS Method I): m/z 233 (M + H)$^+$ (ES$^+$), at 3.02 min, UV active. |
| 69 | | 2-methoxy-2-methylpropan-1-amine | Commercially available, CAS: 89282-70-2 |
| 70 | Route 2 and intermediates 1 and 69 | N-(2-methoxy-2-methylpropyl)-N-(piperidin-4-yl)acetamide hydrochloride | (LC/MS Method I): m/z 229 (M + H)$^+$ (ES$^+$), at 2.97 min, UV active. |
| 71 | Route 11 and intermediates 1 and 72 | N-[(1-methoxycyclobutyl)methyl]-N-(piperidin-4-yl)acetamide trifluoroacetate | (LC/MS Method F): m/z 241 (M + H)$^+$ (ES$^+$), at 1.29 min, UV active. |
| 72 | | 1-(1-methoxycyclobutyl)methanamine | Commercially available, CAS: 1443980-50-4 |
| 73 | | 1-(aminomethyl)cyclobutanol | Commercially available, CAS: 180205-28-1 |
| 74 | Route 11 and intermediates 1 and 73 | N-[(1-hydroxycyclobutyl)methyl]-N-(piperidin-4-yl)acetamide trifluoroacetate | (LC/MS Method J): m/z 227 (M + H)$^+$ (ES$^+$), at 2.97 min, UV active. |
| 75 | | O-methylhydroxylamine | Commercially available, CAS: 67-62-9 |
| 76 | Route 12 and intermediates 1 and 75 | N-methoxy-N-(piperidin-4-yl)acetamide trifluoroacetate | (LC/MS Method F): m/z 173 (M + H)$^+$ (ES$^+$), at 0.25 min, UV active. |
| 77 | | aniline | Commercially available, CAS: 62-53-3 |
| 78 | Route 2 and intermediates 1 and 77 | N-phenyl-N-(piperidin-4-yl)acetamide hydrochloride | (LC/MS Method I): m/z 219 (M + H)$^+$ (ES$^+$), at 3.18 min, UV active. |
| 79 | | 2-Aminopyridine | Commercially available, CAS: 504-29-0 |
| 80 | Route 2 and intermediates 1 and 79 | N-(piperidin-4-yl)-N-(pyridin-2-yl) acetamide hydrochloride | (LC/MS Method I): m/z 220 (M + H)$^+$ (ES$^+$), at 2.41 min, UV active. |
| 81 | | benzylamine | Commercially available, CAS: 100-46-9 |
| 82 | Route 2 and intermediates 1 and 81 | N-benzyl-N-(piperidin-4-yl)acetamide hydrochloride | (LC/MS Method I): m/z 233 (M + H)$^+$ (ES$^+$), at 3.17 min, UV active. |
| 83 | | [(tert-butoxycarbonyl)amino]acetic acid | Commercially available, CAS: 4530-20-5 |
| 84 | | N-methoxymethanamine hydrochloride | Commercially available, CAS: 6638-79-5 |
| 85 | | N-(3-dimethylaminopropyl)-N'-ethylcarbodiimide hydrochloride | Commercially available, CAS: 25952-53-8 |

TABLE 2-continued

| Intermediate | Route | Name | Data |
|---|---|---|---|
| 86 | | 1-hydroxybenzotriazole hydrate | Commercially available, CAS: 123333-53-9 |
| 87 | | lithium aluminium hydride | Commercially available, CAS: 16853-85-3 |
| 88 | | p-toluenesulfonylmethyl isocyanide | Commercially available, CAS: 36635-61-7 |
| 89 | Route 13 and intermediates 83, 84, 85, 86, 87 and 88 | 1-(1,3-oxazol-5-yl)methanamine hydrochloride | $^1$H NMR (400 MHz, DMSO-$d_6$) δ: 4.11-4.17 (m, 2 H), 7.28 (s, 1 H), 8.47 (t, J = 12.0 Hz, 1 H), 8.77 (s, 3 H), 10.23 (s, 1 H). |
| 90 | Route 2 and intermediates 1 and 89 | N-(1,3-oxazol-5-ylmethyl)-N-(piperidin-4-yl)acetamide hydrochloride | (LC/MS Method I): m/z 224 (M + H)$^+$ (ES$^+$), at 2.41 min, UV active. |
| 91 | | tert-butyl 4-aminopiperidine-1-carboxylate | Commercially available, CAS: 87120-72-7 |
| 92 | | 1,3-oxazole-2-carbaldehyde | Commercially available, CAS: 65373-52-6 |
| 93 | Route 11 and intermediates 91 and 92 | N-(1,3-oxazol-2-ylmethyl)-N-(piperidin-4-yl)acetamide trifluoroacetate | (LC/MS Method F): m/z 224 (M + H)$^+$ (ES$^+$), at 0.31 min, UV active. |
| 94 | Route 2 and intermediates 1 and 40 | methyl ethyl(piperidin-4-yl)carbamate hydrochloride | (LC/MS Method F): m/z 187 (M + H)$^+$ (ES$^+$), at 0.90 min, UV active |
| 95 | Route 2 and intermediates 1 and 5 | ethyl ethyl(piperidin-4-yl)carbamate hydrochloride | (LC/MS Method F): m/z 201 (M + H)$^+$ (ES$^+$), at 1.52 min, UV active |
| 96 | Route 11 and intermediates 1, 27 and 40 | Methyl isopropyl(piperidin-4-yl)carbamate trifluoroacetate | (LC/MS Method I): m/z 201 (M + H)$^+$ (ES$^+$), at 2.97 min, UV active |
| 97 | Route 6 and intermediates 1 and 19 | tert-butyl 4-[(2,2,2-trifluoroethyl)amino]piperidine-1-carboxylate | (LC/MS Method I): m/z 227 (M + H − 56)$^+$ (ES$^+$), at 4.62 min, UV active |
| 98 | Route 14 and intermediates 97 and 40 | methyl piperidin-4-yl(2,2,2-trifluoroethyl)carbamate hydrochloride | (LC/MS Method I): m/z 241 (M + H)$^+$ (ES$^+$), at 3.34 min, UV active |
| 99 | Route 15 and intermediates 97 and 22 | 2-methoxyethyl piperidin-4-yl(2,2,2-trifluoroethyl)carbamate hydrochloride | (LC/MS Method I): m/z 285 (M + H)$^+$ (ES$^+$), at 3.38 min, UV active |
| 100 | | dimethylcarbamic chloride | Commercially available, CAS: 79-44-7 |
| 101 | Route 2 and intermediates 1 and 100 | 1-ethyl-3,3-dimethyl-1-piperidin-4-ylurea hydrochloride | (LC/MS Method F): m/z 200 (M + H)$^+$ (ES$^+$), at 0.92 min, UV active |
| 102 | | 2-fluoroethanamine hydrochloride | Commercially available, CAS: 460-08-2 |
| 103 | Route 6 and intermediates 1, 102 and 20 | N-ethyl-N-(2-fluoroethyl)piperidin-4-amine hydrochloride | (LC/MS Method F) m/z 175 (M + H)$^+$ (ES+) at 0.26 min, UV active |
| 104 | | Difluoroethan-1-amine | Commercially available, CAS: 430-67-1 |
| 105 | Route 6 and intermediates 1, 104 and 20 | N-(2,2-difluoroethyl)-N-ethylpiperidin-4-amine hydrochloride | (LC/MS Method I) m/z 193 (M + H)$^+$ (ES+) at 3.60 min, UV active |
| 106 | | oxetan-3-amine | Commercially available, CAS: 21635-88-1 |
| 107 | | N-methyl-2-pyrrolidinone | Commercially available, CAS: 872-50-4 |
| 108 | | 2,2,2-trifluoroethyl trifluoromethanesulfonate | Commercially available, CAS: 6226-25-1 |
| 109 | Route 16 and intermediates 11, 107 and 108 | N-cyclopropyl-N-(2,2,2-trifluoroethyl)piperidin-4-amine hydrochloride | (LC/MS Method K) m/z 223 (M + H)$^+$ (ES+) at 5.08 min, UV active |
| 110 | | 2-bromoethanol | Commercially available, CAS: 540-51-2 |
| 111 | Route 17 and intermediates 11 and 110 | 2-[cyclopropyl(piperidin-4-yl)amino]ethanol trifluoroacetate | (LC/MS Method F) m/z 185 (M + H)$^+$ (ES+) at 0.26 min, UV active |
| 112 | Route 18 and intermediates 1 and 9 | tert-butyl 4-(cyclobutylamino)piperidine-1-carboxylate | (LC/MS Method I) m/z 255 (M + H)$^+$ (ES+) at 4.38 min, UV active |
| 113 | Route 17 and intermediates 112 and 110 | 2-[cyclobutyl(piperidin-4-yl)amino]ethanol trifluoroacetate | (LC/MS Method I) m/z 199 (M + H)$^+$ (ES+) at 3.20 min, UV active |
| 114 | | N-ethyl-N-(piperidin-4-yl)acetamide | Commercially available, CAS: 139062-99-0 |
| 115 | | 4-nitrophenyl carbonochloridate | Commercially available, CAS: 7693-46-1 |

TABLE 2-continued

| Intermediate | Route | Name | Data |
|---|---|---|---|
| 116 | | (1,1-$^2$H$_2$)-ethanol | Commercially available, CAS: 1859-09-2 |
| 117 | Route 7 and Intermediates 97 and 110 | 2-[piperidin-4-yl(2,2,2-trifluoroethyl)amino]ethanol hydrochloride | (LC/MS Method I): m/z 227 (M + H)$^+$ (ES$^+$), at 4.40 min, UV active. |
| 118 | | 2-methoxyethylamine | Commercially available, CAS: 109-85-3 |
| 119 | Route 19 and Intermediates 1, 118 and 108 | N-(2-methoxyethyl)-N-(2,2,2-trifluoroethyl)piperidin-4-amine trifluoroacetate | (LC/MS Method I): m/z 241 (M + H)$^+$ (ES$^+$), at 4.05 min, UV active. |
| 120 | Route 20 and Intermediates 1, 106, 121 and 20 | N-ethyl-N-(oxetan-3-yl)piperidin-4-amine trifluoroacetate | (LC/MS Method I): m/z 185 (M + H)$^+$ (ES$^+$), at 2.42 min, UV active. |
| 121 | Route 20 and Intermediates 1 and 106 | tert-butyl 4-(oxetan-3-ylamino)piperidine-1-carboxylate | (LC/MS Method I): m/z 257 (M + H)$^+$ (ES$^+$), at 2.92 min, UV active. |
| 122 | Route 19 and Intermediates 121 and 108 | N-(oxetan-3-yl)-N-(2,2,2-trifluoroethyl)piperidin-4-amine trifluoroacetate | (LC/MS Method I): m/z 239 (M + H)$^+$ (ES$^+$), at 3.18 min, UV active. |
| 123 | | 3-aminopropanenitrile | Commercially available, CAS: 151-18-8 |
| 124 | Route 20 and Intermediates 1, 123 and 20 | 3-[ethyl(piperidin-4-yl)amino]propanenitrile trifluoroacetate | (LC/MS Method I): m/z 182 (M + H)$^+$ (ES$^+$), at 3.16 min, UV active. |
| 125 | | 2-(methylsulfonyl)ethanamine | Commercially available, CAS: 49773-20-8 |
| 126 | Route 6 and Intermediates 1, 125 and 20 | N-ethyl-N-[2-(methylsulfonyl)ethyl]piperidin-4-amine hydrochloride | (LC/MS Method I): m/z 235 (M + H)$^+$ (ES$^+$), at 2.71 min, UV active. |
| 127 | | iodoethane | Commercially available, CAS: 75-03-6 |
| 128 | Route 21 and Intermediates 1, 75 and 127 | N-ethyl-N-methoxypiperidin-4-amine trifluoroacetate | (LC/MS Method F): m/z 159 (M + H)$^+$ (ES$^+$), at 2.71 min, UV active. |
| 129 | | ethyl bromoacetate | Commercially available, CAS: 105-36-2 |
| 130 | Route 22 and Intermediates 1, 77 and 129 | 2-[phenyl(piperidin-4-yl)amino]ethanol hydrochloride | (LC/MS Method F): m/z 221 (M + H)$^+$ (ES$^+$), at 1.09 min, UV active. |
| 131 | Route 18 and Intermediates 1 and 81 | tert-butyl 4-(benzylamino)piperidine-1-carboxylate | (LC/MS Method I): m/z 291 (M + H)$^+$ (ES$^+$), at 4.80 min, UV active |
| 132 | Route 16 and Intermediates 131, 107 and 11 | N-benzyl-N-(2,2,2-trifluoroethyl)piperidin-4-amine hydrochloride | (LC/MS Method K): m/z 273 (M + H)$^+$ (ES$^+$), at 5.99 min, UV active. |
| 133 | Route 20 and Intermediates 1, 89 and 20 | N-ethyl-N-(1,3-oxazol-5-ylmethyl)piperidin-4-amine trifluoroacetate | $^1$H NMR (400 MHz, DMSO-d$_6$) δ: 1.02-1.16 (m, 3 H), 1.74-2.02 (m, 2 H), 2.14-2.31 (m, 2 H), 2.89-3.03 (m, 2 H), 3.08-3.32 (m, 3 H), 3.37-3.48 (m, 2 H), 4.61 (s, 2 H), 7.52 (s, 1 H), 8.59 (s, 1 H). Exchangeable protons not observed. |
| 134 | | 2-fluoroethyl trifluoromethanesulfonate | Commercially available, CAS: 95353-04-1 |
| 135 | Route 19 and Intermediates 1, 89 and 134 | N-(2-fluoroethyl)-N-(1,3-oxazol-5-ylmethyl)piperidin-4-amine trifluoroacetate | (LC/MS Method I): m/z 228 (M + H)$^+$ (ES$^+$), at 3.19 min, UV active. |
| 136 | Route 19 and Intermediates 1, 89 and 108 | N-(1,3-oxazol-5-ylmethyl)-N-(2,2,2-trifluoroethyl)piperidin-4-amine trifluoroacetate | (LC/MS Method F): m/z 264 (M + H)$^+$ (ES$^+$), at 1.53 min, UV active. |
| 137 | | tert-butyl 4-propanoylpiperidine-1-carboxylate | Commercially available, CAS: 419571-73-6 |
| 138 | Route 23 and Intermediates 44 and 137 | N-ethyl-N-[1-(piperidin-4-yl)propyl]acetamide trifluoroacetate | (LC/MS Method I): m/z 213 (M + H)$^+$ (ES$^+$), at 3.12 min, UV active. |
| 139 | | tert-butyl 4-(2-aminopropan-2-yl)piperidine-1-carboxylate | Commercially available, CAS: 530116-33-7 |
| 140 | Route 24 and Intermediates 139 and 20 | N-ethyl-N-[2-(piperidin-4-yl)propan-2-yl]acetamide hydrochloride | (LC/MS Method F): m/z 213 (M + H)$^+$ (ES$^+$), at 1.50 min, UV active. |
| 141 | | tert-butyl 4-(1-hydroxyethyl)piperidine-1-carboxylate | Commercially available, CAS: 183170-69-6 |
| 142 | | methanesulfonyl chloride | Commercially available, CAS: 124-63-0 |

TABLE 2-continued

| Intermediate | Route | Name | Data |
| --- | --- | --- | --- |
| 143 | | 1H-pyrazole | Commercially available, CAS: 288-13-1 |
| 144 | Route 25 and Intermediates 141, 142 and 143 | 4-[1-(1H-pyrazol-1-yl)ethyl]piperidine trifluoroacetate | (LC/MS Method I): m/z 180 (M + H)$^+$ (ES$^+$), at 3.42 min, UV active. |
| 145 | | tert-butyl 4-hydroxypiperidine-1-carboxylate | Commercially available, CAS: 109384-19-2 |
| 146 | | (1-bromoethyl)benzene | Commercially available, CAS: 585-71-7 |
| 147 | Route 26 and Intermediates 145 and 146 | 4-(1-phenylethoxy)piperidine hydrochloride | (LC/MS Method I): m/z 206 (M + H)$^+$ (ES$^+$), at 4.93 min, UV active. |
| 148 | | tert-butyl 4-bromopiperidine-1-carboxylate | Commercially available, CAS: 180695-79-8 |
| 149 | | phenylmethanethiol | Commercially available, CAS: 100-53-8 |
| 150 | Route 27 and Intermediates 148 and 149 | 4-(benzylsulfanyl)piperidine hydrochloride | (LC/MS Method F): m/z 208 (M + H)$^+$ (ES$^+$), at 1.70 min, UV active. |
| 151 | | tert-butyl 6-oxo-2-azaspiro[3.4]octane-2-carboxylate | Commercially available, CAS: 1363382-39-1 |
| 152 | Route 28 and Intermediates 151 and 40 | methyl 6-oxo-2-azaspiro[3.4]octane-2-carboxylate | (LC/MS Method I): m/z 184 (M + H)$^+$ (ES$^+$), at 2.47 min, UV active. |
| 153 | Route 28 and Intermediates 151 and 5 | ethyl 6-oxo-2-azaspiro[3.4]octane-2-carboxylate | (LC/MS Method I): m/z 198 (M + H)$^+$ (ES$^+$), at 2.89 min, UV active. |

TABLE 3

| Ex. No. | Name | Intermediate | Synthetic method | ¹H NMR | LCMS Method | LCMS data |
|---|---|---|---|---|---|---|
| 1-1 | Ethyl 6-{4-[acetyl(cyclopropyl)amino]piperidin-1-yl}-2-azaspiro[3.3]heptane-2-carboxylate | 8 and 17 | a | (400 MHz, CDCl₃) δ: 0.80-0.94 (m, 4 H), 1.25 (t, J = 7.0 Hz, 3 H), 1.73-2.07 (m, 8 H), 2.22 (s, 3 H), 2.30-2.35 (m, 2 H), 2.46-2.62 (m, 2 H), 2.88-2.91 (m, 2 H), 3.88 (s, 2 H), 4.00 (s, 2 H), 4.08-4.20 (m, 3 H) | I | m/z 350 (M + H)⁺ (ES⁺) at 3.45 min, UV active |
| 1-2 | Ethyl 6-{4-[acetyl(ethyl)amino]piperidin-1-yl}-2-azaspiro[3.3]heptane-2-carboxylate | 2 and 17 | a | (400 MHz, MeOD-d₄) δ: 1.10-1.30 (m, 6 H), 1.62-1.73 (m, 1 H), 1.73-2.00 (m, 5 H), 2.02-2.11 (m, 2 H), 2.14 (d, J = 2.8 Hz, 3 H), 2.34-2.44 (m, 2 H), 2.63-2.76 (m, 1 H), 2.93-3.03 (m, 2 H), 3.28-3.42 (m, 2 H), 3.65-3.77 (m, 0.5 H), 3.86-3.94 (m, 2 H), 3.98-4.05 (m, 2 H), 4.09 (q, J = 7.3 Hz, 2 H), 4.19-4.31 (m, 0.5 H) | I | m/z 338 (M + H)⁺ (ES⁺) at 3.31 min, UV active |
| 2-1 | Isomer 2: Ethyl 2-{4-[acetyl(ethyl)amino]piperidin-1-yl}-6-azaspiro[3.4]octane-6-carboxylate | 2 and 4 | a | (400 MHz, MeOD-d₄) δ: 1.23-1.31 (m, 7 H), 1.68-1.99 (m, 10 H), 2.13-2.17 (m, 5 H), 2.79-3.07 (m, 3 H), 3.29 (m, 2 H), 3.37-3.44 (m, 4 H), 4.11 (q, J = 7.0 Hz, 2 H) | I | m/z 352 (M + H)⁺ (ES⁺) at 3.46 min, UV active |
| 2-2 | Isomer 2: Ethyl 2-{4-[acetyl(propan-2-yl)amino]piperidin-1-yl}-6-azaspiro[3.4]octane-6-carboxylate | 4 and 26 | a | (400 MHz, CDCl₃) δ: 1.14-1.42 (m, 8 H), 1.65-2.19 (m, 18 H), 2.41-3.14 (m, 3 H), 3.21-3.58 (m, 4 H), 3.85-4.18 (m, 2 H) | I | m/z 366 (M + H)⁺ (ES⁺) at 3.99 min, UV active |
| 2-3 | Isomer 1: Ethyl 2-{4-[acetyl(cyclopropyl)amino]piperidin-1-yl}-6-azaspiro[3.4]octane-6-carboxylate | 4 and 8 | a | (400 MHz, DMSO-d₆) δ: 0.81-0.87 (m, 4 H), 1.16-1.24 (m, 4 H), 1.80-1.91 (m, 4 H), 2.11 (s, 3 H), 2.16-2.41 (m, 5 H), 2.64-2.90 (m, 4 H), 3.04-3.31 (m, 5 H), 3.40-3.69 (m, 2 H), 4.02 (q, J = 7.0 Hz, 2 H) | F | m/z 364 (M + H)⁺ (ES⁺) at 1.51 min |
| 2-3 | Isomer 2: Ethyl 2-{4-[acetyl(cyclopropyl)amino]piperidin-1-yl}-6-azaspiro[3.4]octane-6-carboxylate | 4 and 8 | a | (400 MHz, DMSO-d₆) δ: 0.67-0.90 (m, 5 H), 1.16 (t, J = 7.0 Hz, 3 H), 1.51-2.05 (m, 9 H), 2.09 (s, 3 H), 2.56-2.68 (m, 2 H), 2.78-2.99 (m, 2 H), 3.11-3.30 (m, 5 H), 3.41-3.53 (m, 1 H), 3.77-3.89 (m, 1 H), 4.00 (q, J = 7.0 Hz, 2 H) | F | m/z 364 (M + H)⁺ (ES⁺) at 1.51 min |
| 2-4 | Isomer 2: Ethyl 2-{4-[cyclopropyl(trifluoroacetyl)amino]piperidin-1-yl}-6-azaspiro[3.4]octane-6-carboxylate | 4 and 32 | a | (400 MHz, MeOD-d₄) δ: 0.98 (d, J = 6.5 Hz, 4 H), 1.27 (t, J = 7.0 Hz, 3 H), 1.80-1.98 (m, 8 H), 2.11-2.27 (m, 4 H), 2.76-3.02 (m, 4 H), 3.29 (s, 2 H), 3.41 (q, J = 7.0 Hz, 2 H), 3.77-3.90 (m, 1 H), 4.11 (q, J = 7.0 Hz, 2 H) | I | m/z 418 (M + H)⁺ (ES⁺) at 4.80 min, UV active |
| 2-5 | Isomer 2: Ethyl 2-{4-[cyclopropyl(propanoyl)amino]piperidin-1-yl}-6-azaspiro[3.4]octane-6-carboxylate | 4 and 28 | a | (400 MHz, MeOD-d₄) δ: 0.80-1.00 (m, 4 H), 1.12 (t, J = 7.5 Hz, 3 H), 1.25-1.36 (m, 4 H), 1.73-1.76 (m, 2 H), 1.87-1.98 (m, 6 H), 2.07-2.18 (m, 3 H), 2.59-2.70 (m, 2 H), 2.77-2.84 (m, 1 H), 2.97-3.00 (m, 2 H), 3.29 (s, 2 H), 3.37-3.43 (m, 3 H), 3.91-4.02 (m, 1 H), 4.11 (q, J = 7.0 Hz, 2 H) | I | m/z 378 (M + H)⁺ (ES⁺) at 4.10 min, UV active |
| 2-6 | Isomer 2: Ethyl 2-{4-[acetyl(cyclobutyl)amino]piperidin-1-yl}-6-azaspiro[3.4]octane-6-carboxylate | 10 and 4 | a | (400 MHz, DMSO-d₆) δ: 1.16 (t, J = 7.0 Hz, 3 H), 1.24-1.40 (m, 1 H), 1.44-2.24 (m, 20 H), 2.31-2.47 (m, 1 H), 2.58-2.97 (m, 4 H), 3.15 (d, J = 6.5 Hz, 2 H), 3.25-3.30 (m, 2 H), 4.00 (q, J = 7.0 Hz, 2 H) | I | m/z 378 (M + H)⁺ (ES⁺) at 4.28 min, UV active |
| 2-7 | Isomer 2: Ethyl 2-[4-[ethyl(2,2,2-trifluoro- | 18 and 4 | a | (400 MHz, DMSO-d₆) δ: 0.96 (t, J = 7.0 Hz, 3 H), 1.56 (t, J = 7.0 Hz, 3 H), 1.31-1.40 (m, 2 H), 1.61-1.99 (m, 8 H), | I | m/z 392 (M + H)⁺ (ES⁺) at 5.25 min, |

TABLE 3-continued

| Ex. No. | Name | Intermediate | Synthetic method | ¹H NMR | LCMS Method | LCMS data |
|---|---|---|---|---|---|---|
| 2-8 | Isomer 2: Ethyl 2-{4-[(ethyl)amino]piperidin-1-yl}-6-azaspiro[3.4]octane-6-carboxylate | 21 and 4 | a | 1.94-1.99 (m, 2 H), 2.58-2.68 (m, 4 H), 2.78-2.81 (m, 2 H), 3.13-3.19 (m, 4 H), 3.26 (q, J = 6.5 Hz, 2 H), 3.99 (q, J = 7.0 Hz, 2 H) | | UV active |
| 2-9 | Isomer 2: Ethyl 2-{4-[cyclopropyl(2-methoxyethyl)amino]piperidin-1-yl}-6-azaspiro[3.4]octane-6-carboxylate | 13 and 4 | a | (400 MHz, MeOD-d₄) δ: 0.41-0.60 (m, 4 H), 1.27 (td, J = 7.0, 2.5 Hz, 3 H), 1.64-1.73 (m, 2 H), 1.86-2.00 (m, 9 H), 2.14-2.18 (m, 2 H), 2.68-2.89 (m, 4 H), 3.01-3.04 (m, 2 H), 3.34 (s, 3 H), 3.37-3.40 (m, 4 H), 3.53 (t, J = 6.0 Hz, 2 H), 4.12 (q, J = 7.0 Hz, 2 H) | I | m/z 380 (M + H)⁺ (ES⁺) at 4.38 min, UV active |
| 2-10 | Isomer 2: Ethyl 2-{4-[cyclopropyl(2-methoxy-2-oxoethyl)amino]piperidin-1-yl}-6-azaspiro[3.4]octane-6-carboxylate | 15 and 4 | a | (400 MHz, DMSO-d₆) δ: 0.28-0.34 (m, 2 H), 0.40-0.47 (m, 2 H), 1.16 (t, J = 7.0 Hz, 3 H), 1.32-1.41 (m, 2 H), 1.62 (t, J = 11.5 Hz, 2 H), 1.72-1.85 (m, 6 H), 1.94-1.98 (m, 2 H), 2.17-2.23 (m, 1 H), 2.55-2.79 (m, 2 H), 2.76-2.79 (m, 2 H), 3.14 (d, J = 6.5 Hz, 2 H), 3.24-3.29 (m, 2 H), 3.43 (s, 2 H), 3.59 (s, 3 H), 3.99 (q, J = 7.0 Hz, 2 H) | I | m/z 394 (M + H)⁺ (ES⁺) at 4.35 min, UV active |
| 2-11 | Isomer 2: Ethyl 2-{4-[cyclopropyl(1,2-oxazol-3-ylmethyl)amino]piperidin-1-yl}-6-azaspiro[3.4]octane-6-carboxylate | 4 and 35 | b | (400 MHz, CDCl₃) δ: 0.35-0.44 (m, 2 H), 0.48-0.60 (m, 2 H), 1.26 (t, J = 7.0 Hz, 2 H), 1.58-2.14 (m, 14 H), 2.49-3.08 (m, 3 H), 3.24-3.52 (m, 4 H), 3.95 (s, 2 H), 4.12 (q, J = 7.0 Hz, 2 H), 6.30 (s, 1 H), 8.34 (s, 1 H) | I | m/z 403 (M + H)⁺ (ES⁺) at 4.43 min, UV active |
| 2-12 | Isomer 2: Ethyl 2-(4-{[acetyl(cyclopropyl)amino]methyl}piperidin-1-yl)-6-azaspiro[3.4]octane-6-carboxylate | 4 and 36 | b | (400 MHz, CDCl₃) δ: 0.66-0.75 (m, 2 H), 0.80-0.93 (m, 2 H), 1.21-1.41 (m, 5 H), 1.59-2.10 (m, 11 H), 2.20 (s, 3 H), 2.59-2.76 (m, 2 H), 2.79-2.94 (m, 2 H), 3.19-3.44 (m, 6 H), 4.09 (q, J = 7.0 Hz, 2 H) | E | m/z 378 (M + H)⁺ (ES⁺) at 3.92 min, UV active |
| 2-13 | Isomer 2: Ethyl 2-(4-{[cyclopropyl(propanoyl)amino]methyl}piperidin-1-yl)-6-azaspiro[3.4]octane-6-carboxylate | 4 and 38 | b | (400 MHz, CDCl₃) δ: 0.64-0.73 (m, 2 H), 0.83-0.91 (m, 2 H), 1.12 (t, J = 7.5 Hz, 3 H), 1.21-1.40 (m, 5 H), 1.57-2.12 (m, 11 H), 2.45-2.72 (m, 4 H), 2.74-2.93 (m, 2 H), 3.17-3.44 (m, 6 H), 4.09 (q, J = 7.0 Hz, 2 H) | E | m/z 392 (M + H)⁺ (ES⁺) at 4.28 min, UV active |
| 2-14 | Isomer 2: Ethyl 2-{4-[1-[acetyl(cyclopropyl)amino]ethyl}piperidin-1-yl)-6-azaspiro[3.4]octane-6-carboxylate | 4 and 39 | b | (400 MHz, CDCl₃) δ: 0.70-0.89 (m, 4 H), 1.08-1.31 (m, 8 H), 1.46-2.09 (m, 11 H), 2.16 (s, 3 H), 2.54-2.72 (m, 2 H), 2.78-2.95 (m, 2 H), 3.23-3.41 (m, 5 H), 4.09 (q, J = 7.0 Hz, 2 H) | E | m/z 392 (M + H)⁺ (ES⁺) at 4.16 min, UV active |
| 2-15 | Isomer 2: Ethyl 2-(4-{1-[cyclopropyl(propanoyl)amino]ethyl}piperidin-1-yl)-6-azaspiro[3.4]octane-6-carboxylate | 4 and 23 | b | (400 MHz, CDCl₃) δ: 0.67-0.78 (m, 2 H), 0.79-0.94 (m, 2 H), 1.01-1.34 (m, 8 H), 1.50 (d, J = 11.5 Hz, 1 H), 1.57-2.15 (m, 10 H), 2.39-2.73 (m, 4 H), 2.75-2.98 (m, 2 H), 3.16-3.47 (m, 5 H), 4.09 (d, J = 7.0 Hz, 2 H) | E | m/z 406 (M + H)⁺ (ES⁺) at 4.52 min, UV active |
| 2-16 | Isomer 2: Methyl 2-{4-[acetyl(cyclobutyl)amino]piperidin-1-yl}-6-azaspiro[3.4]octane-6-carboxylate | 4 and 23 | a | (400 MHz, DMSO-d₆) δ: 1.22-1.41 (m, 1 H), 1.46-2.23 (m, 18 H), 2.35-2.45 (m, 1 H), 2.58-2.70 (m, 2 H), 2.73-2.92 (m, 3 H), 3.15 (d, J = 3.5 Hz, 2 H), 3.26-3.31 (m, 3 H), 3.56 (s, 3 H) | I | m/z 364 (M + H)⁺ (ES⁺) at 3.99 min, UV active |
| | Isomer 2: Ethyl 2-{4-[ethyl(formyl)amino]piperidin-1-yl}-6-azaspiro[3.4]octane-6-carboxylate | 4 and 42 | a | (400 MHz, MeOD-d₄) δ: 1.17 (t, J = 6.8 Hz, 2 H), 1.23-1.44 (m, 4 H), 1.56-1.95 (m, 9 H), 2.03-2.28 (m, 2 H), 2.67-2.92 (m, 1 H), 3.01 (d, J = 9.5 Hz, 2 H), 3.29 (s, 2 H), 3.38-3.46 (m, 4 H), 3.46-3.66 (m, 1 H), 4.11 (q, J = 6.8 Hz, 2 H), 4.66 (s, 1 H), 8.06-8.18 (m, 1 H) | I | m/z 338 (M + H)⁺ (ES⁺) at 3.50 min, UV active |

| Ex. No. | Name | Intermediate | Synthetic method | ¹H NMR | LCMS Method | LCMS data |
|---|---|---|---|---|---|---|
| 2-17 | Isomer 1: Methyl 2-{4-[acetyl(ethyl)amino]piperidin-1-yl}-6-azaspiro[3.4]octane-6-carboxylate | 41 and 53 | a | (400 MHz, DMSO-d₆) δ: 0.99 (t, J = 6.9 Hz, 1 H), 1.09 (t, J = 7.2 Hz, 2 H), 1.43-1.49 (m, 1 H), 1.57-1.83 (m, 9 H), 1.94-2.05 (m, 5 H), 2.57-2.66 (m, 2 H), 2.82 (d, J = 9.8 Hz, 2 H), 3.12-3.29 (m, 6 H), 3.57 (s, 3 H) | I | m/z 338 (M + H)⁺ (ES⁺) at 3.17 min, UV active |
| 2-17 | Isomer 2: Methyl 2-{4-[acetyl(ethyl)amino]piperidin-1-yl}-6-azaspiro[3.4]octane-6-carboxylate | 41 and 53 | a | (400 MHz, DMSO-d₆) δ: 0.98 (t, J = 6.7 Hz, 1 H), 1.08 (t, J = 7.0 Hz, 2 H), 1.42-1.51 (m, 1 H), 1.51-1.90 (m, 9 H), 1.91-2.04 (m, 5 H), 2.59-2.65 (m, 2 H), 2.80 (d, J = 10.4 Hz, 2 H), 3.08-3.32 (m, 6 H), 3.54 (s, 3 H) | I | m/z 338 (M + H)⁺ (ES⁺) at 3.24 min, UV active |
| 2-18 | Isomer 2: Ethyl 2-{4-[acetyl(propyl)amino]piperidin-1-yl}-6-azaspiro[3.4]octane-6-carboxylate | 4 and 46 | a | (400 MHz, DMSO-d₆) δ: 0.73-0.92 (m, 3 H), 1.16 (t, J = 7.0 Hz, 3 H), 1.35-1.54 (m, 3 H), 1.56-1.77 (m, 7 H), 1.77-1.88 (m, 2 H), 1.92-2.04 (m, 5 H), 2.59-2.66 (m, 1 H), 2.76-2.86 (m, 2 H), 2.99-3.12 (m, 2 H), 3.14 (d, J = 5.1 Hz, 2 H), 3.28 (d, J = 6.6 Hz, 2 H), 3.42-3.57 (m, 1 H), 4.00 (q, J = 7.1 Hz, 2 H) | I | m/z 366 (M + H)⁺ (ES⁺) at 3.82 min, UV active |
| 2-19 | Isomer 1: Ethyl 2-{4-[acetyl(2-methylpropyl)amino]piperidin-1-yl}-6-azaspiro[3.4]octane-6-carboxylate | 4 and 47 | a | (400 MHz, MeOD-d₄) δ: 0.90 (d, J = 6.8 Hz, 3 H), 0.98 (d, J = 6.8 Hz, 3 H), 1.17-1.34 (m, 3 H), 1.65-1.86 (m, 3 H), 1.86-1.96 (m, 6 H), 1.97-2.08 (m, 2 H), 2.10-2.19 (m, 5 H), 2.79 (t, J = 7.3 Hz, 1 H), 2.93-3.42 (m, 2 H), 3.17 (dd, J = 11.7, 7.8 Hz, 2 H), 3.33 (s, 2 H), 3.37-3.42 (m, 2 H), 3.61-3.95 (m, 1 H), 4.12 (q, J = 7.2 Hz, 2 H) | I | m/z 380 (M + H)⁺ (ES⁺) at 4.06 min, UV active |
| 2-19 | Isomer 2: Ethyl 2-{4-[acetyl(2-methylpropyl)amino]piperidin-1-yl}-6-azaspiro[3.4]octane-6-carboxylate | 4 and 47 | a | (400 MHz, MeOD-d₄) δ: 0.90 (d, J = 6.8 Hz, 3 H), 0.98 (d, J = 6.4 Hz, 3 H), 1.27 (t, J = 6.8 Hz, 3 H), 1.64-1.83 (m, 3 H), 1.85-2.14 (m, 11 H), 2.14-2.30 (m, 2 H), 2.80 (dq, J = 14.8, 7.6 Hz, 1 H), 2.92-3.06 (m, 2 H), 3.17 (dd, J = 11.7, 7.8 Hz, 2 H), 3.28 (s, 2 H), 3.40 (d, J = 6.4 Hz, 2 H), 3.64-3.96 (m, 1 H), 4.11 (q, J = 7.2 Hz, 2 H) | I | m/z 380 (M + H)⁺ (ES⁺) at 4.20 min, UV active |
| 2-20 | Isomer 1: Ethyl 2-{4-[acetyl(cyclopropylmethyl)amino]piperidin-1-yl}-6-azaspiro[3.4]octane-6-carboxylate | 4 and 50 | a | (400 MHz, MeOD-d₄) δ: 1.38-1.56 (m, 2 H), 1.58-1.70 (m, 1 H), 1.72-1.88 (m, 1 H), 2.02-2.30 (m, 1 H), 2.32-2.51 (m, 4 H), 2.85 (t, J = 11.8 Hz, 1 H), 2.89-3.19 (m, 9 H), 3.22-3.29 (m, 2 H), 3.80-4.01 (m, 1 H), 4.03-4.21 (m, 3 H), 4.36 (dd, J = 17.4, 6.4 Hz, 2 H), 4.43-4.63 (m, 5 H), 4.75-4.95 (m, 1 H), 5.26 (q, J = 7.0 Hz, 2 H) | I | m/z 378 (M + H)⁺ (ES⁺) at 3.79 min, UV active |
| 2-20 | Isomer 2: Ethyl 2-{4-[acetyl(cyclopropylmethyl)amino]piperidin-1-yl}-6-azaspiro[3.4]octane-6-carboxylate | 4 and 50 | a | (400 MHz, MeOD-d₄) δ: 1.48 (dd, J = 13.2, 5.1 Hz, 2 H), 1.63 (d, J = 7.3 Hz, 1 H), 1.78 (d, J = 7.5 Hz, 1 H), 2.04-2.26 (m, 1 H), 2.41 (t, J = 7.0 Hz, 4 H), 2.76-2.90 (m, 1 H), 2.90-3.05 (m, 3 H), 3.05-3.19 (m, 7 H), 3.28 (s, 2 H), 3.87-4.04 (m, 1 H), 4.06-4.22 (m, 2 H), 4.34 (d, J = 6.5 Hz, 1 H), 4.38 (d, J = 6.0 Hz, 1 H), 4.42 (s, 2 H), 4.45-4.48 (m, 1 H), 4.55 (q, J = 6.4 Hz, 2 H), 4.76-4.97 (m, 1 H), 5.25 (q, J = 7.0 Hz, 2 H) | I | m/z 378 (M + H)⁺ (ES⁺) at 3.90 min, UV active |
| 2-21 | Isomer 1: Ethyl 2-(4-{acetyl[(1-methylcyclobutyl)methyl]amino}piperidin-1-yl)-6-azaspiro[3.4]octane-6-carboxylate | 4 and 54 | a | (400 MHz, MeOD-d₄) δ: 1.13 (s, 1 H), 1.20-1.31 (m, 5 H), 1.56-1.67 (m, 2 H), 1.67-1.97 (m, 10 H), 1.98-2.28 (m, 8 H), 2.45 (q, J = 12.3 Hz, 1 H), 2.64-2.85 (m, 1 H), 2.97 (t, J = 9.5 Hz, 2 H), 3.26 (s, 2 H), 3.33-3.43 (m, 4 H), 3.59-3.76 (m, 1 H), 4.11 (q, J = 7.0 Hz, 2 H) | I | m/z 406 (M + H)⁺ (ES⁺) at 4.59 min, UV active |
| 2-21 | Isomer 2: Ethyl 2-(4-{acetyl[(1-methylcyclobutyl)methyl]amino}piperidin-1-yl)-6-azaspiro[3.4]octane-6- | 4 and 54 | a | (400 MHz, MeOD-d₄) δ: 1.12 (s, 1 H), 1.18-1.37 (m, 5 H), 1.45 (s, 1 H), 1.59-1.89 (m, 7 H), 1.89-1.98 (m, 4 H), 1.98-2.23 (m, 8 H), 2.31-2.56 (m, 1 H), 2.69-2.86 (m, 1 H), 2.98 (d, J = 10.1 Hz, 2 H), 3.26 (s, 2 H), 3.33-3.44 | I | m/z 406 (M + H)⁺ (ES⁺) at 4.71 min, UV active |

| Ex. No. | Name | Intermediate | Synthetic method | ¹H NMR | LCMS Method | LCMS data |
|---|---|---|---|---|---|---|
| | azaspiro[3.4]octane-6-carboxylate | | | (m, 4 H), 3.55-3.79 (m, 1 H), 4.09 (q, J = 7.0 Hz, 2 H) | | |
| 2-22 | Isomer 2: Ethyl 2-{4-[acetyl(1-methylcyclobutyl)amino]piperidin-1-yl}-6-azaspiro[3.4]octane-6-carboxylate | 4 and 56 | a | (400 MHz, MeOD-d₄) δ: 1.25 (t, J = 7.0 Hz, 3 H), 1.46-1.51 (m, 2 H), 1.52-1.60 (m, 2 H), 1.68-1.98 (m, 10 H), 2.08 (d, J = 8.5 Hz, 4 H), 2.13-2.32 (m, 2 H), 2.33-2.45 (m, 2 H), 2.71-2.88 (m, 3 H), 2.89-3.03 (m, 2 H), 3.26 (s, 2 H), 3.35-3.43 (m, 3 H), 4.09 (q, J = 6.7 Hz, 2 H) | I | m/z 392 (M + H)⁺ (ES⁺) at 4.54 min, UV active |
| 2-23 | Isomer 2: Ethyl 2-(4-{acetyl[(3-methyloxetan-3-yl)methyl]amino}piperidin-1-yl)-6-azaspiro[3.4]octane-6-carboxylate | 4, 57 and 58 | c | (400 MHz, MeOD-d₄) δ: 1.23-1.36 (m, 6 H), 1.71-1.81 (m, 4H), 1.87-2.03 (m, 6 H), 2.11-2.21 (m, 2 H), 2.18 (s, 3H), 2.77-2.88 (m, 1 H), 2.95-3.07 (m, 3 H), 3.27-3.31 (m, 2 H), 3.37-3.47 (m, 3 H), 3.68-3.79 (m, 1 H), 4.13 (q, J = 7.1 Hz, 2 H), 4.19 (d, J = 6.4 Hz, 2 H), 4.68-4.75 (m, 2 H) | I | m/z 408 (M + H)⁺ (ES⁺) at 3.58 min, UV active |
| 2-24 | Isomer 2: Ethyl 2-{4-[acetyl(2,2-difluoroethyl)amino]piperidin-1-yl}-6-azaspiro[3.4]octane-6-carboxylate | 4 and 60 | a | (400 MHz, DMSO-d₆) δ: 1.16 (t, J = 7.0 Hz, 3 H), 1.42-1.54 (m, 1 H), 1.58-1.66 (m, 3 H), 1.66-1.92 (m, 6 H), 1.92-2.05 (m, 3 H), 2.11 (s, 2 H), 2.63-2.70 (m, 1 H), 2.78-2.91 (m, 2 H), 3.08-3.20 (m, 2 H), 3.22-3.31 (m, 2 H), 3.45-3.66 (m, 2 H), 3.67-3.84 (m, 1 H), 4.00 (q, J = 7.0 Hz, 2 H), 5.86-6.35 (m, 1 H) | I | m/z 388 (M + H)⁺ (ES⁺) at 3.99 min, UV active |
| 2-25 | Isomer 2: Ethyl 2-{4-[acetyl(2,2,2-trifluoroethyl)amino]piperidin-1-yl}-6-azaspiro[3.4]octane-6-carboxylate | 4 and 62 | a | (400 MHz, DMSO-d₆) δ: 1.16 (t, J = 7.0 Hz, 3 H), 1.51 (d, J = 10.4 Hz, 1 H), 1.57-1.87 (m, 9 H), 1.96-2.02 (m, 2 H), 2.05 (s, 1 H), 2.14 (s, 2 H), 2.56-2.72 (m, 1 H), 2.75-2.89 (m, 2 H), 3.14 (d, J = 5.5 Hz, 2 H), 3.26-3.35 (m, 2 H), 3.57-3.87 (m, 1 H), 3.94-4.12 (m, 3 H), 4.21 (q, J = 9.0 Hz, 1 H) | I | m/z 406 (M + H)⁺ (ES⁺) at 4.05 min, UV active |
| 2-26 | Isomer 1: Ethyl 2-{4-[acetyl(2-fluoro-2-methylpropyl)amino]piperidin-1-yl}-6-azaspiro[3.4]octane-6-carboxylate | 4 and 64 | a | (400 MHz, MeOD-d₄) δ: 1.20-1.33 (m, 6 H), 1.35 (s, 2 H), 1.38 (s, 1 H), 1.43 (s, 1 H), 1.67-1.82 (m, 2 H), 1.82-2.05 (m, 7 H), 2.06-2.19 (m, 2 H), 2.23 (s, 2 H), 2.33-2.51 (m, 1 H), 2.78 (sxt, J = 8.3 Hz, 1 H), 2.92-3.06 (m, 2 H), 3.37 (s, 3 H), 3.42-3.80 (m, 3 H), 4.12 (q, J = 6.8 Hz, 2H) | I | m/z 398 (M + H)⁺ (ES⁺) at 3.94 min, UV active |
| 2-26 | Isomer 2: Ethyl 2-{4-[acetyl(2-fluoro-2-methylpropyl)amino]piperidin-1-yl}-6-azaspiro[3.4]octane-6-carboxylate | 4 and 64 | a | (400 MHz, MeOD-d₄) δ: 1.21-1.32 (m, 6 H), 1.35 (s, 2 H), 1.38 (s, 1 H), 1.44 (s, 1 H), 1.70-1.86 (m, 2 H), 1.86-2.06 (m, 7 H), 2.06-2.19 (m, 3 H), 2.23 (s, 2 H), 2.36-2.55 (m, 1 H), 2.73-2.94 (m, 1 H), 3.02 (d, J = 6.4 Hz, 2 H), 3.36-3.48 (m, 3 H), 3.48-3.82 (m, 3 H), 4.11 (q, J = 6.8 Hz, 2 H) | I | m/z 398 (M + H)⁺ (ES⁺) at 4.05 min, UV active |
| 2-27 | Isomer 2: Ethyl 2-{4-[acetyl(2,2-difluoropropyl)amino]piperidin-1-yl}-6-azaspiro[3.4]octane-6-carboxylate | 4 and 66 | a | (400 MHz, MeOD-d₄) δ: 1.24 (t, J = 7.0 Hz, 3 H), 1.55-1.64 (m, 2 H), 1.69-1.97 (m, 10 H), 2.05-2.25 (m, 6 H), 2.71-2.85 (m, 1 H), 2.97 (t, J = 10.1 Hz, 2 H), 3.26 (s, 2 H), 3.34-3.42 (m, 2 H), 3.68-3.86 (m, 3 H), 4.09 (q, J = 6.9 Hz, 2 H) | I | m/z 402 (M + H)⁺ (ES⁺) at 3.95 min, UV active |
| 2-28 | Isomer 2: Ethyl 2-{4-[acetyl(3,3-difluorocyclobutyl)amino]piperidin-1-yl}-6-azaspiro[3.4]octane-6-carboxylate | 4 and 68 | a | (400 MHz, MeOD-d₄) δ: 1.25 (t, J = 7.0 Hz, 3 H), 1.49-2.01 (m, 9 H), 2.07-2.22 (m, 5 H), 2.45-2.71 (m, 2 H), 2.80 (quin, J = 7.9 Hz, 1 H), 2.97 (d, J = 11.0 Hz, 2 H), 3.22-3.27 (m, 2 H), 3.40 (q, J = 6.7 Hz, 3 H), 3.48-3.89 (m, 4 H), 4.10 (q, J = 7.1 Hz, 2 H) | I | m/z 414 (M + H)⁺ (ES⁺) at 3.85 min, UV active |
| 2-29 | Isomer 1: Ethyl 2-{4-[acetyl(2-methoxy-2- | 4 and 70 | a | (400 MHz, MeOD-d₄) δ: 1.15 (s, 3 H), 1.22 (s, 3 H), 1.24-1.32 (m, 3 H), 1.66-1.80 (m, 3 H), 1.85-2.04 (m, 5 H), | I | m/z 410 (M + H)⁺ (ES⁺) at 3.98 min, |

TABLE 3-continued

| Ex. No. | Name | Intermediate | Synthetic method | ¹H NMR | LCMS Method | LCMS data |
|---|---|---|---|---|---|---|
| | methylpropyl)amino]piperidin-1-yl}-6-azaspiro[3.4]octane-6-carboxylate | | | 2.04-2.18 (m, 5 H), 2.21 (s, 1 H), 2.50-2.68 (m, 1 H), 2.69-2.85 (m, 1 H), 2.90-3.06 (m, 2 H), 3.23 (d, J = 2.9 Hz, 3 H), 3.35-3.44 (m, 5 H), 3.48-3.53 (m, 1 H), 3.58-3.72 (m, 1 H), 4.12 (q, J = 6.8 Hz, 2 H) | | UV active |
| 2-29 | Isomer 2: Ethyl 2-{4-[acetyl(2-methoxy-2-methylpropyl)amino]piperidin-1-yl}-6-azaspiro[3.4]octane-6-carboxylate | 4 and 70 | a | (400 MHz, MeOD-d₄) δ: 1.15 (s, 3 H), 1.22 (s, 3 H), 1.27 (t, J = 7.1 Hz, 3 H), 1.67-1.86 (m, 3 H), 1.86-1.99 (m, 5 H), 2.03-2.19 (m, 5 H), 2.21 (s, 1 H), 2.50-2.66 (m, 1 H), 2.71-2.89 (m, 1 H), 2.92-3.06 (m, 2 H), 3.23 (d, J = 3.9 Hz, 3 H), 3.28 (br. s., 2 H), 3.38-3.42 (m, 4 H), 3.56-3.76 (m, 1 H), 4.11 (q, J = 6.8 Hz, 2 H) | I | m/z 410 (M + H)⁺ (ES⁺) at 4.12 min, UV active |
| 2-30 | Isomer 1: Ethyl 2-{4-[acetyl[(1-methoxycyclobutyl)methyl]amino]piperidin-1-yl)-6-azaspiro[3.4]octane-6-carboxylate | 4 and 71 | a | (400 MHz, DMSO-d₆) δ: 1.17 (t, J = 6.6 Hz, 3 H), 1.40-1.69 (m, 4 H), 1.69-1.88 (m, 8 H), 1.90-2.05 (m, 4 H), 2.10 (br. s., 2 H), 2.12-2.23 (m, 1 H), 2.23-2.42 (m, 1 H), 2.57-2.72 (m, 1 H), 2.73-2.95 (m, 2 H), 3.08-3.18 (m, 4 H), 3.18-3.29 (m, 4 H), 3.40-3.64 (m, 3 H), 4.01 (q, J = 7.3 Hz, 2 H) | I | m/z 422 (M + H)⁺ (ES⁺) at 4.03 min, UV active |
| 2-30 | Isomer 2: Ethyl 2-{4-[acetyl[(1-methoxycyclobutyl)methyl]amino]piperidin-1-yl)-6-azaspiro[3.4]octane-6-carboxylate | 4 and 71 | a | (400 MHz, DMSO-d₆) δ: 1.16 (t, J = 7.1 Hz, 3 H), 1.47-1.56 (m, 4 H), 1.66-1.88 (m, 9 H), 1.90-2.20 (m, 7 H), 2.22-2.37 (m, 1 H), 2.55-2.70 (m, 1 H), 2.76-2.83 (m, 2 H), 3.09-3.20 (m, 5 H), 3.27 (q, J = 6.5 Hz, 2 H), 3.40-3.60 (m, 3 H), 4.00 (d, J = 7.3 Hz, 2 H) | I | m/z 422 (M + H)⁺ (ES⁺) at 4.16 min, UV active |
| 2-31 | Isomer 1: Ethyl 2-{4-[acetyl[(1-hydroxycyclobutyl)methyl]amino]piperidin-1-yl)-6-azaspiro[3.4]octane-6-carboxylate | 4 and 74 | a | (400 MHz, MeOD-d₄) δ: 1.22-1.36 (m, 3 H), 1.56-2.28 (m, 20 H), 2.46-2.63 (m, 1 H), 2.74-2.91 (m, 1 H), 2.93-3.08 (m, 1 H), 3.36-3.44 (m, 4 H), 3.46-3.59 (m, 2 H), 3.70-3.82 (m, 1 H), 4.09-4.18 (m, 2 H). One exchangeable proton not observed. | I | m/z 408 (M + H)⁺ (ES⁺) at 3.58 min, UV active |
| 2-31 | Isomer 2: Ethyl 2-{4-[acetyl[(1-hydroxycyclobutyl)methyl]amino]piperidin-1-yl)-6-azaspiro[3.4]octane-6-carboxylate | 4 and 74 | a | (400 MHz, MeOD-d₄) δ: 1.28 (t, J = 7.0 Hz, 3 H), 1.57-2.28 (m, 20 H), 2.45-2.59 (m, 1 H), 2.75-2.91 (m, 1 H), 2.92-3.08 (m, 2 H), 3.25-3.32 (m, 5 H), 3.38-3.46 (m, 2 H), 3.48-3.61 (m, 2 H), 3.70-3.84 (m, 1 H), 4.13 (q, J = 6.9 Hz, 2 H). One exchangeable proton not observed. | I | m/z 408 (M + H)⁺ (ES⁺) at 3.64 min, UV active |
| 2-32 | Isomer mixture: Ethyl 2-{4-[acetyl(methoxy)amino]piperidin-1-yl}-6-azaspiro[3.4]octane-6-carboxylate | 4 and 76 | a | (400 MHz, MeOD-d₄) δ: 1.27 (t, J = 6.8 Hz, 3 H), 1.80 (d, J = 11.7 Hz, 2 H), 1.84-2.03 (m, 8 H), 2.11 (d, J = 2.4 Hz, 2 H), 2.16 (s, 3 H), 2.80 (quin, J = 7.9 Hz, 1 H), 3.00 (d, J = 10.3 Hz, 2 H), 3.29 (s, 2 H), 3.41 (q, J = 6.5 Hz, 2 H), 3.82 (s, 3 H), 4.11 (q, J = 7.3 Hz, 2 H) | I | m/z 354 (M + H)⁺ (ES⁺) at 3.59 min, UV active |
| 2-33 | Isomer mixture: Ethyl 2-{4-[acetyl(phenyl)amino]piperidin-1-yl}-6-azaspiro[3.4]octane-6-carboxylate | 4 and 78 | a | (400 MHz, DMSO-d₆) δ: 0.96-1.32 (m, 5 H), 1.52-2.06 (m, 10 H), 2.40-2.85 (m, 5 H), 2.98-3.29 (m, 5 H), 3.83-4.16 (m, 2 H), 4.25-4.61 (m, 1 H), 7.06-7.32 (m, 2 H), 7.32-7.61 (m, 3 H) | I | m/z 400 (M + H)⁺ (ES⁺) at 4.09 min, UV active |
| 2-34 | Isomer mixture: Ethyl 2-{4-[acetyl(pyridin-2-yl)amino]piperidin-1-yl}-6-azaspiro[3.4]octane-6-carboxylate | 4 and 80 | a | (400 MHz, MeOD-d₄) δ: 1.20-1.38 (m, 4 H), 1.38-1.56 (m, 2 H), 1.72-2.01 (m, 12 H), 2.02-2.15 (m, 2 H), 2.69-2.81 (m, 1 H), 2.85-2.99 (m, 2 H), 3.21-3.45 (m, 2 H), 4.05-4.16 (m, 2 H), 4.44-4.54 (m, 1 H), 7.42 (d, J = 7.9 Hz, 1 H), 7.53 (ddd, J = 7.6, 5.0, 0.9 Hz, 1 H), 8.02 (td, J = 7.7, 2.0 Hz, 1 H), 8.61 (dt, J = 4.4, 1.3 Hz, 1 H) | I | m/z 401 (M + H)⁺ (ES⁺) at 3.39 min, UV active |
| 2-35 | Isomer 2: Ethyl 2-{4-[acetyl(benzyl)amino]piperidin-1-yl}-6-azaspiro[3.4]octane-6-carboxylate | 4 and 82 | a | (400 MHz, DMSO-d₆) δ: 1.09-1.24 (m, 3 H), 1.38-1.60 (m, 4 H), 1.61-1.75 (m, 4 H), 1.75-1.87 (m, 2 H), 1.91-1.97 (m, 4 H), 2.18 (s, 2 H), 2.71-2.79 (m, 3 H), 3.11 (dd, J = 6.1, 3.4 Hz, 2 H), 3.20-3.31 (m, 2 H), 3.93-4.05 (m, | I | m/z 414 (M + H)⁺ (ES⁺) at 4.14 min, UV active |

TABLE 3-continued

| Ex. No. | Name | Intermediate | Synthetic method | $^1$H NMR | LCMS Method | LCMS data |
|---|---|---|---|---|---|---|
| 2-36 | Isomer 2: Ethyl 2-{4-[acetyl(1,3-oxazol-5-ylmethyl)amino]piperidin-1-yl}-6-azaspiro[3.4]octane-6-carboxylate | 4 and 90 | a | 2 H), 4.43-4.63 (m, 2 H), 7.13-7.31 (m, 4 H), 7.32-7.42 (m, 1 H) (400 MHz, DMSO-d$_6$) δ: 1.16 (t, J = 7.1 Hz, 3 H), 1.51-1.88 (m, 8 H), 1.89-2.09 (m, 4 H), 2.40-2.69 (m, 5 H), 2.75-2.88 (m, 2 H), 3.07-3.19 (m, 2 H), 3.20-3.29 (m, 2 H), 3.99 (q, J = 7.1 Hz, 2 H), 4.39-4.66 (m, 2 H), 6.88-7.17 (m, 1 H), 8.16-8.36 (m, 1 H) | I | m/z 405 (M + H)$^+$ (ES$^+$) at 3.38 min, UV active |
| 2-37 | Isomer 2: Ethyl 2-{4-[acetyl(1,3-oxazol-2-ylmethyl)amino]piperidin-1-yl}-6-azaspiro[3.4]octane-6-carboxylate | 4 and 93 | a | (400 MHz, DMSO-d$_6$) δ: 1.27 (t, J = 7.1 Hz, 3 H), 1.66-2.03 (m, 10 H), 2.04-2.29 (m, 5 H), 2.71-2.89 (m, 1 H), 2.96-3.05 (m, 2 H), 3.21-3.45 (m, 4 H), 3.82-3.96 (m, 1 H), 4.10 (q, J = 7.1 Hz, 2 H), 4.61-4.77 (m, 2 H), 7.03-7.25 (m, 1 H), 7.82-7.98 (m, 1 H) | I | m/z 405 (M + H)$^+$ (ES$^+$) at 4.36 min, UV active |
| 2-38 | Isomer 2: (1,1-$^2$H$_2$)-Ethyl 2-{4-[acetyl(ethyl)amino]piperidin-1-yl}-6-azaspiro[3.4]octane-6-carboxylate | 114, 3, 115 and 116 | d | (400 MHz, MeOD-d$_4$) δ: 1.11-1.33 (m, 6 H), 1.64-2.02 (m, 10 H), 2.08-2.20 (m, 4 H), 2.75-2.86 (m, 1 H), 2.96-3.06 (m, 2 H), 3.29 (s, 2 H), 3.35-3.45 (m, 4 H), 3.66-3.77 (m, 1 H), 4.21-4.34 (m, 1 H) | E | m/z 354 (M + H)$^+$ (ES$^+$) at 3.37 min, UV active |
| 2-39 | Isomer 2: Ethyl 2-{4-[ethyl(methoxycarbonyl)amino]piperidin-1-yl}-6-azaspiro[3.4]octane-6-carboxylate | 4 and 94 | a | (400 MHz, MeOD-d$_4$) δ: 1.15 (t, J = 7.0 Hz, 3 H), 1.27 (t, J = 7.1 Hz, 3 H), 1.64-2.00 (m, 10 H), 2.13 (ddd, J = 9.7, 7.3, 2.6 Hz, 2 H), 2.80 (t, J = 8.0 Hz, 1 H), 2.99 (d, J = 11.5 Hz, 2 H), 3.19-3.45 (m, 6 H), 3.70 (s, 3 H), 3.79-3.93 (m, 1 H), 4.11 (q, J = 7.2 Hz, 2 H) | I | m/z 368 (M + H)$^+$ (ES$^+$) at 4.26 min, UV active |
| 2-40 | Isomer 2: Ethyl 2-{4-[(ethoxycarbonyl)(ethyl)amino]piperidin-1-yl}-6-azaspiro[3.4]octane-6-carboxylate | 4 and 95 | a | (400 MHz, DMSO-d$_6$) δ: 1.03 (t, J = 6.9 Hz, 3 H), 1.16 (t, J = 7.2 Hz, 6 H), 1.46-1.81 (m, 6 H), 1.94-2.04 (m, 4 H), 2.77-2.86 (m, 2 H), 3.07-3.15 (m, 4 H), 3.16-3.49 (m, 6 H), 4.01 (dd, J = 8.6, 6.9 Hz, 4 H) | I | m/z 382 (M + H)$^+$ (ES$^+$) at 4.52 min, UV active |
| 2-41 | Isomer 2: Ethyl 2-{4-[(methoxycarbonyl)(propan-2-yl)amino]piperidin-1-yl}-6-azaspiro[3.4]octane-6-carboxylate | 4 and 96 | a | (400 MHz, MeOD-d$_4$) δ: 1.18-1.31 (m, 9 H), 1.52-1.63 (m, 2 H), 1.82-2.04 (m, 6 H), 2.04-2.17 (m, 4 H), 2.80 (t, J = 7.5 Hz, 1 H), 2.89-3.00 (m, 2 H), 3.24-3.44 (m, 6 H), 3.69 (s, 3 H), 4.11 (q, J = 7.1 Hz, 2 H) | I | m/z 382 (M + H)$^+$ (ES$^+$) at 4.36 min, UV active |
| 2-42 | Isomer 2: Ethyl 2-{4-[(methoxycarbonyl)(2,2,2-trifluoroethyl)amino]piperidin-1-yl}-6-azaspiro[3.4]octane-6-carboxylate | 4 and 98 | a | (400 MHz, MeOD-d$_4$) δ: 1.22-1.30 (m, 3 H), 1.72-1.80 (m, 2 H), 1.82-2.01 (m, 8 H), 2.07-2.17 (m, 2 H), 2.73-2.85 (m, 1 H), 2.94-3.04 (m, 2 H), 3.24-3.29 (m, 2 H), 3.36-3.45 (m, 1 H), 3.58-3.70 (m, 1 H), 3.70-3.80 (m, 3 H), 3.95-4.06 (m, 2 H), 4.07-4.16 (m, 2 H) | I | m/z 422 (M + H)$^+$ (ES$^+$) at 4.67 min, UV active |
| 2-43 | Isomer 2: Ethyl 2-(4-{[(2-methoxyethoxy)carbonyl](2,2,2-trifluoroethyl)amino}piperidin-1-yl)-6-azaspiro[3.4]octane-6-carboxylate | 4 and 99 | a | (400 MHz, MeOD-d$_4$) δ: 1.27 (t, J = 7.1 Hz, 3 H), 1.46-1.60 (m, 2 H), 1.76-2.00 (m, 9 H), 2.08-2.18 (m, 2 H), 2.59-2.89 (m, 4 H), 2.93-3.02 (m, 2 H), 3.17-3.50 (m, 10 H), 4.11 (d, J = 7.1 Hz, 2 H) | I | m/z 467 (M + H)$^+$ (ES$^+$) at 4.56 min, UV active |
| 2-44 | Isomer 2: Ethyl 2-{4-[(dimethylcarbamoyl)(ethyl)amino]piperidin-1-yl}-6-azaspiro[3.4]octane-6-carboxylate | 4 and 101 | a | (400 MHz, MeOD-d$_4$) δ: 1.10 (t, J = 6.8 Hz, 3 H), 1.27 (t, J = 7.1 Hz, 3 H), 1.79-1.91 (m, 2 H), 1.92-2.18 (m, 6 H), 2.21-2.32 (m, 2 H), 2.35-2.52 (m, 2 H), 2.87 (s, 6 H), 3.12-3.57 (m, 10 H), 4.12 (d, J = 7.1 Hz, 2 H) | I | m/z 381 (M + H)$^+$ (ES$^+$) at 3.92 min, UV active |

TABLE 3-continued

| Ex. No. | Name | Intermediate | Synthetic method | ¹H NMR | LCMS Method | LCMS data |
|---|---|---|---|---|---|---|
| 2-45 | Isomer 2: Ethyl 2-{4-[ethyl(2-fluoroethyl)amino]piperidin-1-yl}-6-azaspiro[3.4]octane-6-carboxylate | 4 and 103 | a | (400 MHz, DMSO-d₆) δ: 0.96 (t, J = 7.1 Hz, 3 H), 1.16 (t, J = 7.1 Hz, 3 H), 1.27-1.45 (m, 2 H), 1.49-2.06 (m, 10 H), 2.24-2.90 (m, 8 H), 3.04-3.34 (m, 6 H), 3.99 (d, J = 7.1 Hz, 2 H) | I | m/z 356 (M + H)⁺ (ES⁺) at 4.17 min, UV active |
| 2-46 | Isomer 2: Ethyl 2-{4-[(2,2-difluoroethyl)(ethyl)amino]piperidin-1-yl}-6-azaspiro[3.4]octane-6-carboxylate | 4 and 105 | a | (400 MHz, DMSO-d₆) δ: 0.95 (t, J = 7.1 Hz, 3 H), 1.10-1.22 (m, 3 H), 1.26-1.41 (m, 2 H), 1.57-1.80 (m, 8 H), 1.93-2.06 (m, 2 H), 2.37-2.66 (m, 5 H), 2.69-2.85 (m, 4 H), 3.15-3.30 (m, 4 H), 4.01 (q, J = 7.1 Hz, 2 H) | I | m/z 375 (M + H)⁺ (ES⁺) at 4.56 min, UV active |
| 2-47 | Isomer 2: Ethyl 2-{4-[(methoxycarbonyl)(oxetan-3-yl)amino]piperidin-1-yl}-6-azaspiro[3.4]octane-6-carboxylate | 4, 57, 106 and 40 | c | (400 MHz, MeOD-d₄) δ: 1.28 (t, J = 7.3 Hz, 3 H), 1.62-1.72 (m, 2 H), 1.89-2.06 (m, 6 H), 2.09-2.20 (m, 2 H), 2.76-2.90 (m, 1 H), 2.96-3.04 (m, 2 H), 3.30 (s, 2 H), 3.37-3.48 (m, 4 H), 3.62-3.73 (m, 1 H), 3.75 (s, 3 H), 4.13 (q, J = 7.1 Hz, 2 H), 4.71-4.78 (m, 2 H), 4.81-5.00 (m, 3 H) | I | m/z 396 (M + H)⁺ (ES⁺) at 3.96 min, UV active |
| 2-48 | Isomer 2: Ethyl 2-{4-[cyclopropyl(2,2,2-trifluoroethyl)amino]piperidin-1-yl}-6-azaspiro[3.4]octane-6-carboxylate | 4 and 109 | a | (400 MHz, DMSO-d₆) δ: 0.33-0.52 (m, 4 H), 1.16 (t, J = 7.1 Hz, 3 H), 1.42-1.88 (m, 10 H), 1.92-2.02 (m, 2 H), 2.13-2.23 (m, 1 H), 2.54-2.67 (m, 2 H), 2.76-2.86 (m, 2 H), 3.14 (d, J = 5.8 Hz, 2 H), 3.22-3.36 (m, 4 H), 3.99 (q, J = 7.1 Hz, 2 H) | I | m/z 404 (M + H)⁺ (ES⁺) at 5.47 min, UV active |
| 2-49 | Isomer 2: Ethyl 2-{4-[cyclopropyl(2-hydroxyethyl)amino]piperidin-1-yl}-6-azaspiro[3.4]octane-6-carboxylate | 4 and 111 | a | (400 MHz, MeOD-d₄) δ: 0.40-0.63 (m, 4 H), 0.87-0.99 (m, 1 H), 1.19-1.36 (m, 3 H), 1.57-1.78 (m, 3 H), 1.82-2.05 (m, 8 H), 2.07-2.25 (m, 2 H), 2.77-2.88 (m, 4 H), 2.94-3.07 (m, 2 H), 3.25-3.55 (m, 4 H), 3.60-3.75 (m, 2 H), 4.11 (d, J = 7.1 Hz, 2 H) | I | m/z 366 (M + H)⁺ (ES⁺) at 3.76 min, UV active |
| 2-50 | Isomer 2: Ethyl 2-{4-[cyclobutyl(2-hydroxyethyl)amino]piperidin-1-yl}-6-azaspiro[3.4]octane-6-carboxylate | 4 and 113 | a | (400 MHz, DMSO-d₆) δ: 1.16 (t, J = 7.1 Hz, 3 H), 1.21-1.43 (m, 2 H), 1.46-1.67 (m, 5 H), 1.67-2.02 (m, 10 H), 2.30-2.49 (m, 4 H), 2.65-2.71 (m, 1 H), 2.75-2.83 (m, 2 H), 3.11-3.17 (m, 2 H), 3.23-3.33 (m, 4 H), 3.99 (d, J = 7.1 Hz, 2 H), 4.26-4.32 (m, 1 H) | I | m/z 380 (M + H)⁺ (ES⁺) at 3.95 min, UV active |
| 2-51 | Isomer 2: Ethyl 2-{4-[(2-hydroxyethyl)(2,2,2-trifluoroethyl)amino]piperidin-1-yl}-6-azaspiro[3.4]octane-6-carboxylate | 4 and 117 | a | (400 MHz, MeOD-d₄) δ: 1.28 (t, J = 7.1 Hz, 3 H), 1.54-1.69 (m, 2 H), 1.83-1.94 (m, 2 H), 1.93-2.16 (m, 6 H), 2.15-2.25 (m, 2 H), 2.69-2.79 (m, 1 H), 2.82 (t, J = 6.6 Hz, 2 H), 2.95-3.06 (m, 1 H), 3.06-3.18 (m, 2 H), 3.20-3.33 (m, 4 H), 3.44 (q, J = 7.1 Hz, 2 H), 3.60 (t, J = 6.6 Hz, 2 H), 4.14 (q, J = 7.2 Hz, 2 H). One exchangeable proton not observed. | I | m/z 408 (M + H)⁺ (ES⁺) at 4.25 min, UV active |

TABLE 3-continued

| Ex. No. | Name | Intermediate | Synthetic method | ¹H NMR | LCMS Method | LCMS data |
|---|---|---|---|---|---|---|
| 2-52 | Isomer 2: Ethyl 2-{4-[(2-methoxyethyl)(2,2,2-trifluoroethyl)amino]piperidin-1-yl}-6-azaspiro[3.4]octane-6-carboxylate | 4 and 119 | a | (400 MHz, MeOD-d₄) δ: 1.28 (t, J = 7.1 Hz, 3 H), 1.48-1.60 (m, 2 H), 1.78-1.88 (m, 4 H), 1.88-2.02 (m, 4 H), 2.09-2.18 (m, 2 H), 2.61-2.72 (m, 1 H), 2.73-2.83 (m, 1 H), 2.86 (t, J = 6.2 Hz, 2 H), 2.98 (d, J = 12.0 Hz, 1 H), 3.19-3.31 (m, 4 H), 3.35 (s, 3 H), 3.42 (q, J = 7.0 Hz, 2 H), 3.47 (t, J = 6.1 Hz, 2 H), 4.12 (q, J = 7.1 Hz, 2 H) | I | m/z 422 (M + H)⁺ (ES⁺) at 4.97 min, UV active |
| 2-53 | Isomer 2: Ethyl 2-{4-[ethyl(oxetan-3-yl)amino]piperidin-1-yl}-6-azaspiro[3.4]octane-6-carboxylate | 4 and 120 | a | (400 MHz, MeOD-d₄) δ: 1.07 (t, J = 7.1 Hz, 3 H), 1.28 (t, J = 7.1 Hz, 3 H), 1.39-1.59 (m, 2 H), 1.65-1.78 (m, 2 H), 1.81-2.02 (m, 6 H), 2.09-2.18 (m, 2 H), 2.51-2.64 (m, 1 H), 2.73 (q, J = 7.0 Hz, 2 H), 2.76-2.86 (m, 1 H), 2.99 (d, J = 11.7 Hz, 2 H), 3.29 (s, 2 H), 3.41 (q, J = 6.8 Hz, 2 H), 4.09-4.23 (m, 3 H), 4.64-4.71 (m, 4 H) | I | m/z 366 (M + H)⁺ (ES⁺) at 3.66 min, UV active |
| 2-54 | Isomer 2: Ethyl 2-{4-[oxetan-3-yl(2,2,2-trifluoroethyl)amino]piperidin-1-yl}-6-azaspiro[3.4]octane-6-carboxylate | 4 and 122 | a | (400 MHz, MeOD-d₄) δ: 1.28 (t, J = 7.1 Hz, 3 H), 1.39-1.52 (m, 2 H), 1.72 (d, J = 12.8 Hz, 2 H), 1.78-2.00 (m, 6 H), 2.09-2.18 (m, 2 H), 2.60-2.71 (m, 1 H), 2.72-2.84 (m, 1 H), 2.97 (d, J = 9.8 Hz, 2 H), 3.29 (s, 2 H), 3.41 (q, J = 6.4 Hz, 2 H), 3.50 (q, J = 9.5 Hz, 2 H), 4.12 (q, J = 6.8 Hz, 2 H), 4.33-4.40 (m, 1 H), 4.63 (t, J = 6.6 Hz, 2 H), 4.74 (t, J = 7.2 Hz, 2 H) | I | m/z 420 (M + H)⁺ (ES⁺) at 4.49 min, UV active |
| 2-55 | Isomer 2: Ethyl 2-{4-[(2-cyanoethyl)(ethyl)amino]piperidin-1-yl}-6-azaspiro[3.4]octane-6-carboxylate | 4 and 124 | a | (400 MHz, MeOD-d₄) δ: 1.09 (t, J = 7.1 Hz, 3 H), 1.28 (t, J = 7.1 Hz, 3 H), 1.50-1.63 (m, 2 H), 1.79-1.89 (m, 4 H), 1.89-2.02 (m, 4 H), 2.10-2.20 (m, 2 H), 2.55 (t, J = 6.8 Hz, 2 H), 2.65 (q, J = 7.2 Hz, 2 H), 2.73-2.86 (m, 4 H), 2.98 (d, J = 12.0 Hz, 2 H), 3.29 (s, 2 H), 3.42 (q, J = 6.9 Hz, 2 H), 4.12 (q, J = 7.1 Hz, 2 H) | I | m/z 363 (M + H)⁺ (ES⁺) at 4.20 min, UV active |
| 2-56 | Isomer 2: Ethyl 2-(4-{ethyl[2-(methylsulfonyl)ethyl]amino}piperidin-1-yl)-6-azaspiro[3.4]octane-6-carboxylate | 4 and 126 | a | (400 MHz, MeOD-d₄) δ: 1.10 (t, J = 7.2 Hz, 3 H), 1.28 (t, J = 7.0 Hz, 3 H), 1.54-1.67 (m, 2 H), 1.77-2.02 (m, 8 H), 2.09-2.19 (m, 2 H), 2.58-2.70 (m, 3 H), 2.74-2.84 (m, 1 H), 2.95-3.08 (m, 7 H), 3.22-3.31 (m, 4 H), 3.42 (q, J = 6.5 Hz, 2 H), 4.12 (q, J = 7.0 Hz, 2 H) | I | m/z 416 (M + H)⁺ (ES⁺) at 3.74 min, UV active |
| 2-57 | Isomer 2: Ethyl 2-{4-[ethyl(methoxy)amino]piperidin-1-yl}-6-azaspiro[3.4]octane-6-carboxylate | 4 and 128 | a | (400 MHz, MeOD-d₄) δ: 1.17 (t, J = 7.0 Hz, 3 H), 1.28 (t, J = 7.1 Hz, 3 H), 1.57-1.69 (m, 2 H), 1.82-2.00 (m, 8 H), 2.09-2.17 (m, 2 H), 2.56-2.66 (m, 1 H), 2.74-2.86 (m, 3 H), 2.96 (d, J = 11.7 Hz, 2 H), 3.29 (s, 2 H), 3.42 (q, J = 6.8 Hz, 2 H), 3.56 (s, 3 H), 4.12 (q, J = 6.8 Hz, 2 H) | I | m/z 340 (M + H)⁺ (ES⁺) at 4.30 min, UV active |
| 2-58 | Isomer 2: Ethyl 2-{4-[(2-hydroxyethyl)(phenyl)amino]piperidin-1-yl}-6-azaspiro[3.4]octane-6-carboxylate | 4 and 130 | a | (400 MHz, DMSO-d₆) δ: 1.18 (t, J = 7.1 Hz, 3 H), 1.56-1.70 (m, 4 H), 1.74-1.90 (m, 6 H), 1.91-2.08 (m, 2 H), 2.64-2.73 (m, 1 H), 2.86 (d, J = 11.7 Hz, 2 H), 3.17 (d, J = 4.1 Hz, 2 H), 3.19-3.35 (m, 4 H), 3.40-3.48 (m, 2 H), 3.49-3.59 (m, 1 H), 4.01 (q, J = 7.1 Hz, 2 H), 4.78 (br. s, 1 H), 6.59 (t, J = 7.2 Hz, 1 H), 6.75 (d, J = 8.3 Hz, 2 H), 7.12-7.18 (m, 2 H) | I | m/z 402 (M + H)⁺ (ES⁺) at 4.72 min, UV active |

TABLE 3-continued

| Ex. No. | Name | Intermediate | Synthetic method | $^1$H NMR | LCMS Method | LCMS data |
|---|---|---|---|---|---|---|
| 2-59 | Isomer 2: Ethyl 2-{4-[benzyl(2,2,2-trifluoroethyl)amino]piperidin-1-yl}-6-azaspiro[3.4]octane-6-carboxylate | 4 and 132 | a | (400 MHz, DMSO-d$_6$) δ: 1.17 (t, J = 7.0 Hz, 3 H), 1.36-1.50 (m, 2 H), 1.49-1.61 (m, 2 H), 1.63-1.77 (m, 4 H), 1.77-1.87 (m, 2 H), 1.91-2.00 (m, 2 H), 2.32-2.44 (m, 1 H), 2.56-2.62 (m, 1 H), 2.81 (d, J = 11.3 Hz, 2 H), 3.13 (d, J = 5.5 Hz, 2 H), 3.23-3.33 (m, 4 H), 3.82 (s, 2 H), 4.00 (q, J = 7.0 Hz, 2 H), 7.21-7.28 (m, 1 H), 7.30-7.36 (m, 4 H) | I | m/z 454 (M + H)$^+$ (ES$^+$) at 5.89 min, UV active |
| 2-60 | Isomer 2: Ethyl 2-{4-[ethyl(1,3-oxazol-5-ylmethyl)amino]piperidin-1-yl}-6-azaspiro[3.4]octane-6-carboxylate | 4 and 133 | a | (400 MHz, DMSO-d$_6$) δ: 0.96 (t, J = 7.0 Hz, 3 H), 1.18 (t, J = 7.2 Hz, 3 H), 1.35-1.47 (m, 2 H), 1.60-1.72 (m, 4 H), 1.73-1.90 (m, 4 H), 1.94-2.03 (m, 2 H), 2.37-2.46 (m, 2 H), 2.59-2.68 (m, 2 H), 2.77-2.86 (m, 2 H), 3.10-3.22 (m, 2 H), 3.25-3.33 (m, 2 H), 3.71 (s, 2 H), 4.01 (q, J = 7.0 Hz, 2 H), 7.02 (s, 1 H), 8.27 (s, 1 H) | I | m/z 391 (M + H)$^+$ (ES$^+$) at 3.85 min, UV active |
| 2-61 | Isomer 2: Ethyl 2-{4-[(2-fluoroethyl)(1,3-oxazol-5-ylmethyl)amino]piperidin-1-yl}-6-azaspiro[3.4]octane-6-carboxylate | 4 and 135 | a | (400 MHz, MeOD-d$_4$) δ: 1.27 (t, J = 7.2 Hz, 3 H), 1.53-1.68 (m, 2 H), 1.81-2.03 (m, 8 H), 2.08-2.19 (m, 2 H), 2.57-2.68 (m, 1 H), 2.73-2.84 (m, 1 H), 2.89 (t, J = 5.3 Hz, 1 H), 2.92-3.03 (m, 3 H), 3.29 (s, 2 H), 3.41 (q, J = 6.9 Hz, 2 H), 3.92 (s, 2 H), 4.12 (q, J = 7.1 Hz, 2 H), 4.37 (t, J = 5.3 Hz, 1 H), 4.49 (t, J = 5.3 Hz, 1 H), 7.06 (s, 1 H), 8.18 (s, 1 H) | I | m/z 409 (M + H)$^+$ (ES$^+$) at 3.82 min, UV active |
| 2-62 | Isomer 2: Ethyl 2-{4-[(1,3-oxazol-5-ylmethyl)(2,2,2-trifluoroethyl)amino]piperidin-1-yl}-6-azaspiro[3.4]octane-6-carboxylate | 4 and 136 | a | (400 MHz, MeOD-d$_4$) δ: 1.27 (t, J = 7.0 Hz, 3 H), 1.52-1.66 (m, 2 H), 1.82-2.02 (m, 8 H), 2.12-2.20 (m, 2 H), 2.65-2.77 (m, 1 H), 2.81-2.93 (m, 1 H), 2.97-3.08 (m, 2 H), 3.25-3.32 (m, 4 H), 3.41 (q, J = 6.9 Hz, 2 H), 4.00 (s, 2 H), 4.12 (q, J = 7.0 Hz, 2 H), 7.07 (s, 1 H), 8.19 (s, 1 H) | I | m/z 445 (M + H)$^+$ (ES$^+$) at 4.47 min, UV active |
| 2-63 | Isomer 2b: Ethyl 2-(4-{1-[acetyl(ethyl)amino]propyl}piperidin-1-yl)-6-azaspiro[3.4]octane-6-carboxylate | 4 and 138 | e | (400 MHz, MeOD-d$_4$) δ: 0.82-0.97 (m, 3 H), 1.12-1.42 (m, 10 H), 1.43-2.01 (m, 10 H), 2.03-2.25 (m, 5 H), 2.69-2.83 (m, 1 H), 2.85-3.06 (m, 2 H), 3.14-3.33 (m, 4 H), 3.37-3.46 (m, 2 H), 4.12 (q, J = 6.8 Hz, 2 H) | I | m/z 394 (M + H)$^+$ (ES$^+$) at 3.99 min, UV active |
| 2-64 | Isomer 2: Ethyl 2-(4-{2-[acetyl(ethyl)amino]propan-2-yl}piperidin-1-yl)-6-azaspiro[3.4]octane-6-carboxylate | 4 and 140 | a | (400 MHz, MeOD-d$_4$) δ: 1.20-1.31 (m, 6 H), 1.31-1.43 (m, 2 H), 1.43 (s, 6 H), 1.50-1.57 (m, 2 H), 1.71-1.80 (m, 2 H), 1.88-2.00 (m, 4 H), 2.08-2.20 (m, 5 H), 2.69-2.82 (m, 2 H), 2.94-3.03 (m, 2 H), 3.29 (s, 2 H), 3.37-3.47 (m, 4 H), 4.12 (q, J = 6.8 Hz, 2 H) | I | m/z 394 (M + H)$^+$ (ES$^+$) at 4.01 min, UV active |

TABLE 3-continued

| Ex. No. | Name | Intermediate | Synthetic method | ¹H NMR | LCMS Method | LCMS data |
|---|---|---|---|---|---|---|
| 2-65 | Isomer 1a: Ethyl 2-{4-[1-(1 H-pyrazol-1-yl)ethyl]piperidin-1-yl}-6-azaspiro[3.4]octane-6-carboxylate | 4 and 144 | f | (400 MHz, MeOD-d₄) δ: 1.08-1.42 (m, 7 H), 1.52 (d, J = 6.8 Hz, 3 H), 1.68-1.97 (m, 8 H), 2.05-2.21 (m, 2 H), 2.72-2.82 (m, 1 H), 2.82-2.91 (m, 1 H), 2.95-3.03 (m, 1 H), 3.35-3.41 (m, 3 H), 4.09-4.20 (m, 3 H), 6.30 (t, J = 2.2 Hz, 1 H), 7.52 (d, J = 2.0 Hz, 1 H), 7.67 (d, J = 2.0 Hz, 1 H) | I | m/z 361 (M + H)⁺ (ES⁺) at 3.87 min, UV active |
| 2-65 | Isomer 2a: Ethyl 2-{4-[1-(1 H-pyrazol-1-yl)ethyl]piperidin-1-yl}-6-azaspiro[3.4]octane-6-carboxylate | 4 and 144 | f | (400 MHz, MeOD-d₄) δ: 1.06-1.43 (m, 7 H), 1.52 (d, J = 6.4 Hz, 3 H), 1.64-2.02 (m, 8 H), 2.04-2.19 (m, 2 H), 2.69-2.81 (m, 1 H), 2.81-2.91 (m, 1 H), 2.93-3.02 (m, 1 H), 3.37-3.46 (m, 3 H), 4.06-4.22 (m, 3 H), 6.30 (t, J = 2.0 Hz, 1 H), 7.52 (d, J = 2.0 Hz, 1 H), 7.66 (d, J = 2.0 Hz, 1 H) | I | m/z 361 (M + H)⁺ (ES⁺) at 4.18 min, UV active |
| 2-66 | Isomer 2: Ethyl 2-[4-(1-phenylethoxy)piperidin-1-yl]-6-azaspiro[3.4]octane-6-carboxylate | 4 and 147 | a | (400 MHz, DMSO-d₆) δ: 1.17 (t, J = 7.2 Hz, 3 H), 1.31 (d, J = 6.4 Hz, 3H), 1.35-1.51 (m, 2 H), 1.58-1.70 (m, 1 H), 1.71-1.92 (m, 6 H), 1.92-2.02 (m, 2 H), 2.44-2.67 (m, 4 H), 3.11-3.22 (m, 3 H), 3.27 (q, J = 1.0 Hz, 2 H), 4.00 (q, J = 7.0 Hz, 2 H), 4.62 (q, J = 6.3 Hz, 1 H), 7.23-7.30 (m, 1 H), 7.31-7.40 (m, 4 H) | I | m/z 387 (M + H)⁺ (ES⁺) at 5.29 min, UV active |
| 2-67 | Isomer 2: Ethyl 2-[4-(benzylsulfanyl)piperidin-1-yl]-6-azaspiro[3.4]octane-6-carboxylate | 4 and 150 | a | (400 MHz, DMSO-d₆) δ: 1.17 (t, J = 7.1 Hz, 3 H), 1.35-1.49 (m, 2 H), 1.68-1.91 (m, 8 H), 1.92-2.02 (m, 2 H), 2.56-2.71 (m, 4 H), 3.15 (d, J = 6.6 Hz, 2 H), 3.28 (q, J = 6.9 Hz, 2 H), 3.78 (s, 2 H), 4.00 (q, J = 7.1 Hz, 2 H), 7.21-7.28 (m, 1 H), 7.28-7.36 (m, 4 H) | I | m/z 389 (M + H)⁺ (ES⁺) at 5.37 min, UV active |
| 3-1 | Racemic: Ethyl 6-{4-[acetyl(cyclopropyl)amino]piperidin-1-yl}-2-azaspiro[3.4]octane-2-carboxylate | 8 and 30 | a | (400 MHz, CDCl₃) δ: 0.80-0.94 (m, 4 H), 1.25 (t, J = 7.0 Hz, 3H), 1.50-1.58 (m, 1 H), 1.69-2.20 (m, 12 H), 2.23 (s, 3 H), 2.46-2.62 (m, 2 H), 2.99-3.09 (m, 2 H), 3.76-3.91 (m, 4 H), 4.11 (q, J = 7.0 Hz, 2 H) | I | m/z 364 (M + H)⁺ (ES⁺) at 3.60 min, UV active |
| 3-2 | Isomer 2: Methyl 6-{4-[acetyl(ethyl)amino]piperidin-1-yl}-2-azaspiro[3.4]octane-2-carboxylate | 2 and 152 | g | (400 MHz, MeOD-d₄) δ: 1.09-1.29 (m, 3 H), 1.48-1.62 (m, 1 H), 1.64-2.02 (m, 8 H), 2.03-2.26 (m, 6 H), 2.61-2.74 (m, 1 H), 3.07-3.19 (m, 2 H), 3.28-3.44 (m, 2 H), 3.67 (s, 3 H), 3.76-3.98 (m, 4 H), 4.21-4.33 (m, 1 H) | I | m/z 338 (M + H)⁺ (ES⁺) at 3.11 min, UV active |
| 3-3 | Isomer 2: Ethyl 6-{4-[acetyl(ethyl)amino]piperidin-1-yl}-2-azaspiro[3.4]octane-2-carboxylate | 2 and 153 | g | (400 MHz, MeOD-d₄) δ: 1.11-1.29 (m, 6 H), 1.49-1.62 (m, 1 H), 1.65-2.03 (m, 8 H), 2.04-2.13 (m, 1 H), 2.15 (d, J = 4.6 Hz, 3 H), 2.16-2.24 (m, 2 H), 2.61-2.74 (m, 1 H), 3.08-3.18 (m, 2 H), 3.29-3.42 (m, 2 H), 3.76-3.96 (m, 4 H), 4.10 (q, J = 7.2 Hz, 2 H), 4.22-4.32 (m, 1 H) | I | m/z 352 (M + H)⁺ (ES⁺) at 3.43 min, UV active |

Biological Activity

EXAMPLE A

Phospho-ERK1/2 Assays

Functional assays were performed using the Alphascreen Surefire phospho-ERK1/2 assay (Crouch & Osmond, *Comb. Chem. High Throughput Screen,* 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader. $pEC_{50}$ and $E_{max}$ figures were calculated from the resulting data for each receptor subtype.

The results are set out in Table 4 below.

For each example containing the 6-azaspiro[3.4]octane ring system two diastereomers exist which have been separated, unless stated otherwise, and assigned (Isomer 1, Isomer 2) based on their analytical LCMS retention time. In most examples, Isomer 1 is not active. Where further (chiral) isomers exist, these have sometimes been separated and assigned (Isomer 1a, Isomer 1b) based on their chiral separation retention time.

For each example containing the 2-azaspiro[3.4]octane ring system two enantiomers exist which have been separated, unless stated otherwise, and assigned (Isomer 1, Isomer 2) based on their chiral separation retention time.

Analytical data for active isomers is reported in Table 3. Data for several weakly active compounds are included in Table 4 to highlight preference of absolute stereochemistry.

TABLE 4

| | Muscarinic Activity | | | |
|---|---|---|---|---|
| Ex. No. | $pEC_{50}$ M1 (% Emax cf. ACh) | $pEC_{50}$ M2 (% Emax cf. ACh) | $pEC_{50}$ M3 (% Emax cf. ACh) | $pEC_{50}$ M4 (% Emax cf. ACh) |
| ACh | 8.3 (102) | 7.8 (105) | 8.1 (115) | 8.1 (110) |
| 1-1 | 5.6 (72) | NT | NT | 6.5 (77) |
| 1-2 | 5.2 (59) | NT | NT | 6.6 (103) |
| 2-1 Isomer 2 | 6.3 (88) | <4.7 (15) | <4.7 (13) | 7.9 (108) |
| 2-2 Isomer 2 | 6.2 (91) | <4.7 (18) | <4.7 (9) | 7.4 (99) |
| 2-3 Isomer 1 | 5.7 (78) | NT | NT | <4.7 (13) |
| 2-3 Isomer 2 | 6.7 (93) | <4.7 (13) | <4.7 (6) | 7.5 (93) |
| 2-4 Isomer 2 | 6.7 (104) | <4.7 (3) | <4.7 (9) | 7.5 (114) |
| 2-5 Isomer 2 | 6.2 (57) | <4.7 (5) | <4.7 (5) | 7.0 (91) |
| 2-6 Isomer 2 | 7.0 (101) | <4.7 (7) | <4.7 (14) | 7.5 (98) |
| 2-7 Isomer 2 | 7.1 (120) | <4.7 (16) | <4.7 (10) | 7.9 (118) |
| 2-8 Isomer 2 | <4.7 (4) | <4.7 (6) | <4.7 (6) | 7.7 (57) |
| 2-9 Isomer 2 | <4.7 (14) | <4.7 (6) | <4.7 (5) | 7.0 (92) |
| 2-10 Isomer 2 | 6.1 (42) | <4.7 (11) | <4.7 (7) | 7.5 (122) |
| 2-11 Isomer 2 | <4.7 (9) | NT | NT | 6.5 (25) |
| 2-12 Isomer 2 | <4.7 (6) | NT | NT | 6.7 (41) |
| 2-13 Isomer 2 | <4.7 (18) | <4.7 (5) | <4.7 (4) | 6.9 (88) |
| 2-14 Isomer 2 | 5.6 (47) | <4.7 (12) | <4.7 (5) | 7.0 (108) |
| 2-15 Isomer 2 | 6.3 (117) | NT | NT | 6.7 (95) |
| 2-16 Isomer 2 | 6.4 (89) | <4.7 (5) | <4.7 (2) | 7.4 (91) |
| 2-17 Isomer 1 | <4.7 (27) | NT | NT | 5.9 (87) |
| 2-17 Isomer 2 | 5.9 (80) | NT | NT | 6.7 (92) |
| 2-18 Isomer 2 | 5.7 (89) | NT | NT | 6.7 (107) |
| 2-19 Isomer 1 | 5.9 (32) | NT | NT | 6.6 (62) |
| 2-19 Isomer 2 | 7.0 (115) | <4.7 (31) | <4.7 (58) | 7.2 (118) |
| 2-20 Isomer 1 | <4.7 (17) | NT | NT | 6.0 (36) |
| 2-20 Isomer 2 | 6.7 (113) | <4.7 (60) | <4.7 (33) | 7.4 (108) |
| 2-21 Isomer 1 | 4.8 (51) | NT | NT | 6.5 (46) |
| 2-21 isomer 2 | 7.2 (89) | <4.7 (18) | <4.7 (22) | 6.8 (93) |
| 2-22 Isomer 2 | 6.5 (132) | NT | NT | 7.1 (139) |
| 2-23 Isomer 2 | 5.9 (43) | NT | NT | 6.2 (65) |
| 2-24 Isomer 2 | 6.4 (91) | <4.7 (5) | <4.7 (17) | 8.0 (124) |
| 2-25 Isomer 2 | 5.4 (125) | NT | NT | 7.0 (101) |
| 2-26 Isomer 1 | <4.7 (23) | NT | NT | 6.0 (52) |
| 2-26 Isomer 2 | 6.4 (109) | NT | NT | 7.2 (114) |
| 2-27 Isomer 2 | 6.2 (108) | NT | NT | 7.1 (105) |
| 2-28 Isomer 2 | 6.8 (124) | NT | NT | 6.6 (80) |
| 2-29 Isomer 1 | <4.7 (17) | NT | NT | 5.9 (56) |
| 2-29 Isomer 2 | 6.7 (99) | 5.9 (29) | <4.7 (73) | 6.8 (84) |
| 2-30 Isomer 1 | 5.9 (33) | NT | NT | 6.9 (59) |
| 2-30 Isomer 2 | 7.0 (104) | 5.3 (42) | <4.7 (26) | 7.1 (96) |
| 2-31 Isomer 1 | 5.4 (27) | NT | NT | 6.7 (62) |
| 2-31 Isomer 2 | 6.4 (78) | NT | NT | 7.4 (95) |
| 2-32 Isomer 2 | 5.6 (82) | <4.7 (9) | <4.7 (5) | 7.4 (115) |
| 2-33 Isomer mixture | 6.7 (97) | NT | NT | 6.7 (78) |
| 2-34 Isomer mixture | 6.8 (116) | NT | NT | 6.2 (56) |
| 2-35 Isomer 2 | 7.4 (85) | <4.7 (21) | <4.7 (34) | 6.9 (72) |
| 2-36 Isomer 2 | 5.6 (45) | NT | NT | 6.2 (71) |
| 2-37 Isomer 2 | 5.9 (26) | NT | NT | 6.2 (55) |
| 2-38 Isomer 2 | 6.2 (76) | <4.7 (21) | <5.2 (1) | 7.7 (115) |
| 2-39 Isomer 2 | 6.5 (39) | <4.7 (12) | <4.7 (25) | 7.6 (126) |
| 2-40 Isomer 2 | 6.3 (39) | <4.7 (32) | <4.7 (9) | 7.2 (110) |
| 2-41 Isomer 2 | 6.5 (109) | <4.7 (57) | <4.7 (1) | 7.8 (127) |
| 2-42 Isomer 2 | 5.8 (120) | <4.7 (21) | <4.7 (39) | 7.0 (112) |
| 2-43 Isomer 2 | 5.6 (35) | NT | NT | 6.9 (91) |
| 2-44 isomer 2 | 5.6 (55) | NT | NT | 6.4 (80) |
| 2-45 Isomer 2 | 6.2 (30) | <4.7 (9) | <4.7 (16) | 7.2 (45) |
| 2-46 Isomer 2 | 6.5 (63) | <4.7 (5) | <4.7 (12) | 8.1 (98) |
| 2-47 Isomer 2 | 6.4 (113) | 6.3 (29) | 5.9 (63) | 7.2 (90) |
| 2-48 Isomer 2 | 7.4 (117) | 4.9 (68) | 5.1 (53) | 7.4 (75) |
| 2-49 Isomer 2 | <4.7 (8) | NT | NT | 5.9 (78) |
| 2-50 Isomer 2 | <4.7 (17) | NT | NT | 6.6 (70) |
| 2-51 Isomer 2 | 6.5 (84) | <4.7 (18) | <4.7 (22) | 7.7 (89) |
| 2-52 Isomer 2 | 6.4 (93) | <4.7 (7) | <4.7 (7) | 7.6 (106) |
| 2-53 Isomer 2 | <4.7 (42) | NT | NT | 6.6 (62) |
| 2-54 Isomer 2 | 6.6 (106) | <4.7 (28) | <4.7 (20) | 7.5 (98) |
| 2-55 Isomer 2 | <4.7 (161) | <4.7 (15) | <4.7 (5) | 7.6 (65) |
| 2-56 Isomer 2 | <4.7 (7) | NT | NT | 5.9 (41) |
| 2-57 Isomer 2 | 6.0 (40) | <4.7 (11) | <4.7 (23) | 7.4 (107) |
| 2-58 Isomer 2 | 5.9 (63) | NT | NT | 6.6 (74) |
| 2-59 Isomer 2 | <4.7 (9) | <4.7 (9) | <4.7 (14) | 7.1 (52) |
| 2-60 Isomer 2 | <4.7 (62) | <4.7 (20) | <4.7 (56) | 7.2 (111) |
| 2-61 Isomer 2 | <4.7 (21) | <4.7 (52) | <4.7 (65) | 7.4 (101) |
| 2-62 Isomer 2 | 6.0 (85) | <4.7 (12) | <4.7 (11) | 7.7 (106) |
| 2-63 Isomer 2b | <4.7 (7) | NT | NT | 6.2 (86) |
| 2-64 Isomer 2 | 5.6 (46) | <4.7 (2) | <4.7 (4) | 7.5 (128) |
| 2-65 Isomer 1a | 5.1 (45) | NT | NT | <4.7 (14) |
| 2-65 Isomer 2a | 6.0 (43) | <4.7 (15) | <4.7 (15) | 6.7 (45) |
| 2-66 Isomer 2 | <4.7 (59) | <4.7 (17) | <4.7 (8) | 7.4 (76) |
| 2-67 Isomer 2 | <4.7 (19) | <4.7 (2) | <4.7 (2) | 7.5 (55) |
| 3-1 Racemic | <4.7 (19) | <4.7 (2) | <4.7 (5) | 8.0 (46) |
| 3-2 Isomer 2 | 6.5 (42) | <4.7 (29) | <4.7 (37) | 7.5 (94) |
| 3-3 Isomer 2 | <4.7 (18) | <4.7 (3) | <4.7 (21) | 8.4 (93) |

EXAMPLE B

Effect of a Novel Test Compound and Xanomeline on d-Amphetamine-Induced Hyperactivity in Rats The aim of the study is to examine the effect of a novel test compound on d-amphetamine induced hyperactivity in rats. Schizophrenia is a complex multifactorial disease that cannot be fully represented by a single experimental procedure. Antipsychotic-like behaviour was assessed in rats by the inhibition of hyperactivity (or hyperlocomotion) elicited by d-amphetamine. This procedure is sensitive to clinically relevant dopamine receptor antagonists and is therefore considered suitable for comparing muscarinic agonists that influence dopaminergic signalling. A dose of xanomeline previously observed to significantly reduce d-amphetamine induced hyperactivity was employed as a positive control. Statistical analysis typically involved three-way analysis of covariance or robust regression with treatment, day and rack as factors and activity during the 30 minutes prior to treatment as a covariate, followed by appropriate multiple comparison tests. A P value of <0.05 was considered statistically significant and is marked accordingly in all subsequent figures.

Data for Example 2-1 Isomer 2 is shown in FIG. 1.

EXAMPLE C

Pharmaceutical Formulations
(i) Tablet Formulation
A tablet composition containing a compound of the formula (1) or formula (1a) is prepared by mixing 50 mg of the compound with 197 mg of lactose (BP) as diluent, and 3 mg magnesium stearate as a lubricant and compressing to form a tablet in known manner.
(ii) Capsule Formulation
A capsule formulation is prepared by mixing 100 mg of a compound of the formula (1) or formual (1a) with 100 mg lactose and optionally 1% by weight of magnesium stearate and filling the resulting mixture into standard opaque hard gelatin capsules.

Equivalents

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of treating a cognitive disorder or psychotic disorder in a subject, wherein the cognitive disorder or psychotic disorder is selected from the group consisting of dementia with Lewy bodies, Alzheimer's disease and schizophrenia, comprising administering to the subject in need thereof an effective amount of a compound of formula (1a):

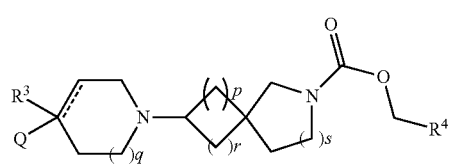

(1a)

or a salt thereof, wherein
is 1 or 2;
q is 0, 1 or 2;
r is 1 or 2;
s is 0 or 1, where the total of r and s is 1 or 2;
Q is $CR^1R^2NR^5R^6$, $NR^5R^6$, $OR^7$ or $SR^7$;

$R^1$ is selected from hydrogen and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^2$ is selected from hydrogen and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

$R^3$ is selected from hydrogen; fluorine; cyano; hydroxy; amino; and a $C_{1-6}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$ is selected from hydroxy; $OR^7$; $COR^7$; $COOR^7$; $CH_2COR^7$; $CH_2COOR^7$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;

$R^6$ is selected from hydroxy; $OR^7$; $COR^7$; $COOR^7$; $CH_2COR^7$; $CH_2COOR^7$; a $C_{1-6}$ non-aromatichydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;

$R^7$ is selected from hydrogen; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ or $C_{1-4}$ hydrocarbon group-W where W is an optionally substituted 5- or 6-membered ring containing 0, 1, 2 or 3 heteroatoms selected from O, N and S and oxidized forms thereof; and the dotted line indicates an optional second carbon-carbon bond, provided that when a second carbon-carbon bond is present, then $R^3$ is absent.

2. The method according to claim 1, wherein the compound is represented by formula (1):

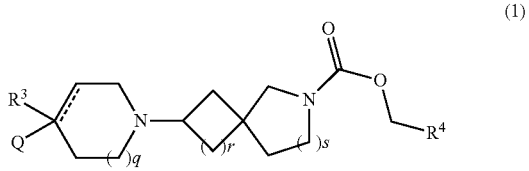

or a salt thereof, wherein
q is 0, 1 or 2;
r is 1 or 2;
s is 0 or 1, where the total of r and s is 1 or 2;
Q is $CR^1R^2NR^5R^6$, $NR^5R^6$, $OR^7$ or $SR^7$;
$R^1$ is selected from hydrogen and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;
$R^2$ is selected from hydrogen and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;
$R^3$ is selected from hydrogen; fluorine; cyano; hydroxy; amino; and a $C_{1-6}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;
$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
$R^5$ is selected from hydroxy; $OR^7$; $COR^7$; $COOR^7$; $CH_2COR^7$; $CH_2COOR^7$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;
$R^6$ is selected from hydroxy; $OR^7$; $COR^7$; $COOR^7$; $CH_2COR^7$; $CH_2COOR^7$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;
$R^7$ is selected from hydrogen; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and a group W or $CH_2W$ where W is an optionally substituted 5- or 6-membered ring containing 0, 1, 2 or 3 heteroatoms selected from O, N and S and oxidized forms thereof;
and the dotted line indicates an optional second carbon-carbon bond, provided that when a second carbon-carbon bond is present, then $R^3$ is absent.

3. The method according to claim 1, wherein Q is $NR^5R^6$.
4. The method according to claim 1, wherein Q is $CR^1R^2NR^5R^6$.
5. The method according to claim 1, wherein $R^1$ is selected from hydrogen, methyl and ethyl.
6. The method according to claim 1, wherein $R^2$ is selected from hydrogen, methyl and ethyl.
7. The method according to claim 1, wherein $R^5$ is selected from a $C_{1-4}$ alkyl group which is optionally substituted with one to four fluorine atoms; and a group W or $CH_2W$ where W is an optionally substituted 5- or 6-membered aromatic ring containing 0, 1, 2 or 3 heteroatoms selected from O, N and S.
8. The method according to claim 7, wherein $R^5$ is selected from methyl, ethyl, propyl, isopropyl, cyclopropyl, fluoroethyl, difluoroethyl, butyl and cyclobutyl.
9. The method according to claim 7, wherein $R^5$ is a group W or $CH_2W$ where W is an optionally substituted phenyl, pyridyl or isoxazole ring.
10. The method according to claim 1, wherein $R^6$ is selected from
$COR^7$; $COOR^7$; $CH_2COR^7$; $CH_2COOR^7$ and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.
11. The method according to claim 10, wherein $R^6$ is selected from methyl, ethyl, trifluoroethyl, hydroxyethyl and methoxyethyl.
12. The method according to claim 10, wherein $R^6$ is selected from
$COR^7$; $COOR^7$; $CH_2COR^7$; and $CH_2COOR^7$, wherein $R^7$ is selected from H, methyl, fluoromethyl, difluoromethyl, trifluoromethyl, ethyl, fluoroethyl, difluoroethyl and trifluoroethyl.
13. The method according to claim 1, wherein the moiety:

is selected from groups A to KKK as follows:

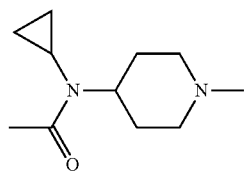

A

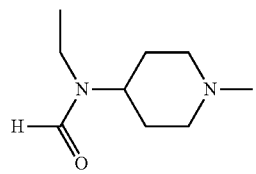

B

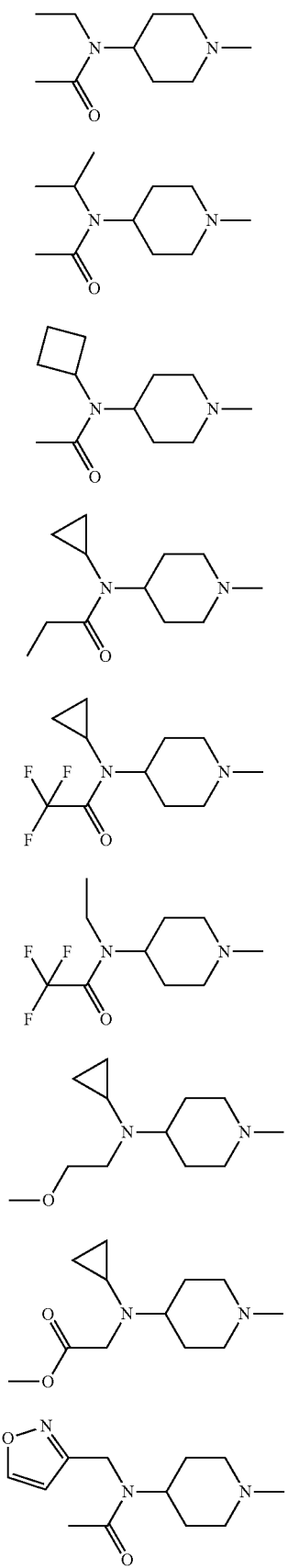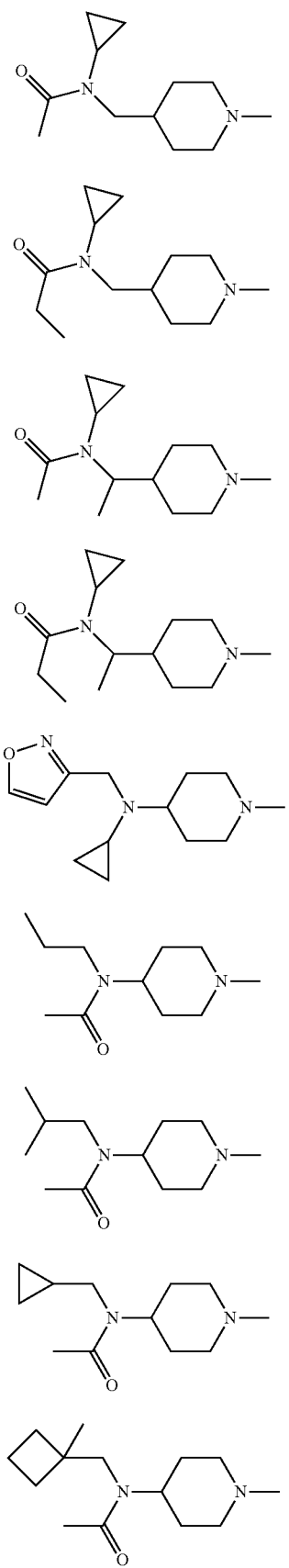

| | |
|---|---|
| U | CC |
| V | DD |
| W | EE |
| X | FF |
| Y | GG |
| Z | HH |
| AA | II |
| BB | JJ |

| | | |
|---|---|---|
| KK | 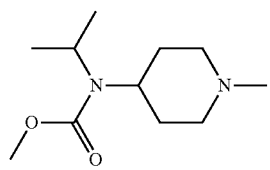 | TT 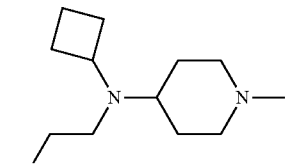 |
| LL | 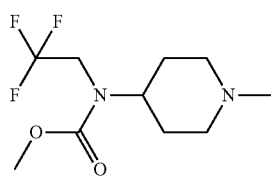 | UU 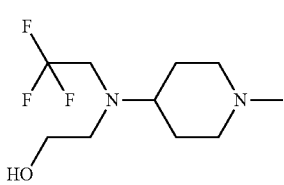 |
| MM | 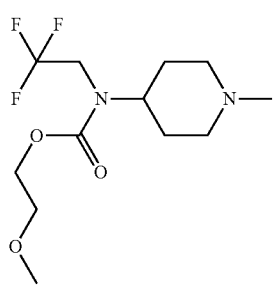 | VV 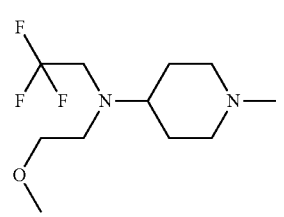 |
| NN | 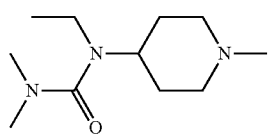 | WW 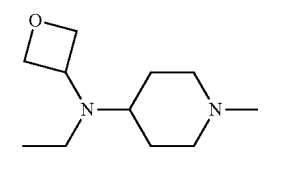 |
| OO | 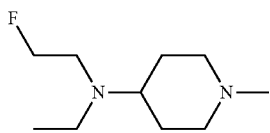 | XX 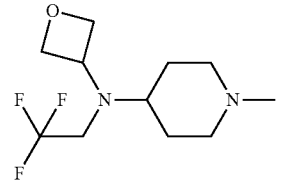 |
| PP | 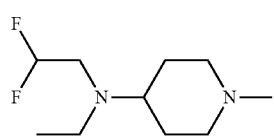 | YY 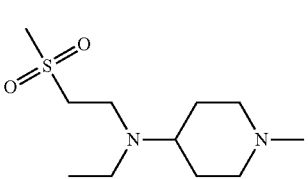 |
| QQ | 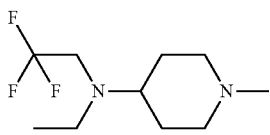 | ZZ |
| RR | 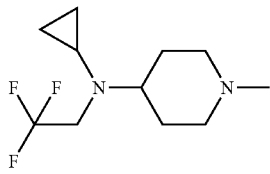 | AAA |
| SS | 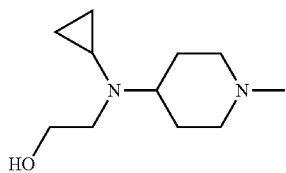 | BBB 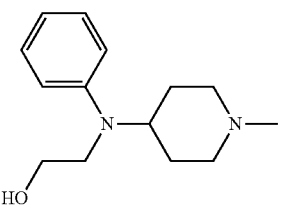 |

14. The method according to claim 1, wherein R³ is present and the optional second carbon-carbon bond is absent.

15. The method according to claim 14, wherein R³ is selected from hydrogen; fluorine; hydroxyl, methoxy and cyano.

16. The method according to claim 15, wherein R³ is hydrogen.

17. The method according to claim 1, wherein R⁴ is selected from hydrogen and methyl.

18. The method according to claim 1 which is
Ethyl 6-{4-[acetyl(cyclopropyl)amino]piperidin-1-yl}-2-azaspiro[3.3]heptane-2-carboxylate;
Ethyl 6-{4-[acetyl(ethyl)amino]piperidin-1-yl}-2-azaspiro[3.3]heptane-2-carboxylate;
Ethyl 2-{4-[acetyl(ethyl)amino]piperidin-1-yl}-6-azaspiro[3.4]octane-6-carboxylate;
Ethyl 2-{4-[acetyl(propan-2-yl)amino]piperidin-1-yl}-6-azaspiro[3.4]octane-6-carboxylate;
Ethyl 2-{4-[acetyl(cyclopropyl)amino]piperidin-1-yl}-6-azaspiro[3.4]octane-6-carboxylate;
Ethyl 2-{4-[cyclopropyl(trifluoroacetyl)amino]piperidin-1-yl}-6-azaspiro[3.4]octane-6-carboxylate;
Ethyl 2-{4-[cyclopropyl(propanoyl)amino]piperidin-1-yl}-6-azaspiro[3.4]octane-6-carboxylate;
Ethyl 2-{4-[acetyl(cyclobutyl)amino]piperidin-1-yl}-6-azaspiro[3.4]octane-6-carboxylate;
Ethyl 2-{4-[ethyl(2,2,2-trifluoroethyl)amino]piperidin-1-yl}-6-azaspiro[3.4]octane-6-carboxylate;
Ethyl 2-{4-[cyclopropyl(2-methoxyethyl)amino]piperidin-1-yl}-6-azaspiro[3.4]octane-6-carboxylate;
Ethyl 2-{4-[cyclopropyl(2-methoxy-2-oxoethyl)amino]piperidin-1-yl}-6-azaspiro[3.4]octane-6-carboxylate;
Ethyl 2-{4-[cyclopropyl(1,2-oxazol-3-ylmethyl)amino]piperidin-1-yl}-6-azaspiro[3.4]octane-6-carboxylate;
Ethyl 2-(4-{[acetyl(cyclopropyl)amino]methyl}piperidin-1-yl)-6-azaspiro[3.4]octane-6-carboxylate;
Ethyl 2-(4-{[cyclopropyl(propanoyl)amino]methyl}piperidin-1-yl)-6-azaspiro[3.4]octane-6-carboxylate;
Ethyl 2-(4-{1-[acetyl(cyclopropyl)amino]ethyl}piperidin-1-yl)-6-azaspiro[3.4]octane-6-carboxylate;
Ethyl 2-(4-{1-[cyclopropyl(propanoyl)amino]ethyl}piperidin-1-yl)-6-azaspiro[3.4]octane-6-carboxylate;
Methyl 2-{4-[acetyl(cyclobutyl)amino]piperidin-1-yl}-6-azaspiro[3.4]octane-6-carboxylate;
Ethyl 2-{4-[ethyl(formyl)amino]piperidin-1-yl}-6-azaspiro[3.4]octane-6-carboxylate;
Methyl 2-{4-[acetyl(ethyl)amino]piperidin-1-yl}-6-azaspiro[3.4]octane-6-carboxylate;
Ethyl 2-{4-[acetyl(propyl)amino]piperidin-1-yl}-6-azaspiro[3.4]octane-6-carboxylate;

Ethyl 2-{4-[acetyl(2-methylpropyl)amino]piperidin-1-yl}-6-azaspiro[3.4]octane-6-carboxylate;
Ethyl 2-{4-[acetyl(cyclopropylmethyl)amino]piperidin-1-yl}-6-azaspiro[3.4]octane-6-carboxylate;
Ethyl 2-(4-{acetyl[(1-methylcyclobutyl)methyl]amino}piperidin-1-yl)-6-azaspiro[3.4]octane-6-carboxylate;
Ethyl 2-{4-[acetyl(1-methylcyclobutyl)amino]piperidin-1-yl}-6-azaspiro[3.4]octane-6-carboxylate;
Ethyl 2-(4-{acetyl[(3-methyloxetan-3-yl)methyl]amino}piperidin-1-yl)-6-azaspiro[3.4]octane-6-carboxylate;
Ethyl 2-{4-[acetyl(2,2-difluoroethyl)amino]piperidin-1-yl}-6-azaspiro[3.4]octane-6-carboxylate;
Ethyl 2-{4-[acetyl(2,2,2-trifluoroethyl)amino]piperidin-1-yl}-6-azaspiro[3.4]octane-6-carboxylate;
Ethyl 2-{4-[acetyl(2-fluoro-2-methylpropyl)amino]piperidin-1-yl}-6-azaspiro[3.4]octane-6-carboxylate;
Ethyl 2-{4-[acetyl(2,2-difluoropropyl)amino]piperidin-1-yl}-6-azaspiro[3.4]octane-6-carboxylate;
Ethyl 2-{4-[acetyl(3,3-difluorocyclobutyl)amino]piperidin-1-yl}-6-azaspiro[3.4]octane-6-carboxylate;
Ethyl 2-{4-[acetyl(2-methoxy-2-methylpropyl)amino]piperidin-1-yl}-6-azaspiro[3.4]octane-6-carboxylate;
Ethyl 2-(4-{acetyl[(1-methoxycyclobutyl)methyl]amino}piperidin-1-yl)-6-azaspiro[3.4]octane-6-carboxylate;
Ethyl 2-(4-{acetyl[(1-hydroxycyclobutyl)methyl]amino}piperidin-1-yl)-6-azaspiro[3.4]octane-6-carboxylate;
Ethyl 2-{4-[acetyl(methoxy)amino]piperidin-1-yl}-6-azaspiro[3.4]octane-6-carboxylate;
Ethyl 2-{4-[acetyl(phenyl)amino]piperidin-1-yl}-6-azaspiro[3.4]octane-6-carboxylate;
Ethyl 2-{4-[acetyl(pyridin-2-yl)amino]piperidin-1-yl}-6-azaspiro[3.4]octane-6-carboxylate;
Ethyl 2-{4-[acetyl(benzyl)amino]piperidin-1-yl}-6-azaspiro[3.4]octane-6-carboxylate;
Ethyl 2-{4-[acetyl(1,3-oxazol-5-ylmethyl)amino]piperidin-1-yl}-6-azaspiro[3.4]octane-6-carboxylate;
Ethyl 2-{4-[acetyl(1,3-oxazol-2-ylmethyl)amino]piperidin-1-yl}-6-azaspiro[3.4]octane-6-carboxylate;
(1,1-$^2$H$_2$)-Ethyl 2-{4-[acetyl(ethyl)amino]piperidin-1-yl}-6-azaspiro[3.4]octane-6-carboxylate;
Ethyl 2-{4-[ethyl(methoxycarbonyl)amino]piperidin-1-yl}-6-azaspiro[3.4]octane-6-carboxylate;
Ethyl 2-{4-[(ethoxycarbonyl)(ethyl)amino]piperidin-1-yl}-6-azaspiro[3.4]octane-6-carboxylate;
Ethyl 2-{4-[(methoxycarbonyl)(propan-2-yl)amino]piperidin-1-yl}-6-azaspiro[3.4]octane-6-carboxylate;
Ethyl 2-{4-[(methoxycarbonyl)(2,2,2-trifluoroethyl)amino]piperidin-1-yl}-6-azaspiro[3.4]octane-6-carboxylate;
Ethyl 2-(4-{[(2-methoxyethoxy)carbonyl](2,2,2-trifluoroethyl)amino}piperidin-1-yl)-6-azaspiro[3.4]octane-6-carboxylate;
Ethyl 2-{4-[(dimethylcarbamoyl)(ethyl)amino]piperidin-1-yl}-6-azaspiro[3.4]octane-6-carboxylate;
Ethyl 2-{4-[ethyl(2-fluoroethyl)amino]piperidin-1-yl}-6-azaspiro[3.4]octane-6-carboxylate;
Ethyl 2-{4-[(2,2-difluoroethyl)(ethyl)amino]piperidin-1-yl}-6-azaspiro[3.4]octane-6-carboxylate;
Ethyl 2-{4-[(methoxycarbonyl)(oxetan-3-yl)amino]piperidin-1-yl}-6-azaspiro[3.4]octane-6-carboxylate;
Ethyl 2-{4-[cyclopropyl(2,2,2-trifluoroethyl)amino]piperidin-1-yl}-6-azaspiro[3.4]octane-6-carboxylate;
Ethyl 2-{4-[cyclopropyl(2-hydroxyethyl)amino]piperidin-1-yl}-6-azaspiro[3.4]octane-6-carboxylate;
Ethyl 2-{4-[cyclobutyl(2-hydroxyethyl)amino]piperidin-1-yl}-6-azaspiro[3.4]octane-6-carboxylate;
Ethyl 2-{4-[(2-hydroxyethyl)(2,2,2-trifluoroethyl)amino]piperidin-1-yl}-6-azaspiro[3.4]octane-6-carboxylate;
Ethyl 2-{4-[(2-methoxyethyl)(2,2,2-trifluoroethyl)amino]piperidin-1-yl}-6-azaspiro[3.4]octane-6-carboxylate;
Ethyl 2-{4-[ethyl(oxetan-3-yl)amino]piperidin-1-yl}-6-azaspiro[3.4]octane-6-carboxylate;
Ethyl 2-{4-[oxetan-3-yl(2,2,2-trifluoroethyl)amino]piperidin-1-yl}-6-azaspiro[3.4]octane-6-carboxylate;
Ethyl 2-{4-[(2-cyanoethyl)(ethyl)amino]piperidin-1-yl}-6-azaspiro[3.4]octane-6-carboxylate;
Ethyl 2-(4-{ethyl[2-(methylsulfonyl)ethyl]amino}piperidin-1-yl)-6-azaspiro[3.4]octane-6-carboxylate;
Ethyl 2-{4-[ethyl(methoxy)amino]piperidin-1-yl}-6-azaspiro[3.4]octane-6-carboxylate;
Ethyl 2-{4-[(2-hydroxyethyl)(phenyl)amino]piperidin-1-yl}-6-azaspiro[3.4]octane-6-carboxylate;
Ethyl 2-{4-[benzyl(2,2,2-trifluoroethyl)amino]piperidin-1-yl}-6-azaspiro[3.4]octane-6-carboxylate;
Ethyl 2-{4-[ethyl(1,3-oxazol-5-ylmethyl)amino]piperidin-1-yl}-6-azaspiro[3.4]octane-6-carboxylate;
Ethyl 2-{4-[(2-fluoroethyl)(1,3-oxazol-5-ylmethyl)amino]piperidin-1-yl}-6-azaspiro[3.4]octane-6-carboxylate;
Ethyl 2-{4-[(1,3-oxazol-5-ylmethyl)(2,2,2-trifluoroethyl)amino]piperidin-1-yl}-6-azaspiro[3.4]octane-6-carboxylate;
Ethyl 2-(4-{1-[acetyl(ethyl)amino]propyl}piperidin-1-yl)-6-azaspiro[3.4]octane-6-carboxylate;
Ethyl 2-(4-{2-[acetyl(ethyl)amino]propan-2-yl}piperidin-1-yl)-6-azaspiro[3.4]octane-6-carboxylate;
Ethyl 2-{4-[1-(1H-pyrazol-1-yl)ethyl]piperidin-1-yl}-6-azaspiro[3.4]octane-6-carboxylate;
Ethyl 2-[4-(1-phenylethoxy)piperidin-1-yl]-6-azaspiro[3.4]octane-6-carboxylate;
Ethyl 2-[4-(benzylsulfanyl)piperidin-1-yl]-6-azaspiro[3.4]octane-6-carboxylate;
Ethyl 6-{4-[acetyl(cyclopropyl)amino]piperidin-1-yl}-2-azaspiro[3.4]octane-2-carboxylate;
Methyl 6-{4-[acetyl(ethyl)amino]piperidin-1-yl}-2-azaspiro[3.4]octane-2-carboxylate or
Ethyl 6-{4-[acetyl(ethyl)amino]piperidin-1-yl}-2-azaspiro[3.4]octane-2-carboxylate, or a salt of any of the foregoing.

19. The method of claim 1, wherein the cognitive disorder or the psychotic disorder is Alzheimer's disease.

20. The method of claim 1, wherein the cognitive disorder or the psychotic disorder is Schizophrenia.

21. The method of claim 1, wherein the cognitive disorder or the psychotic disorder is dementia with Lewy bodies.

22. The method of claim 1, wherein the compound is ethyl 6-{4-[acetyl(ethyl)amino]piperidin-1-yl}-2-azaspiro[3.3]heptane-2-carboxylate or a pharmaceutically acceptable salt thereof.

23. The method of claim 1, wherein the compound is ethyl 2-{4-[acetyl(ethyl)amino]piperidin-1-yl}-6-azaspiro[3.4]octane-6-carboxylate or a pharmaceutically acceptable salt thereof.

24. The method of claim 1, wherein the compound is ethyl 2-{4-[ethyl(2,2,2-trifluoroethyl)amino]piperidin-1-yl}-6-azaspiro[3.4]octane-6-carboxylate or a pharmaceutically acceptable salt thereof.

25. The method of claim 1, wherein the compound is methyl 2-{4-[acetyl(ethyl)amino]piperidin-1-yl}-6-azaspiro[3.4]octane-6-carboxylate or a pharmaceutically acceptable salt thereof.

26. The method of claim 1, wherein the compound is ethyl 2-{4-[acetyl(2,2-difluoroethyl)amino]piperidin-1-yl}-6-azaspiro[3.4]octane-6-carboxylate or a pharmaceutically acceptable salt thereof.

27. The method of claim 1, wherein the compound is (1,1-$^2$H$_2$)-ethyl 2-{4-[acetyl(ethyl)amino]piperidin-1-yl}-6-azaspiro[3.4]octane-6-carboxylate or a pharmaceutically acceptable salt thereof.

28. The method of claim 1, wherein the compound is ethyl 2-{4-[(2-methoxyethyl)(2,2,2-trifluoroethyl)amino]piperidin-1-yl}-6-azaspiro[3.4]octane-6-carboxylate or a pharmaceutically acceptable salt thereof.

29. The method of claim 1, wherein the compound is ethyl 2-{4-[ethyl(methoxy)amino]piperidin-1-yl}-6-azaspiro[3.4]octane-6-carboxylate or a pharmaceutically acceptable salt thereof.

30. The method of claim 1, wherein the compound is methyl 6-{4-[acetyl(ethyl)amino]piperidin-1-yl}-2-azaspiro[3.4]octane-2-carboxylate or a pharmaceutically acceptable salt thereof.

* * * * *

UNITED STATES PATENT AND TRADEMARK OFFICE
CERTIFICATE OF CORRECTION

PATENT NO. : 10,351,545 B2
APPLICATION NO. : 15/699674
DATED : July 16, 2019
INVENTOR(S) : Giles Albert Brown et al.

Page 1 of 1

It is certified that error appears in the above-identified patent and that said Letters Patent is hereby corrected as shown below:

In the Claims

At Column 131, Claim number 1, Line number 63, insert --p-- before "is 1 or 2;".

Signed and Sealed this
Tenth Day of December, 2019

Andrei Iancu
*Director of the United States Patent and Trademark Office*